US009717782B2

(12) United States Patent
Lewinsohn et al.

(10) Patent No.: US 9,717,782 B2

(45) Date of Patent: Aug. 1, 2017

(54) METHODS FOR PRODUCING AN IMMUNE RESPONSE TO TUBERCULOSIS

(71) Applicants: Oregon Health & Science University, Portland, CA (US); The United States Government as represented by the Department of Veterans Affairs, Washington, DC (US)

(72) Inventors: David M. Lewinsohn, Portland, OR (US); Deborah A. Lewinsohn, Portland, OR (US)

(73) Assignees: Oregon Health & Science University, Portland, OR (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/295,875

(22) Filed: Oct. 17, 2016

(65) Prior Publication Data

US 2017/0028048 A1 Feb. 2, 2017

Related U.S. Application Data

(60) Division of application No. 14/590,810, filed on Jan. 6, 2015, now Pat. No. 9,506,922, which is a continuation of application No. 13/510,862, filed as application No. PCT/US2010/057479 on Nov. 19, 2010, now Pat. No. 8,961,989.

(60) Provisional application No. 61/263,206, filed on Nov. 20, 2009.

(51) Int. Cl.

| | |
|---|---|
| ***A61K 39/04*** | (2006.01) |
| ***A61K 35/00*** | (2006.01) |
| ***A61K 39/385*** | (2006.01) |
| ***A61K 31/7088*** | (2006.01) |
| ***C07K 7/08*** | (2006.01) |
| ***C07K 7/06*** | (2006.01) |
| ***C12N 15/31*** | (2006.01) |
| ***C12N 1/21*** | (2006.01) |
| ***A61K 38/00*** | (2006.01) |
| ***A61P 37/04*** | (2006.01) |
| ***A61P 31/16*** | (2006.01) |
| ***A61K 49/00*** | (2006.01) |
| ***A61K 9/00*** | (2006.01) |
| ***G01N 33/569*** | (2006.01) |
| *A61K 39/00* | (2006.01) |

(52) U.S. Cl.

CPC ............ *A61K 39/04* (2013.01); *A61K 9/0021* (2013.01); *A61K 39/385* (2013.01); *A61K 49/00* (2013.01); *A61K 49/0006* (2013.01); *G01N 33/5695* (2013.01); *A61K 38/00* (2013.01); *A61K 2039/53* (2013.01); *G01N 2333/35* (2013.01); *G01N 2469/10* (2013.01); *G01N 2800/26* (2013.01)

(58) Field of Classification Search

None

See application file for complete search history.

(56) References Cited

U.S. PATENT DOCUMENTS

| | | | |
|---|---|---|---|
| 6,982,085 | B2 | 1/2006 | Anderson et al. |
| 6,991,797 | B2 | 1/2006 | Anderson et al. |
| 7,288,261 | B2 | 10/2007 | Orme et al. |
| 7,364,740 | B2 | 4/2008 | Behr et al. |
| 7,393,540 | B2 | 7/2008 | James et al. |
| 7,538,206 | B2 | 5/2009 | Cole |
| 2002/0131975 | A1 | 9/2002 | Horwitz et al. |
| 2003/0199012 | A1 | 10/2003 | Ho |
| 2003/0236393 | A1 | 12/2003 | Trucksis |
| 2004/0057963 | A1 | 3/2004 | Anderson et al. |
| 2004/0110269 | A1 | 6/2004 | Vipond et al. |
| 2004/0197896 | A1 | 10/2004 | Cole |
| 2004/0241826 | A1 | 12/2004 | James et al. |
| 2005/0250120 | A1 | 11/2005 | Cole et al. |
| 2007/0224217 | A1 | 9/2007 | Trucksis |
| 2008/0138356 | A1 | 6/2008 | Friedman et al. |
| 2008/0267990 | A1 | 10/2008 | Anderson et al. |
| 2009/0123492 | A1 | 5/2009 | Flores-Valdez et al. |
| 2009/0124549 | A1 | 5/2009 | Lewinsohn et al. |

FOREIGN PATENT DOCUMENTS

| | | |
|---|---|---|
| WO | WO 01/04151 | 1/2001 |
| WO | WO 01/79274 | 10/2001 |
| WO | WO 02/04018 | 1/2002 |
| WO | WO 03/033530 | 4/2003 |
| WO | WO 2005/076010 | 8/2005 |
| WO | WO 2007/106560 | 9/2007 |
| WO | WO 2008/124647 | 10/2008 |
| WO | WO 2011/063283 | 5/2011 |

OTHER PUBLICATIONS

Brosch et al., "Genome plasticity of BCG and impact on vaccine efficacy," *PNAS* 104(13): 5596-5601 (Mar. 27, 2007).
Cockle et al., "Identification of Novel *Mycobacterium tuberculosis* Antigens with Potential as Diagnostic Reagents or Subunit Vaccine Candidates by Comparative Genomics," *Infection and Immunity*, 70(12): 6996-7003 (2002).
Database Uniprot Accession No. A5U183 (online Jul. 10, 2007).
Database Uniprot Accession No. A5U7F1 (online Jul. 10, 2007).
Garnier et al., "The complete genome sequence of *Mycobacterium bovis*," *PNAS* 100(13):7877-7882 (Jun. 24, 2003).

(Continued)

*Primary Examiner* — Robert A Zeman

(74) *Attorney, Agent, or Firm* — Klarquist Sparkman, LLP

(57) ABSTRACT

Methods for producing an immune response to *Mycobacterium tuberculosis* (Mtb) are disclosed herein. In several examples, the immune response is a protective immune response. In additional embodiments, methods are disclosed for inhibiting an infection with Mtb, preventing an infection with Mtb, or treating an infection with Mtb. Pharmaceutical compositions for the inhibition, prevention and/or treatment of tuberculosis are also disclosed.

15 Claims, 5 Drawing Sheets

(56) References Cited

OTHER PUBLICATIONS

Greenspan et al., "Defining epitopes: It's not as easy as it seems," *Nature Biotechnology* 7: 936-937 (1999).

Larsen, "Prediction of T-cell Epitopes for Therapeutic and Prophylactic Vaccines," *Center for Biological Sequence Analysis BioCentrum. Technical University of Denmark* (154 pages) (2007).

Lewinsohn et al., "Immunodominant Tuberculosis CD8 Antigens Preferentially Restricted by HLA-B," *PLoS Pathogens* 3(9): 1240-1249 (2007).

Lewinsohn et al., "*Mycobacterium tuberculosis*-Specific $CD8^+$ T Cells Preferentially Recognize Heavily Infected Cells," *Am. J. Respir. Crit. Care Med.*, 168: 1346-1352 (2003).

NCBI Accession No. YP_177935, 2 pages (Apr. 24, 2009).

NCBI Genbank Accession No. NP_335505, 2 pages (Apr. 24, 2009).

NCBI Genbank Accession No. NP_337747, 2 pages (Apr. 24, 2009).

Seki et al., "Whole genome sequence analysis of *Mycobacterium bovis bacillus* Calmette-Guérin (BCG) Tokyo 172: A comparative study of BCG vaccine substrains," *Vaccine* 27(11):1710-1716 (2009).

Tuberculist Database Rv0394c, printed from http://genome.tbdb.org/annotation/genome/tbdb/GeneDetails.html?sp—S7000000635256770 (published on Jul. 27, 2009).

Tuberculist Database Rv1039c, printed from http://genome.tbdb.org/annotation/genome/tbdb/GeneDetails.html?sp—S7000000635246273 (published on Jun. 8, 2006).

Tuberculist Database Rv1076c, printed from http://genome.tbdb.org/annotation/genome/tbdb/GeneDetails.html?sp—S7000000635252927 (published on Jul. 27, 2009).

Tuberculist Database Rv3136, printed from http://genome.tbdb.org/annotation/genome/tbdb/GeneDetails.html?sp=S7000000635251322 (published on Jun. 10, 2009).

Tuberculist Database Rv3539, printed from http://genome.tbdb.orgiannotation/genome/tbdb/GeneDetails.html?sp=S7000000635255504 (published on Jul. 27, 2009).

Tuberculist Database Rv3641c, printed from http://genome.tbdb.orgiannotation/genome/tbdb/GeneDetails.html?sp=S7000000635256770 (published on Jul. 27, 2009).

Zvi et al., "Whole Genome Identification of *Mycobacterium tuberculosis* Vaccine Candidates by Comprehensive Data Mining and Bioinformatic Analyses," *BMC Med. Genomics*, I:18 (25 pages) (2008).

SEQUENCE LISTING

```
<160> NUMBER OF SEQ ID NOS: 36

<210> SEQ ID NO 1
<211> LENGTH: 211
<212> TYPE: PRT
<213> ORGANISM: Mycobacterium tuberculosis

<400> SEQUENCE: 1

Val Pro His Pro Trp Asp Thr Gly Asp His Glu Arg Asn Trp Gln Gly
1               5                   10                  15

Tyr Phe Ile Pro Ala Met Ser Val Leu Arg Asn Arg Val Gly Ala Arg
            20                  25                  30

Thr His Ala Glu Leu Arg Asp Ala Glu Asn Asp Leu Val Glu Ala Arg
        35                  40                  45

Val Ile Glu Leu Arg Glu Asp Pro Asn Leu Leu Gly Asp Arg Thr Asp
    50                  55                  60

Leu Ala Tyr Leu Arg Ala Ile His Arg Gln Leu Phe Gln Asp Ile Tyr
65                  70                  75                  80

Val Trp Ala Gly Asp Leu Arg Thr Val Gly Ile Glu Lys Glu Asp Glu
                85                  90                  95

Ser Phe Cys Ala Pro Gly Gly Ile Ser Arg Pro Met Glu His Val Ala
            100                 105                 110

Ala Glu Ile Tyr Gln Leu Asp Arg Leu Arg Ala Val Gly Glu Gly Asp
        115                 120                 125

Leu Ala Gly Gln Val Ala Tyr Arg Tyr Asp Tyr Val Asn Tyr Ala His
    130                 135                 140

Pro Phe Arg Glu Gly Asn Gly Arg Ser Thr Arg Glu Phe Phe Asp Leu
145                 150                 155                 160

Leu Leu Ser Glu Arg Gly Ser Gly Leu Asp Trp Gly Lys Thr Asp Leu
                165                 170                 175

Glu Glu Leu His Gly Ala Cys His Val Ala Arg Ala Asn Ser Asp Leu
            180                 185                 190

Thr Gly Leu Val Ala Met Phe Lys Gly Ile Leu Asp Ala Glu Pro Thr
        195                 200                 205

Tyr Asp Phe
    210


<210> SEQ ID NO 2
<211> LENGTH: 380
<212> TYPE: PRT
<213> ORGANISM: Mycobacterium tuberculosis

<400> SEQUENCE: 2

Met Asp Phe Ala Leu Leu Pro Pro Glu Val Asn Ser Ala Arg Met Tyr
```

-continued

```
1               5                   10                  15

Thr Gly Pro Gly Ala Gly Ser Leu Leu Ala Ala Ala Gly Gly Trp Asp
            20                  25                  30

Ser Leu Ala Ala Glu Leu Ala Thr Thr Ala Glu Ala Tyr Gly Ser Val
        35                  40                  45

Leu Ser Gly Leu Ala Ala Leu His Trp Arg Gly Pro Ala Ala Glu Ser
    50                  55                  60

Met Ala Val Thr Ala Ala Pro Tyr Ile Gly Trp Leu Tyr Thr Thr Ala
65                  70                  75                  80

Glu Lys Thr Gln Gln Thr Ala Ile Gln Ala Arg Ala Ala Ala Leu Ala
                85                  90                  95

Phe Glu Gln Ala Tyr Ala Met Thr Leu Pro Pro Pro Val Val Ala Ala
            100                 105                 110

Asn Arg Ile Gln Leu Leu Ala Leu Ile Ala Thr Asn Phe Phe Gly Gln
        115                 120                 125

Asn Thr Ala Ala Ile Ala Ala Thr Glu Ala Gln Tyr Ala Glu Met Trp
    130                 135                 140

Ala Gln Asp Ala Ala Ala Met Tyr Gly Tyr Ala Thr Ala Ser Ala Ala
145                 150                 155                 160

Ala Ala Leu Leu Thr Pro Phe Ser Pro Pro Arg Gln Thr Thr Asn Pro
                165                 170                 175

Ala Gly Leu Thr Ala Gln Ala Ala Ala Val Ser Gln Ala Thr Asp Pro
            180                 185                 190

Leu Ser Leu Leu Ile Glu Thr Val Thr Gln Ala Leu Gln Ala Leu Thr
        195                 200                 205

Ile Pro Ser Phe Ile Pro Glu Asp Phe Thr Phe Leu Asp Ala Ile Phe
    210                 215                 220

Ala Gly Tyr Ala Thr Val Gly Val Thr Gln Asp Val Glu Ser Phe Val
225                 230                 235                 240

Ala Gly Thr Ile Gly Ala Glu Ser Asn Leu Gly Leu Leu Asn Val Gly
                245                 250                 255

Asp Glu Asn Pro Ala Glu Val Thr Pro Gly Asp Phe Gly Ile Gly Glu
            260                 265                 270

Leu Val Ser Ala Thr Ser Pro Gly Gly Gly Val Ser Ala Ser Gly Ala
        275                 280                 285

Gly Gly Ala Ala Ser Val Gly Asn Thr Val Leu Ala Ser Val Gly Arg
    290                 295                 300

Ala Asn Ser Ile Gly Gln Leu Ser Val Pro Pro Ser Trp Ala Ala Pro
305                 310                 315                 320

Ser Thr Arg Pro Val Ser Ala Leu Ser Pro Ala Gly Leu Thr Thr Leu
                325                 330                 335

Pro Gly Thr Asp Val Ala Glu His Gly Met Pro Gly Val Pro Gly Val
            340                 345                 350

Pro Val Ala Ala Gly Arg Ala Ser Gly Val Leu Pro Arg Tyr Gly Val
        355                 360                 365

Arg Leu Thr Val Met Ala His Pro Pro Ala Ala Gly
    370                 375                 380
```

<210> SEQ ID NO 3
<211> LENGTH: 239
<212> TYPE: PRT
<213> ORGANISM: Mycobacterium tuberculosis

<400> SEQUENCE: 3

```
Met Thr Glu Pro Arg Pro Val Phe Ala Val Val Ile Ser Ala Gly Leu
1               5                   10                  15

Ser Ala Ile Pro Met Val Gly Gly Pro Leu Gln Thr Val Phe Asp Ala
            20                  25                  30

Ile Glu Glu Arg Thr Arg His Arg Ala Glu Thr Thr Thr Arg Glu Ile
        35                  40                  45

Cys Glu Ser Val Gly Gly Ala Asp Thr Val Leu Ser Arg Ile Asp Lys
    50                  55                  60

Asn Pro Glu Leu Glu Pro Leu Leu Ser Gln Ala Ile Glu Ala Ala Thr
65                  70                  75                  80

Arg Thr Ser Met Glu Ala Lys Arg Arg Leu Leu Ala Gln Ala Ala Ala
                85                  90                  95

Ala Ala Leu Glu Asp Asp Gln Lys Val Glu Pro Ala Ser Leu Ile Val
            100                 105                 110

Ala Thr Leu Ser Gln Leu Glu Pro Val His Ile His Ala Leu Val Arg
        115                 120                 125

Leu Ala Lys Ala Ala Lys Ser Ser Pro Asp Gln Asp Glu Ile Gln Arg
    130                 135                 140

Arg Glu Val Met Arg Ala Ala Ser Lys Val Glu Pro Val Pro Val Leu
145                 150                 155                 160

Ala Ala Leu Ile Gln Thr Gly Val Ala Ile Ala Thr Thr Thr Val Trp
                165                 170                 175

His Gly Asn Gly Thr Gly Thr Pro Ala Glu Glu Ser Gly His Ile Leu
            180                 185                 190

Ile His Asp Val Ser Asp Phe Gly His Arg Leu Leu Ala Tyr Leu Arg
        195                 200                 205

Ala Ala Asp Ala Gly Ala Glu Leu Leu Ile Leu Pro Ser Gly Gly Ser
    210                 215                 220

Ala Pro Thr Gly Asp His Pro Thr Pro His Pro Ser Thr Ser Arg
225                 230                 235
```

<210> SEQ ID NO 4
<211> LENGTH: 479
<212> TYPE: PRT
<213> ORGANISM: Mycobacterium tuberculosis

<400> SEQUENCE: 4

```
Met Ala Asp Phe Leu Thr Leu Ser Pro Glu Val Asn Ser Ala Arg Met
1               5                   10                  15

Tyr Ala Gly Gly Gly Pro Gly Ser Leu Ser Ala Ala Ala Ala Ala Trp
            20                  25                  30

Asp Glu Leu Ala Ala Glu Leu Trp Leu Ala Ala Ala Ser Phe Glu Ser
        35                  40                  45

Val Cys Ser Gly Leu Ala Asp Arg Trp Trp Gln Gly Pro Ser Ser Arg
    50                  55                  60

Met Met Ala Ala Gln Ala Ala Arg His Thr Gly Trp Leu Ala Ala Ala
65                  70                  75                  80

Ala Thr Gln Ala Glu Gly Ala Ala Ser Gln Ala Gln Thr Met Ala Leu
                85                  90                  95

Ala Tyr Glu Ala Ala Phe Ala Ala Thr Val His Pro Ala Leu Val Ala
            100                 105                 110

Ala Asn Arg Ala Leu Val Ala Trp Leu Ala Gly Ser Asn Val Phe Gly
        115                 120                 125

Gln Asn Thr Pro Ala Ile Ala Ala Ala Glu Ala Ile Tyr Glu Gln Met
    130                 135                 140
```

Trp Ala Gln Asp Val Val Ala Met Leu Asn Tyr His Ala Val Ala Ser
145 150 155 160

Ala Val Gly Ala Arg Leu Arg Pro Trp Gln Gln Leu Leu His Glu Leu
165 170 175

Pro Arg Arg Leu Gly Gly Glu His Ser Asp Ser Thr Asn Thr Glu Leu
180 185 190

Ala Asn Pro Ser Ser Thr Thr Thr Arg Ile Thr Val Pro Gly Ala Ser
195 200 205

Pro Val His Ala Ala Thr Leu Leu Pro Phe Ile Gly Arg Leu Leu Ala
210 215 220

Ala Arg Tyr Ala Glu Leu Asn Thr Ala Ile Gly Thr Asn Trp Phe Pro
225 230 235 240

Gly Thr Thr Pro Glu Val Val Ser Tyr Pro Ala Thr Ile Gly Val Leu
245 250 255

Ser Gly Ser Leu Gly Ala Val Asp Ala Asn Gln Ser Ile Ala Ile Gly
260 265 270

Gln Gln Met Leu His Asn Glu Ile Leu Ala Ala Thr Ala Ser Gly Gln
275 280 285

Pro Val Thr Val Ala Gly Leu Ser Met Gly Ser Met Val Ile Asp Arg
290 295 300

Glu Leu Ala Tyr Leu Ala Ile Asp Pro Asn Ala Pro Pro Ser Ser Ala
305 310 315 320

Leu Thr Phe Val Glu Leu Ala Gly Pro Glu Arg Gly Leu Ala Gln Thr
325 330 335

Tyr Leu Pro Val Gly Thr Thr Ile Pro Ile Ala Gly Tyr Thr Val Gly
340 345 350

Asn Ala Pro Glu Ser Gln Tyr Asn Thr Ser Val Val Tyr Ser Gln Tyr
355 360 365

Asp Ile Trp Ala Asp Pro Pro Asp Arg Pro Trp Asn Leu Leu Ala Gly
370 375 380

Ala Asn Ala Leu Met Gly Ala Ala Tyr Phe His Asp Leu Thr Ala Tyr
385 390 395 400

Ala Ala Pro Gln Gln Gly Ile Glu Ile Ala Ala Val Thr Ser Ser Leu
405 410 415

Gly Gly Thr Thr Thr Thr Tyr Met Ile Pro Ser Pro Thr Leu Pro Leu
420 425 430

Leu Leu Pro Leu Lys Gln Ile Gly Val Pro Asp Trp Ile Val Gly Gly
435 440 445

Leu Asn Asn Val Leu Lys Pro Leu Val Asp Ala Gly Tyr Ser Gln Tyr
450 455 460

Ala Pro Thr Ala Gly Pro Tyr Phe Ser His Gly Asn Leu Val Trp
465 470 475

<210> SEQ ID NO 5
<211> LENGTH: 394
<212> TYPE: PRT
<213> ORGANISM: Mycobacterium tuberculosis

<400> SEQUENCE: 5

Met Thr Leu Asp Val Pro Val Asn Gln Gly His Val Pro Pro Gly Ser
1 5 10 15

Val Ala Cys Cys Leu Val Gly Val Thr Ala Val Ala Asp Gly Ile Ala
20 25 30

Gly His Ser Leu Ser Asn Phe Gly Ala Leu Pro Pro Glu Ile Asn Ser

-continued

```
        35                  40                  45

Gly Arg Met Tyr Ser Gly Pro Gly Ser Gly Pro Leu Met Ala Ala Ala
    50                  55                  60

Ala Ala Trp Asp Gly Leu Ala Ala Glu Leu Ser Ser Ala Ala Thr Gly
65                  70                  75                  80

Tyr Gly Ala Ala Ile Ser Glu Leu Thr Asn Met Arg Trp Trp Ser Gly
                85                  90                  95

Pro Ala Ser Asp Ser Met Val Ala Ala Val Leu Pro Phe Val Gly Trp
            100                 105                 110

Leu Ser Thr Thr Ala Thr Leu Ala Glu Gln Ala Ala Met Gln Ala Arg
        115                 120                 125

Ala Ala Ala Ala Ala Phe Glu Ala Ala Phe Ala Met Thr Val Pro Pro
    130                 135                 140

Pro Ala Ile Ala Ala Asn Arg Thr Leu Leu Met Thr Leu Val Asp Thr
145                 150                 155                 160

Asn Trp Phe Gly Gln Asn Thr Pro Ala Ile Ala Thr Thr Glu Ser Gln
                165                 170                 175

Tyr Ala Glu Met Trp Ala Gln Asp Ala Ala Ala Met Tyr Gly Tyr Ala
            180                 185                 190

Ser Ala Ala Ala Pro Ala Thr Val Leu Thr Pro Phe Ala Pro Pro Pro
        195                 200                 205

Gln Thr Thr Asn Ala Thr Gly Leu Val Gly His Ala Thr Ala Val Ala
    210                 215                 220

Ala Leu Arg Gly Gln His Ser Trp Ala Ala Ala Ile Pro Trp Ser Asp
225                 230                 235                 240

Ile Gln Lys Tyr Trp Met Met Phe Leu Gly Ala Leu Ala Thr Ala Glu
                245                 250                 255

Gly Phe Ile Tyr Asp Ser Gly Gly Leu Thr Leu Asn Ala Leu Gln Phe
            260                 265                 270

Val Gly Gly Met Leu Trp Ser Thr Ala Leu Ala Glu Ala Gly Ala Ala
        275                 280                 285

Glu Ala Ala Ala Gly Ala Gly Gly Ala Ala Gly Trp Ser Ala Trp Ser
    290                 295                 300

Gln Leu Gly Ala Gly Pro Val Ala Ala Ser Ala Thr Leu Ala Ala Lys
305                 310                 315                 320

Ile Gly Pro Met Ser Val Pro Pro Gly Trp Ser Ala Pro Pro Ala Thr
                325                 330                 335

Pro Gln Ala Gln Thr Val Ala Arg Ser Ile Pro Gly Ile Arg Ser Ala
            340                 345                 350

Ala Glu Ala Ala Glu Thr Ser Val Leu Leu Arg Gly Ala Pro Thr Pro
        355                 360                 365

Gly Arg Ser Arg Ala Ala His Met Gly Arg Arg Tyr Gly Arg Arg Leu
    370                 375                 380

Thr Val Met Ala Asp Arg Pro Asn Val Gly
385                 390


<210> SEQ ID NO 6
<211> LENGTH: 391
<212> TYPE: PRT
<213> ORGANISM: Mycobacterium tuberculosis

<400> SEQUENCE: 6

Met Asp Phe Gly Ala Leu Pro Pro Glu Ile Asn Ser Ala Arg Met Tyr
1               5                   10                  15
```

-continued

```
Ala Gly Ala Gly Ala Gly Pro Met Met Ala Ala Gly Ala Ala Trp Asn
            20                  25                  30

Gly Leu Ala Ala Glu Leu Gly Thr Thr Ala Ala Ser Tyr Glu Ser Val
        35                  40                  45

Ile Thr Arg Leu Thr Thr Glu Ser Trp Met Gly Pro Ala Ser Met Ala
    50                  55                  60

Met Val Ala Ala Ala Gln Pro Tyr Leu Ala Trp Leu Thr Tyr Thr Ala
65                  70                  75                  80

Glu Ala Ala Ala His Ala Gly Ser Gln Ala Met Ala Ser Ala Ala Ala
                85                  90                  95

Tyr Glu Ala Ala Tyr Ala Met Thr Val Pro Pro Glu Val Val Ala Ala
            100                 105                 110

Asn Arg Ala Leu Leu Ala Ala Leu Val Ala Thr Asn Val Leu Gly Ile
        115                 120                 125

Asn Thr Pro Ala Ile Met Ala Thr Glu Ala Leu Tyr Ala Glu Met Trp
    130                 135                 140

Ala Gln Asp Ala Leu Ala Met Tyr Gly Tyr Ala Ala Ala Ser Gly Ala
145                 150                 155                 160

Ala Gly Met Leu Gln Pro Leu Ser Pro Pro Ser Gln Thr Thr Asn Pro
                165                 170                 175

Gly Gly Leu Ala Ala Gln Ser Ala Ala Val Gly Ser Ala Ala Ala Thr
            180                 185                 190

Ala Ala Val Asn Gln Val Ser Val Ala Asp Leu Ile Ser Ser Leu Pro
        195                 200                 205

Asn Ala Val Ser Gly Leu Ala Ser Pro Val Thr Ser Val Leu Asp Ser
    210                 215                 220

Thr Gly Leu Ser Gly Ile Ile Ala Asp Ile Asp Ala Leu Leu Ala Thr
225                 230                 235                 240

Pro Phe Val Ala Asn Ile Ile Asn Ser Ala Val Asn Thr Ala Ala Trp
                245                 250                 255

Tyr Val Asn Ala Ala Ile Pro Thr Ala Ile Phe Leu Ala Asn Ala Leu
            260                 265                 270

Asn Ser Gly Ala Pro Val Ala Ile Ala Glu Gly Ala Ile Glu Ala Ala
        275                 280                 285

Glu Gly Ala Ala Ser Ala Ala Ala Ala Gly Leu Ala Asp Ser Val Thr
    290                 295                 300

Pro Ala Gly Leu Gly Ala Ser Leu Gly Glu Ala Thr Leu Val Gly Arg
305                 310                 315                 320

Leu Ser Val Pro Ala Ala Trp Ser Thr Ala Ala Pro Ala Thr Thr Ala
                325                 330                 335

Gly Ala Thr Ala Leu Glu Gly Ser Gly Trp Thr Val Ala Ala Glu Glu
            340                 345                 350

Ala Gly Pro Val Thr Gly Met Met Pro Gly Met Ala Ser Ala Ala Lys
        355                 360                 365

Gly Thr Gly Ala Tyr Ala Gly Pro Arg Tyr Gly Phe Lys Pro Thr Val
    370                 375                 380

Met Pro Lys Gln Val Val Val
385                 390
```

<210> SEQ ID NO 7
<211> LENGTH: 552
<212> TYPE: PRT
<213> ORGANISM: Mycobacterium tuberculosis

<400> SEQUENCE: 7

-continued

```
Met Ala His Phe Ser Val Leu Pro Pro Glu Ile Asn Ser Leu Arg Met
1               5                   10                  15

Tyr Leu Gly Ala Gly Ser Ala Pro Met Leu Gln Ala Ala Ala Ala Trp
            20                  25                  30

Asp Gly Leu Ala Ala Glu Leu Gly Thr Ala Ala Ser Ser Phe Ser Ser
        35                  40                  45

Val Thr Thr Gly Leu Thr Gly Gln Ala Trp Gln Gly Pro Ala Ser Ala
    50                  55                  60

Ala Met Ala Ala Ala Ala Ala Pro Tyr Ala Gly Phe Leu Thr Thr Ala
65                  70                  75                  80

Ser Ala Gln Ala Gln Leu Ala Ala Gly Gln Ala Lys Ala Val Ala Ser
                85                  90                  95

Val Phe Glu Ala Ala Lys Ala Ala Ile Val Pro Pro Ala Ala Val Ala
            100                 105                 110

Ala Asn Arg Glu Ala Phe Leu Ala Leu Ile Arg Ser Asn Trp Leu Gly
        115                 120                 125

Leu Asn Ala Pro Trp Ile Ala Ala Val Glu Ser Leu Tyr Glu Glu Tyr
    130                 135                 140

Trp Ala Ala Asp Val Ala Ala Met Thr Gly Tyr His Ala Gly Ala Ser
145                 150                 155                 160

Gln Ala Ala Ala Gln Leu Pro Leu Pro Ala Gly Leu Gln Gln Phe Leu
                165                 170                 175

Asn Thr Leu Pro Asn Leu Gly Ile Gly Asn Gln Gly Asn Ala Asn Leu
            180                 185                 190

Gly Gly Gly Asn Thr Gly Ser Gly Asn Ile Gly Asn Gly Asn Lys Gly
        195                 200                 205

Ser Ser Asn Leu Gly Gly Gly Asn Ile Gly Asn Asn Asn Ile Gly Ser
    210                 215                 220

Gly Asn Arg Gly Ser Asp Asn Phe Gly Ala Gly Asn Val Gly Thr Gly
225                 230                 235                 240

Asn Ile Gly Phe Gly Asn Gln Gly Pro Ile Asp Val Asn Leu Leu Ala
                245                 250                 255

Thr Pro Gly Gln Asn Asn Val Gly Leu Gly Asn Ile Gly Asn Asn Asn
            260                 265                 270

Met Gly Phe Gly Asn Thr Gly Asp Ala Asn Thr Gly Gly Gly Asn Thr
        275                 280                 285

Gly Asn Gly Asn Ile Gly Gly Gly Asn Thr Gly Asn Asn Asn Phe Gly
    290                 295                 300

Phe Gly Asn Thr Gly Asn Asn Asn Ile Gly Ile Gly Leu Thr Gly Asn
305                 310                 315                 320

Asn Gln Met Gly Ile Asn Leu Ala Gly Leu Leu Asn Ser Gly Ser Gly
                325                 330                 335

Asn Ile Gly Ile Gly Asn Ser Gly Thr Asn Asn Ile Gly Leu Phe Asn
            340                 345                 350

Ser Gly Ser Gly Asn Ile Gly Val Phe Asn Thr Gly Ala Asn Thr Leu
        355                 360                 365

Val Pro Gly Asp Leu Asn Asn Leu Gly Val Gly Asn Ser Gly Asn Ala
    370                 375                 380

Asn Ile Gly Phe Gly Asn Ala Gly Val Leu Asn Thr Gly Phe Gly Asn
385                 390                 395                 400

Ala Ser Ile Leu Asn Thr Gly Leu Gly Asn Ala Gly Glu Leu Asn Thr
                405                 410                 415
```

-continued

```
Gly Phe Gly Asn Ala Gly Phe Val Asn Thr Gly Phe Asp Asn Ser Gly
            420                 425                 430

Asn Val Asn Thr Gly Asn Gly Asn Ser Gly Asn Ile Asn Thr Gly Ser
        435                 440                 445

Trp Asn Ala Gly Asn Val Asn Thr Gly Phe Gly Ile Ile Thr Asp Ser
    450                 455                 460

Gly Leu Thr Asn Ser Gly Phe Gly Asn Thr Gly Thr Asp Val Ser Gly
465                 470                 475                 480

Phe Phe Asn Thr Pro Thr Gly Pro Leu Ala Val Asp Val Ser Gly Phe
                485                 490                 495

Phe Asn Thr Ala Ser Gly Gly Thr Val Ile Asn Gly Gln Thr Ser Gly
            500                 505                 510

Ile Gly Asn Ile Gly Val Pro Gly Thr Leu Phe Gly Ser Val Arg Ser
        515                 520                 525

Gly Leu Asn Thr Gly Leu Phe Asn Met Gly Thr Ala Ile Ser Gly Leu
    530                 535                 540

Phe Asn Leu Arg Gln Leu Leu Gly
545                 550


<210> SEQ ID NO 8
<211> LENGTH: 561
<212> TYPE: PRT
<213> ORGANISM: Mycobacterium tuberculosis

<400> SEQUENCE: 8

Met Glu Tyr Leu Ile Ala Ala Gln Asp Val Leu Val Ala Ala Ala Ala
1               5                   10                  15

Asp Leu Glu Gly Ile Gly Ser Ala Leu Ala Ala Ala Asn Arg Ala Ala
            20                  25                  30

Glu Ala Pro Thr Thr Gly Leu Leu Ala Ala Gly Ala Asp Glu Val Ser
        35                  40                  45

Ala Ala Ile Ala Ser Leu Phe Ser Gly Asn Ala Gln Ala Tyr Gln Ala
    50                  55                  60

Leu Ser Ala Gln Ala Ala Ala Phe His Gln Gln Phe Val Arg Ala Leu
65                  70                  75                  80

Ser Ser Ala Ala Gly Ser Tyr Ala Ala Ala Glu Ala Ala Asn Ala Ser
                85                  90                  95

Pro Met Gln Ala Val Leu Asp Val Val Asn Gly Pro Thr Gln Leu Leu
            100                 105                 110

Leu Gly Arg Pro Leu Ile Gly Asp Gly Ala Asn Gly Gly Pro Gly Gln
        115                 120                 125

Asn Gly Gly Asp Gly Gly Leu Leu Tyr Gly Asn Gly Gly Asn Gly Gly
    130                 135                 140

Ser Ser Ser Thr Pro Gly Gln Pro Gly Gly Arg Gly Gly Ala Ala Gly
145                 150                 155                 160

Leu Ile Gly Asn Gly Gly Ala Gly Gly Ala Gly Gly Pro Gly Ala Asn
                165                 170                 175

Gly Gly Ala Gly Gly Asn Gly Gly Trp Leu Tyr Gly Asn Gly Gly Leu
            180                 185                 190

Gly Gly Asn Gly Gly Ala Ala Thr Gln Ile Gly Gly Asn Gly Gly Asn
        195                 200                 205

Gly Gly His Gly Gly Asn Ala Gly Leu Trp Gly Asn Gly Gly Ala Gly
    210                 215                 220

Gly Ala Gly Ala Ala Gly Ala Ala Gly Ala Asn Gly Gln Asn Pro Val
225                 230                 235                 240
```

-continued

Ser His Gln Val Thr His Ala Thr Asp Gly Ala Asp Gly Thr Thr Gly
245 250 255

Pro Asp Gly Asn Gly Thr Asp Ala Gly Ser Gly Ser Asn Ala Val Asn
260 265 270

Pro Gly Val Gly Gly Gly Ala Gly Gly Ile Gly Gly Asp Gly Thr Asn
275 280 285

Leu Gly Gln Thr Asp Val Ser Gly Gly Ala Gly Gly Asp Gly Gly Asp
290 295 300

Gly Ala Asn Phe Ala Ser Gly Gly Ala Gly Gly Asn Gly Gly Ala Ala
305 310 315 320

Gln Ser Gly Phe Gly Asp Ala Val Gly Gly Asn Gly Gly Ala Gly Gly
325 330 335

Asn Gly Gly Ala Gly Gly Gly Gly Gly Leu Gly Gly Ala Gly Gly Ser
340 345 350

Ala Asn Val Ala Asn Ala Gly Asn Ser Ile Gly Gly Asn Gly Gly Ala
355 360 365

Gly Gly Asn Gly Gly Ile Gly Ala Pro Gly Gly Ala Gly Gly Ala Gly
370 375 380

Gly Asn Ala Asn Gln Asp Asn Pro Pro Gly Gly Asn Ser Thr Gly Gly
385 390 395 400

Asn Gly Gly Ala Gly Gly Asp Gly Gly Val Gly Ala Ser Ala Asp Val
405 410 415

Gly Gly Ala Gly Gly Phe Gly Gly Ser Gly Gly Arg Gly Gly Leu Leu
420 425 430

Leu Gly Thr Gly Gly Ala Gly Gly Asp Gly Gly Val Gly Gly Asp Gly
435 440 445

Gly Ile Gly Ala Gln Gly Gly Ser Gly Gly Asn Gly Gly Asn Gly Gly
450 455 460

Ile Gly Ala Asp Gly Met Ala Asn Gln Asp Gly Asp Gly Gly Asp Gly
465 470 475 480

Gly Asn Gly Gly Asp Gly Gly Ala Gly Gly Ala Gly Gly Val Gly Gly
485 490 495

Asn Gly Gly Thr Gly Gly Ala Gly Gly Leu Phe Gly Gln Ser Gly Ser
500 505 510

Pro Gly Ser Gly Ala Ala Gly Gly Leu Gly Gly Ala Gly Gly Asn Gly
515 520 525

Gly Ala Gly Gly Gly Gly Gly Thr Gly Phe Asn Pro Gly Ala Pro Gly
530 535 540

Asp Pro Gly Thr Gln Gly Ala Thr Gly Ala Asn Gly Gln His Gly Leu
545 550 555 560

Asn

<210> SEQ ID NO 9
<211> LENGTH: 1538
<212> TYPE: PRT
<213> ORGANISM: Mycobacterium tuberculosis

<400> SEQUENCE: 9

Met Val Met Ser Leu Met Val Ala Pro Glu Leu Val Ala Ala Ala Ala
1 5 10 15

Ala Asp Leu Thr Gly Ile Gly Gln Ala Ile Ser Ala Ala Asn Ala Ala
20 25 30

Ala Ala Gly Pro Thr Thr Gln Val Leu Ala Ala Ala Gly Asp Glu Val
35 40 45

-continued

```
Ser Ala Ala Ile Ala Ala Leu Phe Gly Thr His Ala Gln Glu Tyr Gln
    50                  55                  60

Ala Leu Ser Ala Arg Val Ala Thr Phe His Glu Gln Phe Val Arg Ser
65                  70                  75                  80

Leu Thr Ala Ala Gly Ser Ala Tyr Ala Thr Ala Glu Ala Ala Asn Ala
                85                  90                  95

Ser Pro Leu Gln Ala Leu Glu Gln Gln Val Leu Gly Ala Ile Asn Ala
            100                 105                 110

Pro Thr Gln Leu Trp Leu Gly Arg Pro Leu Ile Gly Asp Gly Val His
        115                 120                 125

Gly Ala Pro Gly Thr Gly Gln Pro Gly Gly Ala Gly Gly Leu Leu Trp
    130                 135                 140

Gly Asn Gly Gly Asn Gly Gly Ser Gly Ala Ala Gly Gln Val Gly Gly
145                 150                 155                 160

Pro Gly Gly Ala Ala Gly Leu Phe Gly Asn Gly Gly Ser Gly Gly Ser
                165                 170                 175

Gly Gly Ala Gly Ala Ala Gly Gly Val Gly Gly Ser Gly Gly Trp Leu
            180                 185                 190

Asn Gly Asn Gly Gly Ala Gly Gly Ala Gly Gly Thr Gly Ala Asn Gly
        195                 200                 205

Gly Ala Gly Gly Asn Ala Trp Leu Phe Gly Ala Gly Gly Ser Gly Gly
    210                 215                 220

Ala Gly Thr Asn Gly Gly Val Gly Gly Ser Gly Gly Phe Val Tyr Gly
225                 230                 235                 240

Asn Gly Gly Ala Gly Gly Ile Gly Gly Ile Gly Gly Ile Gly Gly Asn
                245                 250                 255

Gly Gly Asp Ala Gly Leu Phe Gly Asn Gly Gly Ala Gly Gly Ala Gly
            260                 265                 270

Ala Ala Gly Leu Pro Gly Ala Ala Gly Leu Asn Gly Gly Asp Gly Ser
        275                 280                 285

Asp Gly Gly Asn Gly Gly Thr Gly Gly Asn Gly Gly Arg Gly Gly Leu
    290                 295                 300

Leu Val Gly Asn Gly Gly Ala Gly Gly Ala Gly Gly Val Gly Gly Asp
305                 310                 315                 320

Gly Gly Lys Gly Gly Ala Gly Asp Pro Ser Phe Ala Val Asn Asn Gly
                325                 330                 335

Ala Gly Gly Asn Gly Gly His Gly Gly Asn Pro Gly Val Gly Gly Ala
            340                 345                 350

Gly Gly Ala Gly Gly Leu Leu Ala Gly Ala His Gly Ala Ala Gly Ala
        355                 360                 365

Thr Pro Thr Ser Gly Gly Asn Gly Gly Asp Gly Gly Ile Gly Ala Thr
    370                 375                 380

Ala Asn Ser Pro Leu Gln Ala Gly Gly Ala Gly Gly Asn Gly Gly His
385                 390                 395                 400

Gly Gly Leu Val Gly Asn Gly Gly Thr Gly Gly Ala Gly Gly Ala Gly
                405                 410                 415

His Ala Gly Ser Thr Gly Ala Thr Gly Thr Ala Leu Gln Pro Thr Gly
            420                 425                 430

Gly Asn Gly Thr Asn Gly Gly Ala Gly Gly His Gly Gly Asn Gly Gly
        435                 440                 445

Asn Gly Gly Ala Gln His Gly Asp Gly Gly Val Gly Gly Lys Gly Gly
    450                 455                 460
```

-continued

```
Ala Gly Gly Ser Gly Gly Ala Gly Gly Asn Gly Phe Asp Ala Ala Thr
465                 470                 475                 480

Leu Gly Ser Pro Gly Ala Asp Gly Gly Met Gly Gly Asn Gly Gly Lys
                485                 490                 495

Gly Gly Asp Gly Gly Lys Ala Gly Asp Gly Gly Ala Gly Ala Ala Gly
            500                 505                 510

Asp Val Thr Leu Ala Val Asn Gln Gly Ala Gly Gly Asp Gly Gly Asn
        515                 520                 525

Gly Gly Glu Val Gly Val Gly Gly Lys Gly Gly Ala Gly Gly Val Ser
    530                 535                 540

Ala Asn Pro Ala Leu Asn Gly Ser Ala Gly Ala Asn Gly Thr Ala Pro
545                 550                 555                 560

Thr Ser Gly Gly Asn Gly Gly Asn Gly Gly Ala Gly Ala Thr Pro Thr
                565                 570                 575

Val Ala Gly Glu Asn Gly Gly Ala Gly Gly Asn Gly Gly His Gly Gly
            580                 585                 590

Ser Val Gly Asn Gly Gly Ala Gly Gly Ala Gly Gly Asn Gly Val Ala
        595                 600                 605

Gly Thr Gly Leu Ala Leu Asn Gly Gly Asn Gly Gly Asn Gly Gly Ile
    610                 615                 620

Gly Gly Asn Gly Gly Ser Ala Ala Gly Thr Gly Gly Asp Gly Gly Lys
625                 630                 635                 640

Gly Gly Asn Gly Gly Ala Gly Ala Asn Gly Gln Asp Phe Ser Ala Ser
                645                 650                 655

Ala Asn Gly Ala Asn Gly Gly Gln Gly Gly Asn Gly Gly Asn Gly Gly
            660                 665                 670

Ile Gly Gly Lys Gly Gly Asp Ala Phe Ala Thr Phe Ala Lys Ala Gly
        675                 680                 685

Asn Gly Gly Ala Gly Gly Asn Gly Gly Asn Val Gly Val Ala Gly Gln
    690                 695                 700

Gly Gly Ala Gly Gly Lys Gly Ala Ile Pro Ala Met Lys Gly Ala Thr
705                 710                 715                 720

Gly Ala Asp Gly Thr Ala Pro Thr Ser Gly Gly Asp Gly Gly Asn Gly
                725                 730                 735

Gly Asn Gly Ala Ser Pro Thr Val Ala Gly Gly Asn Gly Gly Asp Gly
            740                 745                 750

Gly Lys Gly Gly Ser Gly Gly Asn Val Gly Asn Gly Gly Asn Gly Gly
        755                 760                 765

Ala Gly Gly Asn Gly Ala Ala Gly Gln Ala Gly Thr Pro Gly Pro Thr
    770                 775                 780

Ser Gly Asp Ser Gly Thr Ser Gly Thr Asp Gly Gly Ala Gly Gly Asn
785                 790                 795                 800

Gly Gly Ala Gly Gly Ala Gly Gly Thr Leu Ala Gly His Gly Gly Asn
                805                 810                 815

Gly Gly Lys Gly Gly Asn Gly Gly Gln Gly Gly Ile Gly Gly Ala Gly
            820                 825                 830

Glu Arg Gly Ala Asp Gly Ala Gly Pro Asn Ala Asn Gly Ala Asn Gly
        835                 840                 845

Glu Asn Gly Gly Ser Gly Gly Asn Gly Gly Asp Gly Gly Ala Gly Gly
    850                 855                 860

Asn Gly Gly Ala Gly Gly Lys Ala Gln Ala Ala Gly Tyr Thr Asp Gly
865                 870                 875                 880

Ala Thr Gly Thr Gly Gly Asp Gly Gly Asn Gly Gly Asp Gly Gly Lys
```

-continued

```
                885                 890                 895

Ala Gly Asp Gly Gly Ala Gly Glu Asn Gly Leu Asn Ser Gly Ala Met
            900                 905                 910

Leu Pro Gly Gly Gly Thr Val Gly Asn Pro Gly Thr Gly Gly Asn Gly
        915                 920                 925

Gly Asn Gly Gly Asn Ala Gly Val Gly Gly Thr Gly Gly Lys Ala Gly
    930                 935                 940

Thr Gly Ser Leu Thr Gly Leu Asp Gly Thr Asp Gly Ile Thr Pro Asn
945                 950                 955                 960

Gly Gly Asn Gly Gly Asn Gly Gly Asn Gly Gly Lys Gly Gly Thr Ala
                965                 970                 975

Gly Asn Gly Ser Gly Ala Ala Gly Gly Asn Gly Gly Asn Gly Gly Ser
            980                 985                 990

Gly Leu Asn Gly Gly Asp Ala Gly  Asn Gly Gly Asn Gly  Gly Gly Ala
        995                 1000                1005

Leu Asn  Gln Ala Gly Phe Phe  Gly Thr Gly Gly Lys  Gly Gly Asn
    1010                 1015                 1020

Gly Gly  Asn Gly Gly Ala Gly  Met Ile Asn Gly Gly  Leu Gly Gly
    1025                 1030                 1035

Phe Gly  Gly Ala Gly Gly Gly  Gly Ala Val Asp Val  Ala Ala Thr
    1040                 1045                 1050

Thr Gly  Gly Ala Gly Gly Asn  Gly Gly Ala Gly Gly  Phe Ala Ser
    1055                 1060                 1065

Thr Gly  Leu Gly Gly Pro Gly  Gly Ala Gly Gly Pro  Gly Gly Ala
    1070                 1075                 1080

Gly Asp  Phe Ala Ser Gly Val  Gly Gly Val Gly Gly  Ala Gly Gly
    1085                 1090                 1095

Asp Gly  Gly Ala Gly Gly Val  Gly Gly Phe Gly Gly  Gln Gly Gly
    1100                 1105                 1110

Ile Gly  Gly Glu Gly Arg Thr  Gly Gly Asn Gly Gly  Ser Gly Gly
    1115                 1120                 1125

Asp Gly  Gly Gly Gly Ile Ser  Leu Gly Gly Asn Gly  Gly Leu Gly
    1130                 1135                 1140

Gly Asn  Gly Gly Val Ser Glu  Thr Gly Phe Gly Gly  Ala Gly Gly
    1145                 1150                 1155

Asn Gly  Gly Tyr Gly Gly Pro  Gly Gly Pro Glu Gly  Asn Gly Gly
    1160                 1165                 1170

Leu Gly  Gly Asn Gly Gly Ala  Gly Gly Asn Gly Gly  Val Ser Thr
    1175                 1180                 1185

Thr Gly  Gly Asp Gly Gly Ala  Gly Gly Lys Gly Gly  Asn Gly Gly
    1190                 1195                 1200

Asp Gly  Gly Asn Val Gly Leu  Gly Gly Asp Ala Gly  Ser Gly Gly
    1205                 1210                 1215

Ala Gly  Gly Asn Gly Gly Ile  Gly Thr Asp Ala Gly  Gly Ala Gly
    1220                 1225                 1230

Gly Ala  Gly Gly Ala Gly Gly  Asn Gly Gly Ser Ser  Lys Ser Thr
    1235                 1240                 1245

Thr Thr  Gly Asn Ala Gly Ser  Gly Gly Ala Gly Gly  Asn Gly Gly
    1250                 1255                 1260

Thr Gly  Leu Asn Gly Ala Gly  Gly Ala Gly Gly Ala  Gly Gly Asn
    1265                 1270                 1275

Ala Gly  Val Ala Gly Val Ser  Phe Gly Asn Ala Val  Gly Gly Asp
    1280                 1285                 1290
```

```
Gly Gly Asn Gly Gly Asn Gly Gly His Gly Gly Asp Gly Thr Thr
    1295                1300                1305

Gly Gly Ala Gly Gly Lys Gly Gly Asn Gly Ser Ser Gly Ala Ala
    1310                1315                1320

Ser Gly Ser Gly Val Val Asn Val Thr Ala Gly His Gly Gly Asn
    1325                1330                1335

Gly Gly Asn Gly Gly Asn Gly Gly Asn Gly Ser Ala Gly Ala Gly
    1340                1345                1350

Gly Gln Gly Gly Ala Gly Gly Ser Ala Gly Asn Gly Gly His Gly
    1355                1360                1365

Gly Gly Ala Thr Gly Gly Asp Gly Gly Asn Gly Gly Asn Gly Gly
    1370                1375                1380

Asn Ser Gly Asn Ser Thr Gly Val Ala Gly Leu Ala Gly Gly Ala
    1385                1390                1395

Ala Gly Ala Gly Gly Asn Gly Gly Gly Thr Ser Ser Ala Ala Gly
    1400                1405                1410

His Gly Gly Ser Gly Gly Ser Gly Gly Ser Gly Thr Thr Gly Gly
    1415                1420                1425

Ala Gly Ala Ala Gly Gly Asn Gly Gly Ala Gly Ala Gly Gly Gly
    1430                1435                1440

Ser Leu Ser Thr Gly Gln Ser Gly Gly Pro Arg Arg Gln Arg Trp
    1445                1450                1455

Cys Arg Trp Gln Arg Arg Arg Trp Leu Gly Arg Gln Arg Arg Arg
    1460                1465                1470

Arg Trp Cys Arg Trp Gln Arg Arg Cys Arg Arg Gln Arg Trp Arg
    1475                1480                1485

Trp Arg Cys Arg Gln Arg Arg Leu Arg Arg Gln Trp Arg Gln Gly
    1490                1495                1500

Arg Arg Arg Cys Arg Pro Trp Leu His Arg Arg Arg Gly Arg Gln
    1505                1510                1515

Gly Arg Arg Trp Arg Gln Arg Arg Phe Gln Gln Arg Gln Arg Ser
    1520                1525                1530

Arg Trp Gln Arg Arg
    1535
```

<210> SEQ ID NO 10
<211> LENGTH: 423
<212> TYPE: PRT
<213> ORGANISM: Mycobacterium tuberculosis

<400> SEQUENCE: 10

```
Val Ile Gln Thr Cys Glu Val Glu Leu Arg Trp Arg Ala Ser Gln Leu
1               5                   10                  15

Thr Leu Ala Ile Ala Thr Cys Ala Gly Val Ala Leu Ala Ala Ala Val
            20                  25                  30

Val Ala Gly Arg Trp Gln Leu Ile Ala Phe Ala Ala Pro Leu Leu Gly
        35                  40                  45

Val Leu Cys Ser Ile Ser Trp Gln Arg Pro Val Pro Val Ile Gln Val
    50                  55                  60

His Gly Asp Pro Asp Ser Gln Arg Cys Phe Glu Asn Glu His Val Arg
65                  70                  75                  80

Val Thr Val Trp Val Thr Thr Glu Ser Val Asp Ala Ala Val Glu Leu
                85                  90                  95

Thr Val Ser Ala Leu Ala Gly Met Gln Phe Glu Ala Leu Glu Ser Val
```

-continued

```
            100                 105                 110

Ser Arg Arg Thr Thr Thr Val Ser Ala Val Ala Gln Arg Trp Gly Arg
        115                 120                 125

Tyr Pro Ile Arg Ala Arg Val Ala Val Val Ala Arg Gly Gly Leu Leu
    130                 135                 140

Met Gly Ala Gly Thr Val Asp Ala Ala Glu Ile Val Val Phe Pro Leu
145                 150                 155                 160

Thr Pro Pro Gln Ser Thr Pro Leu Pro Gln Thr Glu Leu Leu Asp Arg
                165                 170                 175

Leu Gly Ala His Leu Thr Arg His Val Gly Pro Gly Val Glu Tyr Ala
            180                 185                 190

Asp Ile Arg Pro Tyr Val Pro Gly Asp Gln Leu Arg Ala Val Asn Trp
        195                 200                 205

Val Val Ser Ala Arg Arg Gly Arg Leu His Val Thr Arg Arg Leu Thr
    210                 215                 220

Asp Arg Ala Ala Asp Val Val Val Leu Ile Asp Met Tyr Arg Gln Pro
225                 230                 235                 240

Ala Gly Pro Ala Thr Glu Ala Thr Glu Arg Val Val Arg Gly Ala Ala
                245                 250                 255

Gln Val Val Gln Thr Ala Leu Arg Asn Gly Asp Arg Ala Gly Ile Val
            260                 265                 270

Ala Leu Gly Gly Asn Arg Pro Arg Trp Leu Gly Ala Asp Ile Gly Gln
        275                 280                 285

Arg Gln Phe Tyr Arg Val Leu Asp Thr Val Leu Gly Ala Gly Glu Gly
    290                 295                 300

Phe Glu Asn Thr Thr Gly Thr Leu Ala Pro Arg Ala Ala Val Pro Ala
305                 310                 315                 320

Gly Ala Val Val Ile Ala Phe Ser Thr Leu Leu Asp Thr Glu Phe Ala
                325                 330                 335

Leu Ala Leu Ile Asp Leu Arg Lys Arg Gly His Val Val Val Ala Val
            340                 345                 350

Asp Val Leu Asp Ser Cys Pro Leu Gln Asp Gln Leu Asp Pro Leu Val
        355                 360                 365

Val Arg Met Trp Ala Leu Gln Arg Ser Ala Met Tyr Arg Asp Met Ala
    370                 375                 380

Thr Ile Gly Val Asp Val Leu Ser Trp Pro Ala Asp His Ser Leu Gln
385                 390                 395                 400

Gln Ser Met Gly Ala Leu Pro Asn Arg Arg Arg Arg Gly Arg Gly Arg
                405                 410                 415

Ala Ser Arg Ala Arg Leu Pro
            420


<210> SEQ ID NO 11
<211> LENGTH: 340
<212> TYPE: PRT
<213> ORGANISM: Mycobacterium tuberculosis

<400> SEQUENCE: 11

Val Asn Arg Arg Ile Leu Thr Leu Met Val Ala Leu Val Pro Ile Val
1               5                   10                  15

Val Phe Gly Val Leu Leu Ala Val Val Thr Val Pro Phe Val Ala Leu
            20                  25                  30

Gly Pro Gly Pro Thr Phe Asp Thr Leu Gly Glu Ile Asp Gly Lys Gln
        35                  40                  45
```

-continued

Val Val Gln Ile Val Gly Thr Gln Thr Tyr Pro Thr Ser Gly His Leu
50 55 60

Asn Met Thr Thr Val Ser Gln Arg Asp Gly Leu Thr Leu Gly Glu Ala
65 70 75 80

Leu Ala Leu Trp Leu Ser Gly Gln Glu Gln Leu Met Pro Arg Asp Leu
85 90 95

Val Tyr Pro Pro Gly Lys Ser Arg Glu Glu Ile Glu Asn Asp Asn Ala
100 105 110

Ala Asp Phe Lys Arg Ser Glu Ala Ala Ala Glu Tyr Ala Ala Leu Gly
115 120 125

Tyr Leu Lys Tyr Pro Lys Ala Val Thr Val Ala Ser Val Met Asp Pro
130 135 140

Gly Pro Ser Val Asp Lys Leu Gln Ala Gly Asp Ala Ile Asp Ala Val
145 150 155 160

Asp Gly Thr Pro Val Gly Asn Leu Asp Gln Phe Thr Ala Leu Leu Lys
165 170 175

Asn Thr Lys Pro Gly Gln Glu Val Thr Ile Asp Phe Arg Arg Lys Asn
180 185 190

Glu Pro Pro Gly Ile Ala Gln Ile Thr Leu Gly Lys Asn Lys Asp Arg
195 200 205

Asp Gln Gly Val Leu Gly Ile Glu Val Val Asp Ala Pro Trp Ala Pro
210 215 220

Phe Ala Val Asp Phe His Leu Ala Asn Val Gly Gly Pro Ser Ala Gly
225 230 235 240

Leu Met Phe Ser Leu Ala Val Val Asp Lys Leu Thr Ser Gly His Leu
245 250 255

Val Gly Ser Thr Phe Val Ala Gly Thr Gly Thr Ile Ala Val Asp Gly
260 265 270

Lys Val Gly Gln Ile Gly Gly Ile Thr His Lys Met Ala Ala Ala Arg
275 280 285

Ala Ala Gly Ala Thr Val Phe Leu Val Pro Ala Lys Asn Cys Tyr Glu
290 295 300

Ala Ser Ser Asp Ser Pro Pro Gly Leu Lys Leu Val Lys Val Glu Thr
305 310 315 320

Leu Ser Gln Ala Val Asp Ala Leu His Ala Met Thr Ser Gly Ser Pro
325 330 335

Thr Pro Ser Cys
340

<210> SEQ ID NO 12
<211> LENGTH: 923
<212> TYPE: PRT
<213> ORGANISM: Mycobacterium tuberculosis

<400> SEQUENCE: 12

Met Ser Phe Val Val Thr Ala Pro Pro Val Leu Ala Ser Ala Ala Ser
1 5 10 15

Asp Leu Gly Gly Ile Ala Ser Met Ile Ser Glu Ala Asn Ala Met Ala
20 25 30

Ala Val Arg Thr Thr Ala Leu Ala Pro Ala Ala Ala Asp Glu Val Ser
35 40 45

Ala Ala Ile Ala Ala Leu Phe Ser Ser Tyr Ala Arg Asp Tyr Gln Thr
50 55 60

Leu Ser Val Gln Val Thr Ala Phe His Val Gln Phe Ala Gln Thr Leu
65 70 75 80

```
Thr Asn Ala Gly Gln Leu Tyr Ala Val Val Asp Val Gly Asn Gly Val
                85                  90                  95

Leu Leu Lys Thr Glu Gln Gln Val Leu Gly Val Ile Asn Ala Pro Thr
            100                 105                 110

Gln Thr Leu Val Gly Arg Pro Leu Ile Gly Asp Gly Thr His Gly Ala
        115                 120                 125

Pro Gly Thr Gly Gln Asn Gly Gly Ala Gly Gly Ile Leu Trp Gly Asn
    130                 135                 140

Gly Gly Asn Gly Gly Ser Gly Ala Pro Gly Gln Pro Gly Gly Arg Gly
145                 150                 155                 160

Gly Asp Ala Gly Leu Phe Gly His Gly Gly His Gly Gly Val Gly Gly
                165                 170                 175

Pro Gly Ile Ala Gly Ala Ala Gly Thr Ala Gly Leu Pro Gly Gly Asn
            180                 185                 190

Gly Ala Asn Gly Gly Ser Gly Gly Ile Gly Gly Ala Gly Gly Ala Gly
        195                 200                 205

Gly Asn Gly Gly Leu Leu Phe Gly Asn Gly Gly Ala Gly Gly Gln Gly
    210                 215                 220

Gly Ser Gly Gly Leu Gly Gly Ser Gly Gly Thr Gly Gly Ala Gly Met
225                 230                 235                 240

Ala Ala Gly Pro Ala Gly Gly Thr Gly Gly Ile Gly Gly Ile Gly Gly
                245                 250                 255

Ile Gly Gly Ala Gly Gly Val Gly Gly His Gly Ser Ala Leu Phe Gly
            260                 265                 270

His Gly Gly Ile Asn Gly Asp Gly Gly Thr Gly Gly Met Gly Gly Gln
        275                 280                 285

Gly Gly Ala Gly Gly Asn Gly Trp Ala Ala Glu Gly Ile Thr Val Gly
    290                 295                 300

Ile Gly Glu Gln Gly Gly Gln Gly Gly Asp Gly Gly Ala Gly Gly Ala
305                 310                 315                 320

Gly Gly Ile Gly Gly Ser Ala Gly Gly Ile Gly Gly Ser Gln Gly Ala
                325                 330                 335

Gly Gly His Gly Gly Asp Gly Gly Gln Gly Gly Ala Gly Gly Ser Gly
            340                 345                 350

Gly Val Gly Gly Gly Gly Ala Gly Ala Gly Gly Asp Gly Gly Ala Gly
        355                 360                 365

Gly Ile Gly Gly Thr Gly Gly Asn Gly Ser Ile Gly Gly Ala Ala Gly
    370                 375                 380

Asn Gly Gly Asn Gly Gly Arg Gly Gly Ala Gly Gly Met Ala Thr Ala
385                 390                 395                 400

Gly Ser Asp Gly Gly Asn Gly Gly Gly Gly Gly Asn Gly Gly Val Gly
                405                 410                 415

Val Gly Ser Ala Gly Gly Ala Gly Gly Thr Gly Gly Asp Gly Gly Ala
            420                 425                 430

Ala Gly Ala Gly Gly Ala Pro Gly His Gly Tyr Phe Gln Gln Pro Ala
        435                 440                 445

Pro Gln Gly Leu Pro Ile Gly Thr Gly Gly Thr Gly Gly Glu Gly Gly
    450                 455                 460

Ala Gly Gly Ala Gly Gly Asp Gly Gly Gln Gly Asp Ile Gly Phe Asp
465                 470                 475                 480

Gly Gly Arg Gly Gly Asp Gly Gly Pro Gly Gly Gly Gly Gly Ala Gly
                485                 490                 495
```

-continued

```
Gly Asp Gly Ser Gly Thr Phe Asn Ala Gln Ala Asn Asn Gly Gly Asp
            500                 505                 510

Gly Gly Ala Gly Gly Val Gly Gly Ala Gly Gly Thr Gly Gly Thr Gly
        515                 520                 525

Gly Val Gly Ala Asp Gly Gly Arg Gly Gly Asp Ser Gly Arg Gly Gly
    530                 535                 540

Asp Gly Gly Asn Ala Gly His Gly Gly Ala Ala Gln Phe Ser Gly Arg
545                 550                 555                 560

Gly Ala Tyr Gly Gly Glu Gly Gly Ser Gly Gly Ala Gly Gly Asn Ala
                565                 570                 575

Gly Gly Ala Gly Thr Gly Gly Thr Ala Gly Ser Gly Gly Ala Gly Gly
            580                 585                 590

Phe Gly Gly Asn Gly Ala Asp Gly Gly Asn Gly Gly Asn Gly Gly Asn
        595                 600                 605

Gly Gly Phe Gly Gly Ile Asn Gly Thr Phe Gly Thr Asn Gly Ala Gly
    610                 615                 620

Gly Thr Gly Gly Leu Gly Thr Leu Leu Gly Gly His Asn Gly Asn Ile
625                 630                 635                 640

Gly Leu Asn Gly Ala Thr Gly Gly Ile Gly Ser Thr Thr Leu Thr Asn
                645                 650                 655

Ala Thr Val Pro Leu Gln Leu Val Asn Thr Thr Glu Pro Val Val Phe
            660                 665                 670

Ile Ser Leu Asn Gly Gly Gln Met Val Pro Val Leu Leu Asp Thr Gly
        675                 680                 685

Ser Thr Gly Leu Val Met Asp Ser Gln Phe Leu Thr Gln Asn Phe Gly
    690                 695                 700

Pro Val Ile Gly Thr Gly Thr Ala Gly Tyr Ala Gly Gly Leu Thr Tyr
705                 710                 715                 720

Asn Tyr Asn Thr Tyr Ser Thr Thr Val Asp Phe Gly Asn Gly Leu Leu
                725                 730                 735

Thr Leu Pro Thr Ser Val Asn Val Val Thr Ser Ser Ser Pro Gly Thr
            740                 745                 750

Leu Gly Asn Phe Leu Ser Arg Ser Gly Ala Val Gly Val Leu Gly Ile
        755                 760                 765

Gly Pro Asn Asn Gly Phe Pro Gly Thr Ser Ser Ile Val Thr Ala Met
    770                 775                 780

Pro Gly Leu Leu Asn Asn Gly Val Leu Ile Asp Glu Ser Ala Gly Ile
785                 790                 795                 800

Leu Gln Phe Gly Pro Asn Thr Leu Thr Gly Gly Ile Thr Ile Ser Gly
                805                 810                 815

Ala Pro Ile Ser Thr Val Ala Val Gln Ile Asp Asn Gly Pro Leu Gln
            820                 825                 830

Gln Ala Pro Val Met Phe Asp Ser Gly Gly Ile Asn Gly Thr Ile Pro
        835                 840                 845

Ser Ala Leu Ala Ser Leu Pro Ser Gly Gly Phe Val Pro Ala Gly Thr
    850                 855                 860

Thr Ile Ser Val Tyr Thr Ser Asp Gly Gln Thr Leu Leu Tyr Ser Tyr
865                 870                 875                 880

Thr Thr Thr Ala Thr Asn Thr Pro Phe Val Thr Ser Gly Gly Val Met
                885                 890                 895

Asn Thr Gly His Val Pro Phe Ala Gln Gln Pro Ile Tyr Val Ser Tyr
            900                 905                 910

Ser Pro Thr Ala Ile Gly Thr Thr Thr Phe Asn
```

915 920

<210> SEQ ID NO 13
<211> LENGTH: 332
<212> TYPE: PRT
<213> ORGANISM: Mycobacterium tuberculosis

<400> SEQUENCE: 13

Met Thr His Asp His Ala His Ser Arg Gly Val Pro Ala Met Ile Lys
1 5 10 15

Glu Ile Phe Ala Pro His Ser His Asp Ala Ala Asp Ser Val Asp Asp
20 25 30

Thr Leu Glu Ser Thr Ala Ala Gly Ile Arg Thr Val Lys Ile Ser Leu
35 40 45

Leu Val Leu Gly Leu Thr Ala Leu Ile Gln Ile Val Ile Val Val Met
50 55 60

Ser Gly Ser Val Ala Leu Ala Ala Asp Thr Ile His Asn Phe Ala Asp
65 70 75 80

Ala Leu Thr Ala Val Pro Leu Trp Ile Ala Phe Ala Leu Gly Ala Lys
85 90 95

Pro Ala Thr Arg Arg Tyr Thr Tyr Gly Phe Gly Arg Val Glu Asp Leu
100 105 110

Ala Gly Ser Phe Val Val Ala Met Ile Thr Met Ser Ala Ile Ile Ala
115 120 125

Gly Tyr Glu Ala Ile Ala Arg Leu Ile His Pro Gln Gln Ile Glu His
130 135 140

Val Gly Trp Val Ala Leu Ala Gly Leu Val Gly Phe Ile Gly Asn Glu
145 150 155 160

Trp Val Ala Leu Tyr Arg Ile Arg Val Gly His Arg Ile Gly Ser Ala
165 170 175

Ala Leu Ile Ala Asp Gly Leu His Ala Arg Thr Asp Gly Phe Thr Ser
180 185 190

Leu Ala Val Leu Cys Ser Ala Gly Gly Val Ala Leu Gly Phe Pro Leu
195 200 205

Ala Asp Pro Ile Val Gly Leu Leu Ile Thr Ala Ala Ile Leu Ala Val
210 215 220

Leu Arg Thr Ala Ala Arg Asp Val Phe Arg Arg Leu Leu Asp Gly Val
225 230 235 240

Asp Pro Ala Met Val Asp Ala Ala Glu Gln Ala Leu Ala Ala Arg Pro
245 250 255

Gly Val Gln Ala Val Arg Ser Val Arg Met Arg Trp Ile Gly His Arg
260 265 270

Leu His Ala Asp Ala Glu Leu Asp Val Asp Pro Ala Leu Asp Leu Ala
275 280 285

Gln Ala His Arg Ile Ala His Asp Ala Glu His Glu Leu Thr His Thr
290 295 300

Val Pro Lys Leu Thr Thr Ala Leu Ile His Ala Tyr Pro Ala Glu His
305 310 315 320

Gly Ser Ser Ile Pro Asp Arg Gly Arg Thr Val Glu
325 330

<210> SEQ ID NO 14
<211> LENGTH: 615
<212> TYPE: PRT
<213> ORGANISM: Mycobacterium tuberculosis

<400> SEQUENCE: 14

Val Val Asn Phe Ser Val Leu Pro Pro Glu Ile Asn Ser Gly Arg Met
1               5                   10                  15

Phe Phe Gly Ala Gly Ser Gly Pro Met Leu Ala Ala Ala Ala Ala Trp
            20                  25                  30

Asp Gly Leu Ala Ala Glu Leu Gly Leu Ala Ala Glu Ser Phe Gly Leu
        35                  40                  45

Val Thr Ser Gly Leu Ala Gly Gly Ser Gly Gln Ala Trp Gln Gly Ala
    50                  55                  60

Ala Ala Ala Ala Met Val Val Ala Ala Ala Pro Tyr Ala Gly Trp Leu
65                  70                  75                  80

Ala Ala Ala Ala Ala Arg Ala Gly Gly Ala Ala Val Gln Ala Lys Ala
                85                  90                  95

Val Ala Gly Ala Phe Glu Ala Ala Arg Ala Ala Met Val Asp Pro Val
            100                 105                 110

Val Val Ala Ala Asn Arg Ser Ala Phe Val Gln Leu Val Leu Ser Asn
        115                 120                 125

Val Phe Gly Gln Asn Ala Pro Ala Ile Ala Ala Ala Glu Ala Thr Tyr
    130                 135                 140

Glu Gln Met Trp Ala Ala Asp Val Ala Ala Met Val Gly Tyr His Gly
145                 150                 155                 160

Gly Ala Ser Ala Ala Ala Ala Ala Leu Ala Pro Trp Gln Gln Ala Val
                165                 170                 175

Pro Gly Leu Ser Gly Leu Leu Gly Gly Ala Ala Asn Ala Pro Ala Ala
            180                 185                 190

Ala Ala Gln Gly Ala Ala Gln Gly Leu Ala Glu Leu Thr Leu Asn Leu
        195                 200                 205

Gly Val Gly Asn Ile Gly Ser Leu Asn Leu Gly Ser Gly Asn Ile Gly
    210                 215                 220

Gly Thr Asn Val Gly Ser Gly Asn Val Gly Gly Thr Asn Leu Gly Ser
225                 230                 235                 240

Gly Asn Tyr Gly Ser Leu Asn Trp Gly Ser Gly Asn Thr Gly Thr Gly
                245                 250                 255

Asn Ala Gly Ser Gly Asn Thr Gly Asp Tyr Asn Pro Gly Ser Gly Asn
            260                 265                 270

Phe Gly Ser Gly Asn Phe Gly Ser Gly Asn Ile Gly Ser Leu Asn Val
        275                 280                 285

Gly Ser Gly Asn Phe Gly Thr Leu Asn Leu Ala Asn Gly Asn Asn Gly
    290                 295                 300

Asp Val Asn Phe Gly Gly Gly Asn Thr Gly Asp Phe Asn Phe Gly Gly
305                 310                 315                 320

Gly Asn Asn Gly Thr Leu Asn Phe Gly Phe Gly Asn Thr Gly Ser Gly
                325                 330                 335

Asn Phe Gly Phe Gly Asn Thr Gly Asn Asn Asn Ile Gly Ile Gly Leu
            340                 345                 350

Thr Gly Asp Gly Gln Ile Gly Ile Gly Gly Leu Asn Ser Gly Thr Gly
        355                 360                 365

Asn Ile Gly Phe Gly Asn Ser Gly Asn Asn Asn Ile Gly Phe Phe Asn
    370                 375                 380

Ser Gly Asp Gly Asn Ile Gly Phe Phe Asn Ser Gly Asp Gly Asn Thr
385                 390                 395                 400

Gly Phe Gly Asn Ala Gly Asn Ile Asn Thr Gly Phe Trp Asn Ala Gly
                405                 410                 415

Asn Leu Asn Thr Gly Phe Gly Ser Ala Gly Asn Gly Asn Val Gly Ile
420 425 430

Phe Asp Gly Gly Asn Ser Asn Ser Gly Ser Phe Asn Val Gly Phe Gln
435 440 445

Asn Thr Gly Phe Gly Asn Ser Gly Ala Gly Asn Thr Gly Phe Phe Asn
450 455 460

Ala Gly Asp Ser Asn Thr Gly Phe Ala Asn Ala Gly Asn Val Asn Thr
465 470 475 480

Gly Phe Phe Asn Gly Gly Asp Ile Asn Thr Gly Gly Phe Asn Gly Gly
485 490 495

Asn Val Asn Thr Gly Phe Gly Ser Ala Leu Thr Gln Ala Gly Ala Asn
500 505 510

Ser Gly Phe Gly Asn Leu Gly Thr Gly Asn Ser Gly Trp Gly Asn Ser
515 520 525

Asp Pro Ser Gly Thr Gly Asn Ser Gly Phe Phe Asn Thr Gly Asn Gly
530 535 540

Asn Ser Gly Phe Ser Asn Ala Gly Pro Ala Met Leu Pro Gly Phe Asn
545 550 555 560

Ser Gly Phe Ala Asn Ile Gly Ser Phe Asn Ala Gly Ile Ala Asn Ser
565 570 575

Gly Asn Asn Leu Ala Gly Ile Ser Asn Ser Gly Asp Asp Ser Ser Gly
580 585 590

Ala Val Asn Ser Gly Ser Gln Asn Ser Gly Ala Phe Asn Ala Gly Val
595 600 605

Gly Leu Ser Gly Phe Phe Arg
610 615

<210> SEQ ID NO 15
<211> LENGTH: 590
<212> TYPE: PRT
<213> ORGANISM: Mycobacterium tuberculosis

<400> SEQUENCE: 15

Met Asn Tyr Ser Val Leu Pro Pro Glu Ile Asn Ser Leu Arg Met Phe
1 5 10 15

Thr Gly Ala Gly Ser Ala Pro Met Leu Ala Ala Ser Val Ala Trp Asp
20 25 30

Arg Leu Ala Ala Glu Leu Ala Val Ala Ala Ser Ser Phe Gly Ser Val
35 40 45

Thr Ser Gly Leu Ala Gly Gln Ser Trp Gln Gly Ala Ala Ala Ala Ala
50 55 60

Met Ala Ala Ala Ala Ala Pro Tyr Ala Gly Trp Leu Ala Ala Ala Ala
65 70 75 80

Ala Arg Ala Ala Gly Ala Ser Ala Gln Ala Lys Ala Val Ala Ser Ala
85 90 95

Phe Glu Ala Ala Arg Ala Ala Thr Val His Pro Met Leu Val Ala Ala
100 105 110

Asn Arg Asn Ala Phe Val Gln Leu Val Leu Ser Asn Leu Phe Gly Gln
115 120 125

Asn Ala Pro Ala Ile Ala Ala Ala Glu Ala Met Tyr Glu Gln Met Trp
130 135 140

Ala Ala Asp Val Ala Ala Met Val Gly Tyr His Gly Gly Ala Ser Ala
145 150 155 160

Ala Ala Ala Gln Leu Ser Ser Trp Ser Ile Gly Leu Gln Gln Ala Leu

-continued

```
                165                 170                 175

Pro Ala Ala Pro Ser Ala Leu Ala Ala Ala Ile Gly Leu Gly Asn Ile
            180                 185                 190

Gly Val Gly Asn Leu Gly Gly Gly Asn Thr Gly Asp Tyr Asn Leu Gly
        195                 200                 205

Ser Gly Asn Ser Gly Asn Ala Asn Val Gly Ser Gly Asn Ser Gly Asn
    210                 215                 220

Ala Asn Val Gly Ser Gly Asn Asp Gly Ala Thr Asn Leu Gly Ser Gly
225                 230                 235                 240

Asn Ile Gly Asn Thr Asn Leu Gly Ser Gly Asn Val Gly Asn Val Asn
                245                 250                 255

Leu Gly Ser Gly Asn Arg Gly Phe Gly Asn Leu Gly Asn Gly Asn Phe
            260                 265                 270

Gly Ser Gly Asn Leu Gly Ser Gly Asn Thr Gly Ser Thr Asn Phe Gly
        275                 280                 285

Gly Gly Asn Leu Gly Ser Phe Asn Leu Gly Ser Gly Asn Ile Gly Ser
    290                 295                 300

Ser Asn Ile Gly Phe Gly Asn Asn Gly Asp Asn Asn Leu Gly Leu Gly
305                 310                 315                 320

Asn Asn Gly Asn Asn Asn Ile Gly Phe Gly Leu Thr Gly Asp Asn Leu
                325                 330                 335

Val Gly Ile Gly Ala Leu Asn Ser Gly Ile Gly Asn Leu Gly Phe Gly
            340                 345                 350

Asn Ser Gly Asn Asn Asn Ile Gly Phe Phe Asn Ser Gly Asn Asn Asn
        355                 360                 365

Val Gly Phe Phe Asn Ser Gly Asn Asn Asn Phe Gly Phe Gly Asn Ala
    370                 375                 380

Gly Asp Ile Asn Thr Gly Phe Gly Asn Ala Gly Asp Thr Asn Thr Gly
385                 390                 395                 400

Phe Gly Asn Ala Gly Phe Phe Asn Met Gly Ile Gly Asn Ala Gly Asn
                405                 410                 415

Glu Asp Met Gly Val Gly Asn Gly Gly Ser Phe Asn Val Gly Val Gly
            420                 425                 430

Asn Ala Gly Asn Gln Ser Val Gly Phe Gly Asn Ala Gly Thr Leu Asn
        435                 440                 445

Val Gly Phe Ala Asn Ala Gly Ser Ile Asn Thr Gly Phe Ala Asn Ser
    450                 455                 460

Gly Ser Ile Asn Thr Gly Gly Phe Asp Ser Gly Asp Arg Asn Thr Gly
465                 470                 475                 480

Phe Gly Ser Ser Val Asp Gln Ser Val Ser Ser Ser Gly Phe Gly Asn
                485                 490                 495

Thr Gly Met Asn Ser Ser Gly Phe Phe Asn Thr Gly Asn Val Ser Ala
            500                 505                 510

Gly Tyr Gly Asn Asn Gly Asp Val Gln Ser Gly Ile Asn Asn Thr Asn
        515                 520                 525

Ser Gly Gly Phe Asn Val Gly Phe Tyr Asn Ser Gly Ala Gly Thr Val
    530                 535                 540

Gly Ile Ala Asn Ser Gly Leu Gln Thr Thr Gly Ile Ala Asn Ser Gly
545                 550                 555                 560

Thr Leu Asn Thr Gly Val Ala Asn Thr Gly Asp His Ser Ser Gly Gly
                565                 570                 575

Phe Asn Gln Gly Ser Asp Gln Ser Gly Phe Phe Gly Gln Pro
            580                 585                 590
```

<210> SEQ ID NO 16
<211> LENGTH: 308
<212> TYPE: PRT
<213> ORGANISM: Mycobacterium tuberculosis

<400> SEQUENCE: 16

Met Ser Phe Val Phe Ala Ala Pro Glu Ala Leu Ala Ala Ala Ala Ala
1               5                   10                  15

Asp Met Ala Gly Ile Gly Ser Thr Leu Asn Ala Ala Asn Val Val Ala
            20                  25                  30

Ala Val Pro Thr Thr Gly Val Leu Ala Ala Ala Ala Asp Glu Val Ser
        35                  40                  45

Thr Gln Val Ala Ala Leu Leu Ser Ala His Ala Gln Gly Tyr Gln Gln
    50                  55                  60

Leu Ser Arg Gln Met Met Thr Ala Phe His Asp Gln Phe Val Gln Ala
65                  70                  75                  80

Leu Arg Ala Ser Ala Asp Ala Tyr Ala Thr Ala Glu Ala Ser Ala Ala
                85                  90                  95

Gln Thr Met Val Asn Ala Val Asn Ala Pro Ala Arg Ala Leu Leu Gly
            100                 105                 110

His Pro Leu Ile Ser Ala Asp Ala Ser Thr Gly Gly Gly Ser Asn Ala
        115                 120                 125

Leu Ser Arg Val Gln Ser Met Phe Leu Gly Thr Gly Gly Ser Ser Ala
    130                 135                 140

Leu Gly Gly Ser Ala Ala Ala Asn Ala Ala Ala Ser Gly Ala Leu Gln
145                 150                 155                 160

Leu Gln Pro Thr Gly Gly Ala Ser Gly Leu Ser Ala Val Gly Ala Leu
                165                 170                 175

Leu Pro Arg Ala Gly Ala Ala Ala Ala Ala Ala Leu Pro Ala Leu Ala
            180                 185                 190

Ala Glu Ser Ile Gly Asn Ala Ile Lys Asn Leu Tyr Asn Ala Val Glu
        195                 200                 205

Pro Trp Val Gln Tyr Gly Phe Asn Leu Thr Ala Trp Ala Val Gly Trp
    210                 215                 220

Leu Pro Tyr Ile Gly Ile Leu Ala Pro Gln Ile Asn Phe Phe Tyr Tyr
225                 230                 235                 240

Leu Gly Glu Pro Ile Val Gln Ala Val Leu Phe Asn Ala Ile Asp Phe
                245                 250                 255

Val Asp Gly Thr Val Thr Phe Ser Gln Ala Leu Thr Asn Ile Glu Thr
            260                 265                 270

Ala Thr Ala Ala Ser Ile Asn Gln Phe Ile Asn Thr Glu Ile Asn Trp
        275                 280                 285

Ile Arg Gly Phe Leu Pro Pro Leu Pro Pro Ile Ser Pro Pro Gly Phe
    290                 295                 300

Pro Ser Leu Pro
305

<210> SEQ ID NO 17
<211> LENGTH: 132
<212> TYPE: PRT
<213> ORGANISM: Mycobacterium tuberculosis

<400> SEQUENCE: 17

Met Asp Tyr Ala Phe Leu Pro Pro Glu Ile Asn Ser Ala Arg Met Tyr
1               5                   10                  15

Ser Gly Pro Gly Pro Asn Ser Met Leu Val Ala Ala Ala Ser Trp Asp
20 25 30

Ala Leu Ala Ala Glu Leu Ala Ser Ala Ala Glu Asn Tyr Gly Ser Val
35 40 45

Ile Ala Arg Leu Thr Gly Met His Trp Trp Gly Pro Ala Ser Thr Ser
50 55 60

Met Leu Ala Met Ser Ala Pro Tyr Val Glu Trp Leu Glu Arg Thr Ala
65 70 75 80

Ala Gln Thr Lys Gln Thr Ala Thr Gln Ala Arg Ala Ala Ala Ala Ala
85 90 95

Phe Glu Gln Ala His Ala Met Thr Val Pro Pro Ala Leu Val Thr Gly
100 105 110

Ile Arg Gly Ala Ile Val Val Glu Thr Ala Ser Ala Ser Asn Thr Ala
115 120 125

Gly Thr Pro Pro
130

<210> SEQ ID NO 18
<211> LENGTH: 905
<212> TYPE: PRT
<213> ORGANISM: Mycobacterium tuberculosis

<400> SEQUENCE: 18

Leu Ser Ala Ser Val Ser Ala Thr Thr Ala His His Gly Leu Pro Ala
1 5 10 15

His Glu Val Val Leu Leu Leu Glu Ser Asp Pro Tyr His Gly Leu Ser
20 25 30

Asp Gly Glu Ala Ala Gln Arg Leu Glu Arg Phe Gly Pro Asn Thr Leu
35 40 45

Ala Val Val Thr Arg Ala Ser Leu Leu Ala Arg Ile Leu Arg Gln Phe
50 55 60

His His Pro Leu Ile Tyr Val Leu Leu Val Ala Gly Thr Ile Thr Ala
65 70 75 80

Gly Leu Lys Glu Phe Val Asp Ala Ala Val Ile Phe Gly Val Val Val
85 90 95

Ile Asn Ala Ile Val Gly Phe Ile Gln Glu Ser Lys Ala Glu Ala Ala
100 105 110

Leu Gln Gly Leu Arg Ser Met Val His Thr His Ala Lys Val Val Arg
115 120 125

Glu Gly His Glu His Thr Met Pro Ser Glu Glu Leu Val Pro Gly Asp
130 135 140

Leu Val Leu Leu Ala Ala Gly Asp Lys Val Pro Ala Asp Leu Arg Leu
145 150 155 160

Val Arg Gln Thr Gly Leu Ser Val Asn Glu Ser Ala Leu Thr Gly Glu
165 170 175

Ser Thr Pro Val His Lys Asp Glu Val Ala Leu Pro Glu Gly Thr Pro
180 185 190

Val Ala Asp Arg Arg Asn Ile Ala Tyr Ser Gly Thr Leu Val Thr Ala
195 200 205

Gly His Gly Ala Gly Ile Val Val Ala Thr Gly Ala Glu Thr Glu Leu
210 215 220

Gly Glu Ile His Arg Leu Val Gly Ala Ala Glu Val Val Ala Thr Pro
225 230 235 240

Leu Thr Ala Lys Leu Ala Trp Phe Ser Lys Phe Leu Thr Ile Ala Ile

-continued

```
                245                 250                 255

Leu Gly Leu Ala Ala Leu Thr Phe Gly Val Gly Leu Leu Arg Arg Gln
            260                 265                 270

Asp Ala Val Glu Thr Phe Thr Ala Ala Ile Ala Leu Ala Val Gly Ala
        275                 280                 285

Ile Pro Glu Gly Leu Pro Thr Ala Val Thr Ile Thr Leu Ala Ile Gly
    290                 295                 300

Met Ala Arg Met Ala Lys Arg Arg Ala Val Ile Arg Arg Leu Pro Ala
305                 310                 315                 320

Val Glu Thr Leu Gly Ser Thr Thr Val Ile Cys Ala Asp Lys Thr Gly
                325                 330                 335

Thr Leu Thr Glu Asn Gln Met Thr Val Gln Ser Ile Trp Thr Pro His
            340                 345                 350

Gly Glu Ile Arg Ala Thr Gly Thr Gly Tyr Ala Pro Asp Val Leu Leu
        355                 360                 365

Cys Asp Thr Asp Asp Ala Pro Val Pro Val Asn Ala Asn Ala Ala Leu
    370                 375                 380

Arg Trp Ser Leu Leu Ala Gly Ala Cys Ser Asn Asp Ala Ala Leu Val
385                 390                 395                 400

Arg Asp Gly Thr Arg Trp Gln Ile Val Gly Asp Pro Thr Glu Gly Ala
                405                 410                 415

Met Leu Val Val Ala Ala Lys Ala Gly Phe Asn Pro Glu Arg Leu Ala
            420                 425                 430

Thr Thr Leu Pro Gln Val Ala Ala Ile Pro Phe Ser Ser Glu Arg Gln
        435                 440                 445

Tyr Met Ala Thr Leu His Arg Asp Gly Thr Asp His Val Val Leu Ala
    450                 455                 460

Lys Gly Ala Val Glu Arg Met Leu Asp Leu Cys Gly Thr Glu Met Gly
465                 470                 475                 480

Ala Asp Gly Ala Leu Arg Pro Leu Asp Arg Ala Thr Val Leu Arg Ala
                485                 490                 495

Thr Glu Met Leu Thr Ser Arg Gly Leu Arg Val Leu Ala Thr Gly Met
            500                 505                 510

Gly Ala Gly Ala Gly Thr Pro Asp Asp Phe Asp Glu Asn Val Ile Pro
        515                 520                 525

Gly Ser Leu Ala Leu Thr Gly Leu Gln Ala Met Ser Asp Pro Pro Arg
    530                 535                 540

Ala Ala Ala Ala Ser Ala Val Ala Ala Cys His Ser Ala Gly Ile Ala
545                 550                 555                 560

Val Lys Met Ile Thr Gly Asp His Ala Gly Thr Ala Thr Ala Ile Ala
                565                 570                 575

Thr Glu Val Gly Leu Leu Asp Asn Thr Glu Pro Ala Ala Gly Ser Val
            580                 585                 590

Leu Thr Gly Ala Glu Leu Ala Ala Leu Ser Ala Asp Gln Tyr Pro Glu
        595                 600                 605

Ala Val Asp Thr Ala Ser Val Phe Ala Arg Val Ser Pro Glu Gln Lys
    610                 615                 620

Leu Arg Leu Val Gln Ala Leu Gln Ala Arg Gly His Val Val Ala Met
625                 630                 635                 640

Thr Gly Asp Gly Val Asn Asp Ala Pro Ala Leu Arg Gln Ala Asn Ile
                645                 650                 655

Gly Val Ala Met Gly Arg Gly Gly Thr Glu Val Ala Lys Asp Ala Ala
            660                 665                 670
```

```
Asp Met Val Leu Thr Asp Asp Asp Phe Ala Thr Ile Glu Ala Ala Val
        675                 680                 685

Glu Glu Gly Arg Gly Val Phe Asp Asn Leu Thr Lys Phe Ile Thr Trp
    690                 695                 700

Thr Leu Pro Thr Asn Leu Gly Glu Gly Leu Val Ile Leu Ala Ala Ile
705                 710                 715                 720

Ala Val Gly Val Ala Leu Pro Ile Leu Pro Thr Gln Ile Leu Trp Ile
                725                 730                 735

Asn Met Thr Thr Ala Ile Ala Leu Gly Leu Met Leu Ala Phe Glu Pro
            740                 745                 750

Lys Glu Ala Gly Ile Met Thr Arg Pro Pro Arg Asp Pro Asp Gln Pro
        755                 760                 765

Leu Leu Thr Gly Trp Leu Val Arg Arg Thr Leu Leu Val Ser Thr Leu
    770                 775                 780

Leu Val Ala Ser Ala Trp Trp Leu Phe Ala Trp Glu Leu Asp Asn Gly
785                 790                 795                 800

Ala Gly Leu His Glu Ala Arg Thr Ala Ala Leu Asn Leu Phe Val Val
                805                 810                 815

Val Glu Ala Phe Tyr Leu Phe Ser Cys Arg Ser Leu Thr Arg Ser Ala
            820                 825                 830

Trp Arg Leu Gly Met Phe Ala Asn Arg Trp Ile Ile Leu Gly Val Ser
        835                 840                 845

Ala Gln Ala Ile Ala Gln Phe Ala Ile Thr Tyr Leu Pro Ala Met Asn
    850                 855                 860

Met Val Phe Asp Thr Ala Pro Ile Asp Ile Gly Val Trp Val Arg Ile
865                 870                 875                 880

Phe Ala Val Ala Thr Ala Ile Thr Ile Val Val Ala Thr Asp Thr Leu
                885                 890                 895

Leu Pro Arg Ile Arg Ala Gln Pro Pro
            900                 905
```

<210> SEQ ID NO 19
<211> LENGTH: 636
<212> TYPE: DNA
<213> ORGANISM: Mycobacterium tuberculosis

<400> SEQUENCE: 19

```
gtgccgcatc catgggacac cggcgatcac gaacggaatt ggcagggcta cttcatcccc      60

gctatgtccg tcttgaggaa ccgggtcggc gctcgaacgc atgccgaact gcgtgatgcc     120

gagaacgacc tcgttgaggc ccgggtgatc gaactccgcg aggatcccaa tctgctgggc     180

gaccgcacag atctcgcata cctgcgggcg attcaccgcc agctgttcca ggacatttac     240

gtctgggcgg gagatctgcg gacagtcggc atcgagaagg aggacgagtc tttctgcgcg     300

ccgggcggca tcagtcggcc catggagcat gtggctgcgg agatctacca gctcgaccgg     360

ctcagagcgg tcggcgaagg tgatctcgct ggccaggtcg cataccggta cgactacgtg     420

aactatgccc acccgttccg cgagggcaac ggccgctcga cccgcgagtt cttcgatctc     480

ctgttgtccg aacgcggttc tggcctcgac tgggggaaga ccgacctgga agagttgcac     540

ggcgcttgtc acgtggcgcg cgccaactct gatctcacgg gcctggtcgc gatgttcaag     600

gggatcctcg acgccgagcc cacttacgac ttctga                                636
```

<210> SEQ ID NO 20
<211> LENGTH: 1143

<212> TYPE: DNA
<213> ORGANISM: Mycobacterium tuberculosis

<400> SEQUENCE: 20
atggatttcg cactgttacc accggaagtc aactccgccc ggatgtacac cggccctggg 60
gcaggatcgc tgttggctgc cgcgggcggc tgggattcgc tggccgccga gttggccacc 120
acagccgagg catatggatc ggtgctgtcc ggactggccg ccttgcattg gcgtggaccg 180
gcagcggaat cgatggcggt gacggccgct ccctatatcg gttggctgta cacgaccgcc 240
gaaaagacac agcaaacagc gatccaagcc agggcggcag cgctggcctt cgagcaagca 300
tacgcaatga ccctgccgcc accggtggta gcggccaacc ggatacagct gctagcactg 360
atcgcgacga acttcttcgg ccagaacact gcggcgatcg cggccaccga ggcacagtac 420
gccgagatgt gggcccagga cgccgccgcg atgtacggtt acgccaccgc ctcagcggct 480
gcggccctgc tgacaccgtt ctccccgccg cggcagacca ccaacccggc cggcctgacc 540
gctcaggccg ccgcggtcag ccaggccacc gacccactgt cgctgctgat tgagacggtg 600
acccaagcgc tgcaagcgct gacgattccg agcttcatcc ctgaggactt caccttcctt 660
gacgccatat tcgctggata tgccacggta ggtgtgacgc aggatgtcga gtcctttgtt 720
gccgggacca tcggggccga gagcaaccta ggccttttga acgtcggcga cgagaatccc 780
gcggaggtga caccgggcga ctttgggatc ggcgagttgg tttccgcgac cagtcccggc 840
ggtggggtgt ctgcgtcggg tgccggcggt gcggcgagcg tcggcaacac ggtgctcgcg 900
agtgtcggcc gggcaaactc gattgggcaa ctatcggtcc caccgagctg ggccgcgccc 960
tcgacgcgcc ctgtctcggc attgtcgccc gccggcctga ccacactccc ggggaccgac 1020
gtggccgagc acgggatgcc aggtgtaccg ggggtgccag tggcagcagg gcgagcctcc 1080
ggcgtcctac ctcgatacgg ggttcggctc acggtgatgg cccacccacc cgcggcaggg 1140
taa 1143

<210> SEQ ID NO 21
<211> LENGTH: 720
<212> TYPE: DNA
<213> ORGANISM: Mycobacterium tuberculosis

<400> SEQUENCE: 21
atgactgagc ccagacctgt cttcgctgtc gtgatcagcg ccggcctatc cgccatcccg 60
atggtcggcg gcccgctaca aaccgtgttc gacgccatcg aggaacgcac ccggcaccgc 120
gccgagacaa ccacgcgcga gatatgcgag agcgtcggcg gcgcggacac cgtgttgagc 180
cgcattgaca aaaatcccga actcgagccg cttctcagcc aggcgatcga ggccgccact 240
cgcaccagta tggaggccaa gcgccggctc ctcgcgcaag ctgccgccgc cgcgctcgag 300
gatgaccaga aggtcgagcc ggcatcactc atcgtggcca cgctttccca acttgagccc 360
gtgcatatcc atgcactcgt tcggctggcc aaagccgcca agtcctcacc ggaccaggac 420
gagatccagc gacgcgaggt gatgagggcg gcgagtaagg tcgagcccgt gccggtgcta 480
gcggccctca ttcaaaccgg cgtcgcgatc gcgacaacaa ccgtttggca cggcaacggc 540
accgggactc cggcagaaga aagcggccac atccttatcc acgacgtcag cgacttcggc 600
caccgcctgc tggcctatct cagggccgcc gacgcaggtg ccgagctcct catcctcccc 660
tctggagggt ctgcgccaac cggcgaccac ccgacgccgc acccgtccac gtcgagatga 720

<210> SEQ ID NO 22

<211> LENGTH: 1440
<212> TYPE: DNA
<213> ORGANISM: Mycobacterium tuberculosis

<400> SEQUENCE: 22
atggcggatt tcttgacgtt gtcaccagag gtgaattcgg cccggatgta cgcgggtggg 60
gggcccgggt cgctatcggc ggccgcggcg gcctgggatg agttggccgc cgaactgtgg 120
ttggcggcgg cctcgttcga gtcggtgtgc tccggcctgg cggaccgttg gtggcaaggg 180
ccgtcgtctc ggatgatggc ggcgcaggcc gcccgccata cggggtggct ggccgcggcg 240
gccacccagg cagagggagc agccagccag gctcagacga tggcgctggc ctatgaagcg 300
gcgttcgccg caaccgtaca cccggcgctg gtcgcggcga accgcgccct cgtggcctgg 360
ttggcggggt cgaatgtgtt cggcgcagaac accccggcga ttgcggccgc cgaggccatc 420
tacgagcaga tgtgggctca ggatgttgtc gcgatgttga actaccatgc ggtggcctcg 480
gcggtcgggg cgcggttgcg gccgtggcag cagttgctgc atgagctgcc caggcggttg 540
ggcggcgaac actccgacag cacaaacacg gaactcgcta acccgagttc aacgacgaca 600
cgcattaccg tccccggcgc atctccggtg catgcagcga cgttactgcc gttcatcgga 660
aggctactgg cggcgcgtta tgccgagctg aacaccgcga tcggcacgaa ctggtttccg 720
ggcaccacgc cagaagtggt gagctatccg gccaccatcg gggtccttag cggctctctt 780
ggcgccgtcg atgccaacca gtccatcgct atcggtcagc agatgttgca caacgagatc 840
ctggccgcca cggcctccgg tcagccggtg acggtggccg gactgtcgat gggcagcatg 900
gtcatcgacc gcgaacttgc ctatctggcc atcgacccca acgcgccacc ctcgagcgcg 960
ctcacattcg tcgagctcgc cggcccggaa cgcggtcttg cccagaccta cctgcccgtt 1020
ggcaccacca ttccaatcgc ggggtacacc gtggggaatg cgcccgagag ccagtacaac 1080
accagcgtgg tttatagcca gtacgatatc tgggccgatc cgcccgaccg tccgtggaac 1140
ctgttggccg gcgccaacgc actgatgggc gcggcttact ttcacgatct gaccgcctac 1200
gccgcaccac aacaggggat agagatcgcc gctgtcacga gttcactggg cggaaccacg 1260
acaacgtaca tgattccgtc gcccacgctg ccgttgctgt tgccactgaa gcagatcggt 1320
gtcccagact ggatcgtcgg cgggctgaac aacgtgctga agccgctcgt cgacgcgggc 1380
tactcacagt acgcccccac cgccggccct tatttcagcc acggcaacct ggtgtggtag 1440

<210> SEQ ID NO 23
<211> LENGTH: 1185
<212> TYPE: DNA
<213> ORGANISM: Mycobacterium tuberculosis

<400> SEQUENCE: 23
atgaccctcg atgtcccggt caaccagggg catgtccccc cgggcagcgt cgcctgctgc 60
cttgttgggg tcaccgccgt tgctgacggc atcgccgggc attccctgtc caactttggg 120
gcgttacctc ccgagatcaa ttcgggtcgt atgtatagcg gtccgggatc cgggccactg 180
atggctgccg cggcggcctg ggacgggctg gccgcagagt tgtcgtcggc agcgactggc 240
tacggtgcgg cgatctcgga gctgacaaac atgcggtggt ggtcggggcc ggcatcggat 300
tcgatggtgg ccgccgtcct gcccttttgtc ggctggctga gtaccaccgc gacgctagcc 360
gaacaggccg cgatgcaggc tagggcggcc gcagcggcct ttgaagccgc cttcgccatg 420
acggtgcccc cgccggcgat cgcggccaac cggaccttgt tgatgacgct cgtcgatacc 480
aactggttcg ggcaaaacac gccggcgatc gccaccaccg agtcccaata cgccgagatg 540
tgggcccaag acgccgccgc gatgtacggc tatgccagcg ccgcggcacc cgccacggtt 600
ttgactccgt tcgcaccacc gccgcaaacc accaacgcga ccggcctcgt cggccacgca 660
acagcggtgg ccgcgctgcg ggggcagcac agctgggccg cggcgattcc atggagcgac 720
atacagaaat actggatgat gttcctgggc gccctcgcca ctgccgaagg gttcatttac 780
gacagcggtg ggttaacgct gaatgctctg cagttcgtcg gcgggatgtt gtggagcacc 840
gcattggcag aagccggtgc ggccgaggca gcggccggcg cgggtggagc cgctggatgg 900
tcggcgtggt cgcagctggg agctggaccg gtggcggcga gcgcgactct ggccgccaag 960
atcggaccga tgtcggtgcc gccgggctgg tccgcaccgc ccgccacgcc ccaggcgcaa 1020
accgtcgcgc gatcgattcc cggtattcgc agcgccgccg aggcggctga aacatcggtc 1080
ctactccggg gggcaccgac tccgggcagg agtcgcgccg cccatatggg acgccgatat 1140
ggaagacgac tcaccgtgat ggctgaccgg ccgaacgtcg gatag 1185

<210> SEQ ID NO 24
<211> LENGTH: 1176
<212> TYPE: DNA
<213> ORGANISM: Mycobacterium tuberculosis

<400> SEQUENCE: 24
atggatttcg gagctttacc ccctgagatc aactccgcac gcatgtacgc cggcgcgggt 60
gcaggaccga tgatggccgc cggggccgca tggaacggcc tggccgccga gttgggtacg 120
acggccgcgt cgtatgagtc ggtgatcacc cggctgacca ccgagtcgtg gatgggtccg 180
gcctcgatgg cgatggtcgc cgcagcccag ccctatctgg cttggttgac ctacaccgcc 240
gaagccgctg cgcatgccgg ctcgcaggcc atggcgtcgg cggccgccta cgaggcggcc 300
tatgcgatga cagtgccgcc ggaggtggtc gcggccaacc gggcgctgct ggcggccctg 360
gtcgcgacga acgtcctggg gatcaacaca ccggcaatca tggcgaccga agccctctat 420
gccgagatgt gggctcagga cgctctggct atgtacggct acgcggccgc ttcgggagcc 480
gccgggatgc tgcaaccgtt aagcccgccg tcgcagacca ccaacccggg cgggctggcc 540
gcccagtccg ccgcggtcgg ctcggctgcc gccaccgccg ccgtcaacca ggtgagcgta 600
gcggacctga tcagtagcct gcccaacgcg gtgagtgggc tcgcctcccc agtcacatcg 660
gttctcgact cgacggggct gagcggaatc attgccgaca tcgacgccct gctcgcgacc 720
ccgttcgtgg caaacatcat caacagcgca gtcaacaccg ccgcttggta tgtcaacgcc 780
gccatcccca ccgcgatatt cctagcaaat gccctgaaca gtggggcgcc ggtagcgatc 840
gccgaaggcg ccatcgaggc tgccgagggt gccgccagtg cggccgccgc ggggttggcg 900
gactcggtga cgccagcggg gctcggcgca agtttaggcg aggccaccct ggtcggccgg 960
ctgtcagtgc cggcggcctg gtctacggcc gcaccggcga caaccgccgg cgccacagcg 1020
ctcgaaggca gcggctggac cgtcgccgcc gaagaagccg gcccagttac cgggatgatg 1080
ccgggaatgg cctcggccgc caagggcacc ggtgcctatg ccgggccgcg gtacggattc 1140
aagcccactg tcatgcccaa acaggtcgtc gtgtga 1176

<210> SEQ ID NO 25
<211> LENGTH: 1659
<212> TYPE: DNA
<213> ORGANISM: Mycobacterium tuberculosis

<400> SEQUENCE: 25

-continued

```
atggctcatt tttcggtgtt gccgccggag atcaactcgt tgcggatgta cctgggtgcc     60

ggttcggcgc cgatgcttca ggcggcggcg gcctgggacg ggctggccgc ggagttggga    120

accgccgcgt cgtcgttctc ctcggtgacc acggggttaa ccgggcaggc gtggcagggc    180

ccggcgtcgg cggcgatggc cgccgcggcg gcgccgtatg cgggcttttt gaccacagcc    240

tcggctcaag cccagctggc tgccgggcag gctaaggcgg tggccagcgt gttcgaggcc    300

gccaaggccg cgatcgtgcc tccggccgcg gtggcggcca accgtgaggc gttcttggcg    360

ttgattcggt cgaattggct ggggctcaac gcgccgtgga tcgccgccgt tgaaagcctt    420

tacgaggaat actgggccgc tgatgtggcg gcgatgaccg gctatcacgc cggggcctcg    480

caggccgccg cgcagttgcc gttgccggcc ggcctgcaac agttcctcaa caccctgccc    540

aatctgggca tcggcaacca gggcaacgcc aacctcggcg gcggcaacac cggcagcggc    600

aacatcggca acggaaacaa aggcagctcc aacctcggcg gcggcaacat cggcaataac    660

aacatcggca gcggcaaccg aggcagcgac aacttcggcg ccggcaacgt cggcaccgga    720

aacatcggct tcggcaacca gggccccata gacgttaacc tcttggcgac gccgggccag    780

aacaacgtgg gcctgggcaa catcggcaac aacaacatgg gcttcggcaa caccggcgac    840

gccaacaccg gcggcggcaa caccggcaac ggcaacatcg gtggcggcaa caccggcaac    900

aacaacttcg gcttcggcaa caccggcaac aacaacatcg gaatcgggct caccggcaac    960

aatcagatgg gcatcaacct ggccgggctg ctgaactccg gcagcggcaa tatcggcatc   1020

ggcaactccg gcaccaacaa catcggcttg ttcaactccg gcagcggcaa catcggcgtc   1080

ttcaacaccg gagccaatac cctggtgcct ggcgacctca acaacctggg cgtcgggaat   1140

tccggcaacg ccaacatcgg cttcgggaac gcgggcgttc tcaacaccgg cttcgggaac   1200

gcgagcatcc tcaacaccgg cttggggaac gcgggtgaat taaacaccgg cttcggaaac   1260

gcgggcttcg tcaacacggg gtttgacaac tccggcaacg tcaacaccgg caatgggaac   1320

tcgggcaaca tcaacaccgg ctcgtggaat gcgggcaatg tgaacaccgg tttcgggatc   1380

attaccgaca gcggcctgac caactcgggc ttcggcaaca ccggcaccga cgtctcgggc   1440

ttcttcaaca cccccaccgg ccccttagcc gtcgacgtct ccgggttctt caacacggcc   1500

agcgggggca ctgtcatcaa cggccagacc tcgggcattg gcaacatcgg cgtcccgggc   1560

accctctttg gctccgtccg gagcggcttg aacacgggcc tgtttaacat gggcaccgcc   1620

atatcggggt tgttcaacct gcgccagctg ttggggtag                          1659
```

<210> SEQ ID NO 26
<211> LENGTH: 1689
<212> TYPE: DNA
<213> ORGANISM: Mycobacterium tuberculosis

<400> SEQUENCE: 26

```
atggagtatc tgattgcagc gcaggacgtg ttggtggccg cggccgctga tttggagggc     60

atcggctcgg cgctggccgc agctaacagg gcggccgagg ccccgaccac ggggctgctg    120

gccgcgggtg ccgacgaggt atcagcggcc atcgcgtcgc tgttttccgg gaacgcccag    180

gcctatcaag cgctgagcgc acaggcggcg gcatttcatc agcagtttgt gcgggcactg    240

agttcggcgg ccggctcgta tgcggcggcc gaggccgcca atgcctcccc gatgcaagcg    300

gtgctggatg tggtcaatgg gcccacccag ctgttgctgg ggcgcccgct gatcggcgat    360

ggcgccaacg gcgggccggg acaaaacggg ggcgacggtg gcttgttgta cggcaacggc    420

ggcaacggcg gctcgagtag caccccaggc cagcccggcg gtcgcggcgg cgcggccggg    480
```

-continued

```
ttgatcggca acggtggcgc cgggggagcc ggcgggcccg gcgcgaacgg cggtgccggc    540
ggcaacggcg ggtggctata cggcaacggt gggctcggcg gcaacggtgg ggcggccacc    600
cagatcgggg gcaatggcgg caacggaggc cacggcggca acgccgggct atggggcaac    660
ggggggggcgg gtggagccgg agcggcagga gcggccggcg ccaacgggca aaacccggtg    720
tcccatcagg tcacgcacgc gaccgatggc gccgacggca ctaccggacc cgatggcaac    780
gggaccgacg ccggctcggg cagcaacgca gtcaaccccg gcgtgggcgg tggtgcaggc    840
ggcataggcg gggatggaac caaccttggg cagaccgacg tgtccggggg tgccggcggc    900
gacggcggcg acggcgccaa cttcgcctcc ggaggtgccg gcggtaacgg tggcgccgct    960
caaagcggct ttggtgacgc tgtcggcggc aatggcggcg ccggcggaaa cggcggagcc   1020
ggcggcggcg gggggctggg cggagcgggt ggcagcgcca atgttgcaaa tgctggcaac   1080
agcatagggg gcaacggtgg cgccggcggg aacggcggta tcggcgctcc cggtggtgcc   1140
ggcggcgccg gaggaaatgc caatcaagat aatcctcctg gggcaactc caccggggggc   1200
aatggtggtg ccggcggcga cggcggcgtc ggtgcctcgg ctgacgttgg tggcgccggc   1260
ggctttgggg gcagcggggg tcgcggcggg ctactgctcg gcacgggcgg cgccggcggc   1320
gacggcggcg tcgggggcga cgggggcatc ggcgctcaag gcggcagcgg cggcaacggc   1380
ggcaacggcg ggatcggcgc cgacggcatg gccaaccagg acggcgacgg cggtgacggc   1440
ggcaacggcg gcgacggcgg ggccggcggg gccggtggcg tcggcggaaa cggcgggacc   1500
ggcggtgcgg gcggactgtt cggacagtcg ggcagccccg gctccggcgc ggccgggggc   1560
ctcggcggcg cgggcggcaa cggcggcgcg ggcggcggcg gcgggaccgg gttcaacccc   1620
ggcgcccccg gcgatcccgg tactcaaggc gctaccggcg ccaacggtca gcacggcctg   1680
aacggctga                                                           1689
```

<210> SEQ ID NO 27
<211> LENGTH: 4617
<212> TYPE: DNA
<213> ORGANISM: Mycobacterium tuberculosis

<400> SEQUENCE: 27

```
atggtcatgt cgctgatggt ggcgccggag ctggtggcgg cggccgcggc ggacttgacc     60
gggattgggc aggccatcag cgcggcgaat gcggcggcag cgggcccgac gacgcaggtg    120
ttggcggccg ccggtgatga ggtgtcggcg gcgatcgcgg cgttgtttgg tacccacgcg    180
caggagtacc aggcgttgag cgcccgggtg gcgacgtttc atgagcagtt tgtgcgctcg    240
ctgaccgcgg ctggcagcgc gtatgcgact gccgaggcgg cgaatgcatc accgctgcag    300
gcgctggagc agcaagtgtt gggtgcgatc aacgcgccca cacagctgtg gttggggcgc    360
ccgctgatcg gtgatggcgt tcacggggcg ccggggaccg ggcagcccgg tggggccggg    420
gggttgttgt ggggtaatgg cggtaacggc ggttcggggg cggccggtca agtcggtggg    480
cccggcggcg cggccgggtt gttcggcaac ggcgggtccg gcgggtccgg cggggccggc    540
gctgccggcg gtgtcggcgg atccggcggg tggttgaacg gcaacggcgg ggccggcggg    600
gccggcggga ccggcgctaa cggtggtgcc ggcggcaacg cctggttgtt cggggccggc    660
gggtccggcg gcgccggcac caatggtggc gtcggcgggt ccggcggatt tgtctacggc    720
aacggcggcg ccggcgggat cggcggcatc ggaggtatag gcggcaacgg tggcgacgcc    780
gggctgttcg ggaacggcgg cgccgggggg gccggggccg cgggcctgcc gggtgccgcc    840
```

-continued

```
ggcctcaacg gcggcgacgg cagcgacggc ggcaacggcg gaaccggcgg caacggcggg    900
cgcggcgggt tattggttgg caacggcggg gccggcgggg ccggcggcgt cggcggcgac    960
ggtggtaagg gcggcgctgg cgatccgagt ttcgccgtca acaacggtgc cggcggtaac   1020
ggcggtcacg gcggcaaccc cggcgtgggc ggggccggtg gggccggcgg cctgctggcg   1080
ggtgcgcacg gtgccgccgg cgccaccccc accagcggcg gcaacggcgg cgatggcggc   1140
atcggcgcca ccgccaactc acccctacaa gccggcgggg ccggcggtaa tggcggtcat   1200
ggcgggttgg tcggcaacgg cggcaccggc ggcgccggcg gtgccggtca tgcgggttcc   1260
accggcgcta ccggtaccgc cttacaaccg acgggcggta acggcaccaa tggcggcgcc   1320
gggggccacg gcggtaatgg cggaaatggc ggcgcccagc acggcgacgg cggcgtcggc   1380
ggcaagggcg gtgccggcgg tagcggcggc gccggcggaa acggattcga cgccgccacc   1440
ttgggttcgc ccggtgccga tggcggtatg ggcggcaacg gcggcaaggg cggtgacggc   1500
ggcaaggccg gtgatggcgg agccggtgcc gccggtgatg tgaccttggc cgtcaaccag   1560
ggtgccggcg gtgacggcgg caacggcggt gaagtgggcg ttggcggcaa gggtggggcc   1620
ggcggtgtta gcgcgaaccc ggccctgaac ggttcggccg gggcgaacgg caccgcgccc   1680
accagcggcg gcaacggtgg caacggaggt gccggcgcca cccccaccgt cgcgggagaa   1740
aacggcggcg ccggtggtaa cggcggccat ggcgggtcgg tcggtaacgg cggtgcgggt   1800
ggtgccggcg gaaatggcgt cgccggcacc ggccttgccc tcaacggcgg caacggcggc   1860
aacggcggca tcggcggcaa cggcggatcg gcggccggca cgggcgggga cggcggcaag   1920
ggcggcaacg gggcgccgg agccaacggc caagacttct ccgcgtccgc caatggcgcg   1980
aatggcggac agggcggcaa cggcggcaac ggcggcatcg gcggcaaggg tggtgacgcc   2040
ttcgccacgt tcgctaaggc cggcaacggc ggtgccggcg gcaacggcgg caatgtgggc   2100
gttgccggcc agggtggggc cggcggcaag ggcgccattc cagccatgaa gggtgcgacc   2160
ggcgccgatg gcaccgcacc caccagcggc ggtgacggcg gcaacggcgg caacggcgcc   2220
agccccaccg tcgcgggcgg caacggcggt gacggcggca agggcggcag cggcgggaat   2280
gtcggcaatg gcggcaatgg cggggccggc ggcaacggcg cggccggcca agccggtacg   2340
ccgggcccta ccagcggtga ttccggcacc tcgggcaccg acggtggggc tggcggcaac   2400
ggcggggcgg gcggcgccgg cggaacactg gccggccacg gcggcaacgg tggtaagggt   2460
ggtaacggcg gccagggtgg catcggcggc gccggcgaga gaggcgccga cggcgccggc   2520
cccaatgcta acggcgcaaa cggcgagaac ggcggtagcg gtggtaacgg tggcgacggc   2580
ggcgccggcg gcaatggcgg cgcgggcggc aaggcgcagg cggccgggta caccgacggc   2640
gccacgggca ccggcggcga cggcggcaac ggcggcgatg gcggcaaagc cggtgacggc   2700
ggggccggcg aaaacggcct aaacagcggg gccatgctgc cgggcggcgg caccgtagga   2760
aaccccggta ccggcggcaa cggcggcaac ggcggcaacg ccggcgtcgg cggcaccgga   2820
ggcaaggccg gcaccggctc cttgacgggc ttggacggca ccgacggcat cacccccaac   2880
ggcggtaacg gcggcaatgg cggcaacggc ggcaagggcg gcaccgccgg caacgggagc   2940
ggcgcggccg gcggcaacgg cggcaacggc ggctccggcc tcaacggcgg tgacgccggc   3000
aacggcggca acggcggtgg ggcgctgaac caggccggct tcttcggcac gggcggcaaa   3060
ggcggtaacg gcggcaatgg cggtgccggc atgatcaacg gcggcctcgg cggcttcggc   3120
ggcgccggcg gtggcggcgc cgttgacgtc gccgcgacaa cgggcggcgc tggcggcaat   3180
ggcggtgccg gcggcttcgc tagcaccggg ttgggtggcc caggcggcgc cggcggtccc   3240
```

```
ggcggcgcgg gcgactttgc tagcggtgtt ggcggtgtcg gcggcgccgg cggggacggc   3300
ggtgccggcg gggtcggcgg cttcggcggc cagggcggca tcggcgggga agggcgcaca   3360
ggcggcaacg gcggtagcgg cggcgacggc ggtggcggca tttccttagg cggcaacggc   3420
ggcctcggcg gcaacggcgg cgtctccgag actgggtttg gcggcgccgg cggcaacggc   3480
ggctacggcg gtccgggagg ccccgaaggc aatggcggcc tcggcggcaa cggcggcgcc   3540
ggcggcaacg gcggcgtcag caccacgggc ggcgacggcg gcgccggcgg caagggcggc   3600
aacggcggcg acggcgggaa cgtcggtttg ggcggtgacg ccggctccgg cggcgcgggc   3660
ggcaatggcg gtatcggcac cgacgcgggc ggtgccggag gggccggtgg cgctggcggt   3720
aacggcggta gcagcaaaag cacgaccacc ggcaacgccg gctccggtgg tgccggcggt   3780
aatgggggca ctggcctcaa cggcgcgggc ggtgctggcg gggccggcgg caacgcgggt   3840
gtcgccggcg tgtccttcgg caacgctgtg ggcggcgacg gcggcaacgg cggcaacggc   3900
ggccacggcg gcgacggcac gacgggcggc gccggcggca agggcggcaa cggcagcagc   3960
ggtgccgcca gcggctcagg cgtcgtcaac gtcaccgccg gccacggcgg caacggcggc   4020
aatggcggca acggcggcaa cggctccgcg ggcgccggcg gccagggcgg tgccggcggc   4080
agcgccggca acggcggcca cggcggcggt gccaccggcg gcgacggcgg caacggcggc   4140
aacggcggca actccggcaa cagcaccggc gtcgcgggct tggccggtgg tgccgccggc   4200
gccggcggca acggcggcgg cacttccagc gccgccggcc acggcggcag cggcggcagc   4260
ggtggcagcg gcaccacggg cggcgccggc gcggccggcg gcaacggcgg cgccggtgct   4320
ggcgggggca gcctgagcac aggccagtcc ggcggcccac ggcggcagcg gtggtgccgg   4380
tggcaacggc ggcgctggct cggccggcaa cggcggcgcc ggtggtgccg gtggcaacgg   4440
cggtgccggc ggcaacggtg gcggtggcga tgccggcaac gccggctcag gcggcaatgg   4500
cggcaagggc ggcgacggtg tcggccctgg ctccaccggc ggcgcgggcg gcaagggcgg   4560
cgctggcgcc aacggcggtt ccagcaacgg caacgctcgc ggtggcaacg ccggtaa      4617
```

<210> SEQ ID NO 28
<211> LENGTH: 1272
<212> TYPE: DNA
<213> ORGANISM: Mycobacterium tuberculosis

<400> SEQUENCE: 28

```
gtgatccaaa cgtgtgaagt cgagttgcgc tggcgtgcat cacaactgac gctggcgatt     60
gccacctgtg ccggagttgc gctagccgca gcggtcgtcg ctggtcgttg gcagctgatt    120
gcgttcgcgg cgccgctgct cggcgtgttg tgctcgatca gctggcagcg tccggtcccg    180
gtgatccagg tgcacggtga cccggattcg cagcgatgtt tcgagaacga acatgtgcga    240
gtgaccgtgt gggtcacaac ggaatccgtg gacgccgcgg tcgaactcac ggtatcggcg    300
ttggcgggaa tgcagttcga agctctggaa tccgtgtcac gccggacgac aacggtttcc    360
gcggtggcgc aacgctgggg gcgctatcct atccgggccc gggtcgccgt cgtcgcacgc    420
ggtgggttgt tgatgggagc cggaaccgtc gacgccgccg aaatcgtcgt gtttccgctg    480
acaccgccgc agtcgacgcc actgccgcag accgaattgc tcgaccgcct gggagctcat    540
ctcacccggc acgtcggccc gggtgtcgaa tacgccgaca ttcgcccata tgtcccgggc    600
gaccagctac gtgccgtgaa ctgggtggta agcgcgcgcc gtggccgact gcacgtgaca    660
aggcggttga ccgaccgggc cgctgacgtg gtggtgttga tcgacatgta tcgacagccg    720
```

-continued

```
gcgggtccgg cgaccgaggc caccgaacga gtcgtgcggg gtgctgctca ggtggtgcaa     780

accgcgctgc gaaacggtga ccgtgctggg atcgttgcgc tgggcggcaa tcggccgcga     840

tggctgggcg ccgacatcgg gcagcgccag ttctatcggg tgctcgacac cgtgctcggc     900

gccggggaag ggttcgaaaa caccaccggg acgctggctc cgcgcgcagc tgttcccgca     960

ggagcggttg tcattgcgtt ttccacgctg ctggataccg agttcgcgct ggcgttgatc    1020

gacctgcgta aacgcggcca cgtcgtggtt gctgtcgacg ttcttgatag ctgtccgctc    1080

caggaccaac tggatcccct ggtggtccgg atgtgggcgc tgcagcgctc cgcgatgtat    1140

cgcgacatgg ccaccatcgg ggtcgacgtg ctgtcctggc cggcggatca ctcgcttcag    1200

cagtcgatgg gtgcgttgcc caatcgccgt cgtcgcggac ggggcagagc tagccgggcg    1260

aggctgccat ga                                                        1272
```

<210> SEQ ID NO 29
<211> LENGTH: 1023
<212> TYPE: DNA
<213> ORGANISM: Mycobacterium tuberculosis

<400> SEQUENCE: 29

```
gtgaataggc ggatattgac cttgatggtc gcgctggtgc cgatcgtggt attcggcgtg      60

ttgctcgccg tggtaaccgt gccgtttgtg gcgctgggac ccggcccaac gttcgacacg     120

ctcggcgaga tagacggcaa gcaggtggtc cagatcgtgg gcacccagac ctacccgacg     180

tcaggtcacc tcaacatgac gacggtctcc cagcgcgacg gtctaaccct gggtgaagcc     240

ctggccctgt ggctttcggg tcaagaacag ttgatgccac gcgacctcgt ctaccctccg     300

ggcaagtcgc gggaagagat cgaaaatgac aacgccgctg atttcaagcg ctccgaggcc     360

gccgctgagt acgccgctct ggggtacctg aagtatccga aagcagtcac cgtcgcctcg     420

gtcatggatc cagggccatc ggtggacaag ctgcaggccg gtgacgccat cgacgccgtc     480

gacggcactc cggtgggcaa cctcgaccag ttcaccgcgc tgttgaagaa cacgaaaccg     540

ggccaggagg tgacgatcga cttccgccgc aagaacgagc cgcccggcat cgcgcagatc     600

acgctgggca agaataagga tcgcgaccaa ggcgtcctgg gcatagaggt ggtggacgcg     660

ccgtgggcgc cgtttgccgt ggacttccac ctcgccaacg tcggcggccc ttcggccgga     720

ctgatgttca gtctggccgt cgtcgacaag ctcaccagtg gccacctggt tgggtcgacg     780

ttcgtcgcag gcaccggcac gatcgccgtc gatggcaagg tgggccagat cggtggcatc     840

acccacaaga tggccgctgc tcgagcggcc ggcgcgacgg tgtttctggt gcccgcgaag     900

aactgctacg aggcaagttc cgacagcccg cccggtttga agttggtgaa ggtcgagacg     960

cttagccagg cggtggacgc gctgcacgcg atgacgtcgg gctcgccgac gccgagctgc    1020

tag                                                                  1023
```

<210> SEQ ID NO 30
<211> LENGTH: 2772
<212> TYPE: DNA
<213> ORGANISM: Mycobacterium tuberculosis

<400> SEQUENCE: 30

```
atgtccttcg tggtcacagc accgccggtg ctcgcgtcgg cggcgtcgga tctgggcggt      60

atcgcgtcca tgatcagcga ggccaacgcg atggcagcgg tccgaacgac ggcgttggcg     120

cccgccgccg ccgacgaggt ttcggcggcg atcgcggcgc tgttttccag ctacgcgcgg     180

gactatcaaa cgctgagcgt ccaggtgacg gccttccacg tgcagttcgc gcagacattg     240
```

-continued

```
accaatgcgg ggcagctgta tgcggtcgtc gacgtcggca atggcgtgct gttgaagacc    300
gagcagcagg tgctgggtgt gatcaatgcg cccacccaga cgttggtggg tcgtccgctg    360
atcggcgatg gcacccacgg ggcgccgggg accgggcaga acggtggggc gggcggaatc    420
ttgtggggca acggcggtaa cggcgggtcc ggggctcccg gacagccggg cggccggggc    480
ggtgatgccg gcctgttcgg ccacggcggt catggcggtg tcggggggcc gggcatcgcc    540
ggtgccgctg gcaccgcggg cctgcccggg ggcaacggcg ccaacggcgg aagcggcggc    600
atcggcggcg ccggcggcgc cggcggcaac ggcgggctgc tattcggcaa cggtggtgcc    660
ggcggccagg gtggctccgg cggacttggg ggctccggcg ggacgggcgg cgcgggcatg    720
gctgccggtc ccgccggcgg caccggcggc atcgggggca tcggcggcat cggcggcgcg    780
ggcggggtcg gcggccacgg ctcggcgttg ttcggccacg gggggaatcaa cggcgatggc    840
ggtaccggcg gcatgggtgg ccagggcggt gctggcggca acggctgggc cgctgagggc    900
atcacggtcg gcattggtga gcaaggcggc cagggcggcg acgggggagc cggcggcgcc    960
ggcgggatcg gtggttcggc gggtgggatc ggcggcagcc agggtgcggg tgggcacggc   1020
ggcgacggcg gccagggcgg cgccggcggt agtggcggcg ttggcggcgg cggcgcaggc   1080
gccggcggcg acggcggcgc gggcggcatc ggcggcactg gcggtaacgg cagcatcggc   1140
ggggccgccg gcaatggcgg taacggcggc cgcggcggcg ccggtggcat ggccaccgcg   1200
ggaagtgatg gcggcaatgg cggcggcggc ggcaacggcg gcgtcggtgt tggcagcgcc   1260
ggaggggccg gcggcaccgg cggtgacggc ggggcggccg gggcgggcgg cgcgccgggc   1320
cacggctact tccaacagcc cgcgccccaa gggctgccca tcggaaccgg cgggaccggc   1380
ggcgaaggcg gtgccggcgg cgccggtgga gacggcgggc agggcgacat cggcttcgat   1440
ggcggccggg gtggcgacgg cggcccgggc ggtggcggcg gcgccggcgg tgacggcagc   1500
ggcaccttca atgcccaagc caacaacggc ggcgacggtg gtgccggcgg tgttggggga   1560
gccggcggca ccggcggcac gggtggggtc ggggccgacg gggggtcgcgg gggggactcg   1620
ggccgcggcg gcgacggcgg caacgccggc cacggcggcg ccgcccaatt ctccggtcgc   1680
ggcgcctacg gcggtgaagg tggcagcggc ggcgccggcg gcaacgccgg tggcgccggc   1740
accggtggca ccgcgggctc cggcggtgcc ggaggtttcg gcggcaacgg tgccgatggc   1800
ggcaatggcg gcaacggtgg caacggcggc ttcggcggaa ttaacggcac gttcggcacc   1860
aacggtgccg gcggcaccgg cgggctcggc accctgctcg gcggccacaa cggcaacatc   1920
ggcctcaacg gggccaccgg cggcatcggc agcaccacgt tgaccaacgc gaccgtaccg   1980
ctgcagctgg tgaataccac cgagccggtg gtattcatct ccttaaacgg cggccaaatg   2040
gtgcccgtgc tgctcgacac cggatccacc ggtctggtca tggacagcca attcctgacg   2100
cagaacttcg gccccgtcat cgggacgggc accgccggtt acgccggcgg gctgacctac   2160
aactacaaca cctactcaac gacggtggat ttcggcaatg gccttctcac cctgccgacc   2220
agcgttaacg tcgtcacctc gtcatcaccg ggaaccctgg gcaacttctt gtcgagatcc   2280
ggtgcggtgg gcgtcttggg aatcgggccc aacaacgggt tcccgggcac cagctccatc   2340
gttaccgcga tgcccggcct gctcaacaac ggtgtgctca tcgacgaatc ggcgggcatc   2400
ctgcagttcg gtcccaacac attaaccggc ggtatcacga tttctggagc accgatttcc   2460
accgtggctg ttcagatcga caacgggccg ctgcaacaag ctccggtgat gttcgactcc   2520
ggcggcatca acggaaccat cccgtcagcc ctcgccagcc tgccgtccgg gggattcgtg   2580
```

```
ccggcgggaa cgaccatttc ggtctacacc agcgacggcc agacgctgtt gtactcctac   2640

accaccaccg cgacaaacac cccatttgtc acctccggcg gcgtgatgaa caccgggcac   2700

gtccccttcg cgcagcaacc gatatacgtc tcctacagcc ccaccgccat cgggacgacc   2760

acctttaact ga                                                        2772
```

<210> SEQ ID NO 31
<211> LENGTH: 999
<212> TYPE: DNA
<213> ORGANISM: Mycobacterium tuberculosis

<400> SEQUENCE: 31

```
atgacccacg accacgctca ttcacgaggt gtgccggcga tgatcaagga gatcttcgcg     60

ccgcactccc acgacgccgc cgacagcgtc gacgacaccc tggaatccac tgcggcaggg    120

atccgtacgg tcaagatcag cttgttggtt ctcgggttga ccgcgctcat ccagattgtg    180

atcgtggtga tgtcggggtc ggttgcgctg gccgccgaca ccatccacaa cttcgctgat    240

gcgttgaccg cggtgccgtt gtggatcgcg ttcgcgttgg gcgccaagcc cgccactcgc    300

cgatatacct acggattcgg tcgcgtcgag gacctggccg ggtcgttcgt ggtcgcgatg    360

atcacgatgt cggccatcat cgccggttac gaagccatcg cccgcctgat ccacccgcag    420

cagatcgagc atgtcggctg ggtcgccctg gccgggctgg tcggattcat cggcaacgag    480

tgggttgccc tctaccgcat cagggttggg caccgcatcg gctcggccgc cctgatcgcc    540

gacggactac acgctcgaac cgacggattc acctcgctgg ccgtgctgtg ctcggccggc    600

ggtgtcgcac ttgggttccc actggccgac cccatcgtcg gcctgctcat cacggcggcg    660

attctggccg tgctacgaac tgccgcgcga gatgtgttcc gccgcctgct cgacggcgtc    720

gacccagcga tggtcgatgc cgccgaacaa gccctggcgg cccggcccgg cgtgcaggcg    780

gtacgcagcg tgcggatgcg ctggatcgga caccgcttgc acgccgatgc cgaactcgac    840

gtcgaccccg ccctggacct cgcgcaagct caccgcatcg cccacgacgc cgaacacgaa    900

ctcacccaca ccgttcccaa gctgaccacc gccctcatcc acgcctatcc ggctgaacat    960

ggctcgtcga tcccagatcg tggccgcacc gtagagtga                           999
```

<210> SEQ ID NO 32
<211> LENGTH: 1848
<212> TYPE: DNA
<213> ORGANISM: Mycobacterium tuberculosis

<400> SEQUENCE: 32

```
gtggtgaatt tttcggtgtt gccgccggag attaattcgg ggcggatgtt ttttggtgcg     60

gggtcggggc cgatgttggc ggcggcggcg gcctgggatg ggttggcggc tgagttgggg    120

ttggcggcgg agtcgtttgg gttggtgacc tcgggtctgg cgggtgggtc gggtcaggcg    180

tggcagggtg cggcggcggc ggcgatggtg gtggcggcgg cgccgtatgc ggggtggttg    240

gctgctgcgg cggcgcgggc tggggggggct gcggttcagg ctaaggcggt ggccggcgcg    300

tttgaggcgg cgcgggcggc catggtggat ccggtggtgg tggcggctaa tcgcagtgcg    360

tttgtgcagt tggtgctgtc gaatgtgttt gggcagaatg cgccggcgat tgccgctgct    420

gaggccacct atgagcagat gtgggctgcc gatgtggcgg cgatggtggg ttatcacggt    480

ggggcatcgg cggcggcggc ggcgttggcg ccatggcagc aggcggtgcc gggcttgtcg    540

ggcttgctag gcggtgcggc taacgcaccg gcggccgctg cacaaggcgc tgcacaaggc    600

ctcgccgagc tgaccttgaa tttgggtgtc ggcaacatcg gcagcctcaa cctgggcagc    660
```

-continued

```
ggcaacatcg gcggtaccaa cgtgggcagt ggcaatgtcg gcggcaccaa cctgggcagc    720

gggaactacg gcagcctgaa ctggggcagc ggaaacaccg gtaccggcaa tgccggcagc    780

ggaaacacgg gtgactacaa ccctggcagc ggaaacttcg gcagcggaaa cttcggcagc    840

ggaaatatcg gcagcctcaa tgtgggcagc ggaaacttcg gcacgctcaa cctcgccaac    900

ggaaataacg gtgatgtcaa tttcggcggc gggaacaccg gcgacttcaa ctttggcggc    960

gggaataatg gcaccctcaa ctttgggttc ggaaacaccg gcagcgggaa tttcggtttc   1020

ggaaacacgg gcaacaacaa tatcggtatc gggctcaccg gtgatggtca gatcggcatc   1080

ggcggactga actcaggcac tggaaacatc ggcttcggaa actccggcaa caacaacatc   1140

ggcttcttca actcgggtga tggaaacatc ggcttcttca actcgggtga cggcaacacg   1200

ggtttcggga acgccggaaa tatcaacacc ggtttctgga acgcaggcaa tttaaacacg   1260

ggcttcggga gtgccggcaa cggaaacgtc ggtatcttcg acggcgggaa ctcaaactcg   1320

ggcagcttca acgtgggctt tcagaacacc ggcttcggaa attcgggtgc tggaaacacc   1380

ggcttcttca atgcgggtga ctcgaacacc ggtttcgcga acgcaggtaa cgtcaacacc   1440

ggtttcttta acggtggaga tatcaacacc ggtggtttca atggcggcaa cgtcaacacc   1500

ggttttggca gcgcgctcac ccaagcaggt gccaactcgg gcttcgggaa cctcggtacc   1560

ggcaactcgg gttgggggaa cagtgacccc tcgggcaccg gcaactccgg gttcttcaac   1620

acaggcaacg gtaattcggg cttctccaac gccggcccag ccatgcttcc tggcttcaac   1680

tccgggtttg caaacattgg ctctttcaat gcaggaattg caaactcggg taacaacctc   1740

gccggtatct ccaactcggg tgacgacagt tcgggtgcgg taaattcggg tagccagaac   1800

tccggtgctt tcaatgcggg tgtaggactt tcgggattct tcaggtag                1848
```

<210> SEQ ID NO 33
<211> LENGTH: 1773
<212> TYPE: DNA
<213> ORGANISM: Mycobacterium tuberculosis

<400> SEQUENCE: 33

```
atgaattatt cggtgttgcc gccggagatt aattcgttgc ggatgtttac cggtgcgggg     60

tctgcgccga tgcttgcggc atcggtggct tgggatcgtt tggccgcgga gttggcggtg    120

gcggcgtcct cgtttgggtc ggtgacttcg ggggttggcgg gtcagtcctg gcagggtgcg    180

gcggcggcgg cgatggccgc ggcggcggcg ccgtatgcgg ggtggttggc tgctgcggcg    240

gcgcgggccg ctggcgcgtc ggctcaggcc aaggcggtgg ccagtgcgtt tgaggcggcg    300

cgggcggcga cggtgcatcc gatgctggtg gcggccaacc gtaatgcgtt tgtgcagttg    360

gtgttgtcga atctgtttgg gcagaatgcg ccggcgatcg cggccgctga ggcgatgtat    420

gaacagatgt gggccgccga tgtggccgcg atggtgggct atcacggcgg ggcatcggcg    480

gccgcggcgc agctgtcgtc gtggtcaatt ggtctgcagc aggcgttgcc agctgcgcca    540

tcggcgctgg ccgccgcgat cggcctcggc aacatcggcg tcgggaacct gggcggcggg    600

aacaccggtg actacaatct gggcagcgga aattccggca acgccaacgt aggtagcgga    660

aactccggca acgccaatgt gggcagcgga aatgacggtg ccacgaattt gggcagcgga    720

aatatcggca acaccaatct cggcagcgga aacgttggca atgtcaatct gggcagcgga    780

aaccgaggct ttggaaacct cggcaacgga aactttggca gtgggaacct gggcagtgga    840

aacaccggaa gtaccaactt cggcggcgga aatctcggtt ccttcaactt gggcagtgga    900
```

-continued

```
aacatcggct cctccaacat cggtttcgga aacaacggcg acaataacct cggcctcggg    960
aacaatggca acaacaacat cggttttggg ctcaccggcg acaacttggt gggcattggc   1020
gcgctgaact cgggcatcgg gaatctaggt ttcgggaact cgggtaacaa caacatcggt   1080
ttcttcaact ctggcaacaa caacgtgggc ttcttcaatt cgggcaacaa caacttcggc   1140
tttggaaacg cgggcgacat caacacgggc ttcggaaacg ccggcgacac caacacgggc   1200
ttcggaaacg ccggcttctt caatatgggc atcgggaacg cgggcaacga agacatgggc   1260
gtcgggaacg gcggttcctt taacgtgggc gttggcaatg cgggcaacca aagtgtgggc   1320
tttggcaacg cgggcaccct aaacgtgggc ttcgcaaacg cgggcagtat caatacggga   1380
ttcgcgaact cgggcagcat caatacgggc ggtttcgact cgggcgaccg gaacaccggg   1440
tttggaagct cggtcgacca atccgtttcg agctcgggct tcggcaacac cggcatgaat   1500
tcctcaggct tctttaacac gggcaatgtt tcggctggct atgggaacaa cggtgacgtt   1560
cagtcgggca tcaataacac caactccggc ggcttcaacg tcggcttcta taactcgggt   1620
gccggcaccg tgggcatcgc aaactctggc ctgcagacca caggcattgc gaactcgggc   1680
accctcaaca cgggtgtggc gaacacgggt gaccacagct cgggggcctt caatcagggc   1740
agtgaccagt cgggcttctt cggtcagccc taa                                1773
```

<210> SEQ ID NO 34
<211> LENGTH: 927
<212> TYPE: DNA
<213> ORGANISM: Mycobacterium tuberculosis

<400> SEQUENCE: 34

```
atgtcgtttg tgttcgcggc gccagaggca ctggcggcgg ccgctgcgga catggccggt     60
atcggttcga ctcttaacgc cgccaatgtg gttgcggcgg ttcccaccac cggagtcctg    120
gccgcagccg cggacgaggt ctcgactcag gtcgccgcgc tgctttccgc gcatgctcag    180
gggtatcagc agctcagccg gcagatgatg acagccttcc acgaccagtt cgtgcaggcg    240
ctgagagcaa gtgcagacgc gtatgcaacc gccgaggcca gcgccgcgca gaccatggtg    300
aacgccgtga atgcgcccgc aagagcgttg ctggggcatc cactgattag cgccgacgcc    360
tcgacgggtg gggctcgaa cgcgctgagc cgggtccaaa gcatgttcct cggcactggc    420
ggctccagtg cacttggcgg tagcgccgct gcaaatgccg ctgccagcgg tgcactgcag    480
ctccaaccca ccggtggggc cagcggtttg tccgccgtcg gcgccctgct gccgcgcgcc    540
ggagcggccg ccgccgcggc gctgccggct ctggccgccg agtcgatcgg caacgcaatc    600
aagaatctct acaacgccgt cgaaccgtgg gtgcagtacg gcttcaacct caccgcatgg    660
gcggtgggat ggctgcccta catcggcata ctggcaccgc agatcaactt cttctattac    720
ctcggcgagc ccatcgtgca ggcagtcctg ttcaatgcga tcgacttcgt ggacgggaca    780
gtcactttca gccaggcact aaccaatatc gaaacggcca ccgcggcatc gatcaaccaa    840
ttcatcaaca ccgagatcaa ctggatacgc ggcttcctgc cgccgttgcc gccaatcagc    900
ccgccgggat tcccgtcttt gccctaa                                        927
```

<210> SEQ ID NO 35
<211> LENGTH: 399
<212> TYPE: DNA
<213> ORGANISM: Mycobacterium tuberculosis

<400> SEQUENCE: 35

```
atggactacg cgttcttacc accggagatc aactccgcgc gtatgtacag cggtcccgga     60
```

```
ccgaattcaa tgttggttgc cgcggccagc tgggatgcgc tggccgcgga gttagcatcc    120

gcagcagaga actacggctc ggtgattgcg cgtctgaccg gtatgcactg gtggggcccg    180

gcgtccacgt cgatgctggc catgtcggct ccatacgtgg aatggctgga gcggaccgcc    240

gcgcagacca agcagaccgc tacccaagcc agagcggcgg cggcggcatt cgagcaggct    300

catgcgatga cggtgccccc agcgttggtc acaggcatcc ggggtgccat cgtcgtcgaa    360

acggccagtg ccagcaacac cgctggcact ccaccttga                           399
```

<210> SEQ ID NO 36
<211> LENGTH: 2718
<212> TYPE: DNA
<213> ORGANISM: Mycobacterium tuberculosis

<400> SEQUENCE: 36

```
ttgtcggcgt cagtgtctgc cacgacggct catcatggct tgccagcaca tgaagtggtg     60

ctgctgctgg agagcgatcc atatcacggg ctgtccgacg gcgaggccgc ccaacgacta    120

gaacgcttcg ggcccaacac cttggcggtg gtaacgcgcg ctagcttgct ggcccgcatc    180

ctgcggcagt ttcatcaccc gctgatctac gttctgctcg ttgccgggac gatcaccgcc    240

ggtcttaagg aattcgttga cgccgcagtg atcttcggtg tggtggtgat caatgcgatc    300

gtgggtttca ttcaagaatc caaggcagag gccgcactgc agggcctgcg ctccatggtg    360

cacacccacg ccaaggtggt gcgcgagggt cacgagcaca caatgccatc cgaagagctg    420

gttcccggtg accttgtgct gttagcggcc ggtgacaagg ttcccgccga tttgcggctg    480

gtgcgacaga ccggattgag cgtgaacgag tcagcactta ccggcgagtc gacgccggtt    540

cacaaggacg aggtggcgtt gccggagggc acaccggtcg ctgatcgtcg caatatcgcg    600

tattccggca cattggtaac cgcgggccat ggcgccggga tcgtcgtcgc gaccggcgcc    660

gaaaccgaac tcggtgagat tcatcggctc gttggggccg ccgaggttgt cgccacaccg    720

ctgaccgcga agctggcgtg gttcagcaag tttctgacca tcgccatcct gggtctggca    780

gcgctcacgt tcggcgtggg tttgctgcgc cggcaagatg ccgtcgaaac gttcaccgct    840

gcgatcgcgc tggcggtcgg ggcaattccc gaaggtctgc ccaccgccgt gaccatcacc    900

ttggccatcg gcatggcccg gatggccaag cgccgcgcgg tcattcgacg tctacccgcg    960

gtggaaacgc tgggcagcac cacggtcatc tgcgccgaca agaccggaac gctgaccgag   1020

aatcagatga cggtccagtc gatctggaca ccccacggtg agatccgggc gaccggaacg   1080

ggctatgcac ccgacgtcct cctgtgcgac accgacgacg cgccggttcc ggtgaatgcc   1140

aatgcggccc ttcgctggtc gctgctggcc ggtgcctgca gcaacgacgc cgcactggtt   1200

cgcgacggca cacgctggca gatcgtcggc gatcccaccg agggcgcgat gctcgtcgtg   1260

gccgccaagg ccggcttcaa cccggagcgg ctggcgacaa ctctgccgca agtggcagcc   1320

ataccgttca gttccgagcg gcaatacatg gccaccctgc atcgcgacgg gacggatcat   1380

gtggtgctgg ccaagggtgc tgtggagcgc atgctcgacc tgtgcggcac cgagatgggc   1440

gccgacggcg cattgcggcc gctggaccgc gccaccgtgt tgcgtgccac cgaaatgttg   1500

acttcccggg ggttgcgggt gctggcaacc gggatgggtg ccggcgccgg cactcccgac   1560

gacttcgacg aaaacgtgat accaggttcg ctggcgctga ccggcctgca agcgatgagc   1620

gatccaccac gagcggccgc ggcatcggcg gtggcggcct gccacagtgc cggcattgcg   1680

gtaaaaatga ttaccggtga ccacgcgggc accgccacgg cgatcgcaac cgaggtgggg   1740
```

-continued

| | | | | | | |
|---|---|---|---|---|---|---|
| ttgctcgaca | acactgaacc | ggcggcaggc | tcggtcctga | cgggtgccga | gctggccgcg | 1800 |
| ctgagcgcag | accagtaccc | ggaggccgtg | gatacagcca | gcgtgtttgc | cagggtctct | 1860 |
| cccgagcaga | agctgcggtt | ggtgcaagca | ttgcaggcca | gggggcacgt | cgtcgcgatg | 1920 |
| accggcgacg | gcgtcaacga | cgccccggcc | ttgcgtcagg | ccaacattgg | cgtcgcgatg | 1980 |
| ggccgcggtg | gcaccgaggt | cgccaaggat | gccgccgaca | tggtgttgac | cgacgacgac | 2040 |
| ttcgccacca | tcgaagccgc | ggtcgaggaa | ggccgcggcg | tattcgacaa | tctgaccaag | 2100 |
| ttcatcacct | ggacgctgcc | caccaacctc | ggtgagggcc | tagtgatctt | ggccgccatc | 2160 |
| gctgttggcg | tcgccttgcc | gattctgccc | acccaaattc | tgtggatcaa | catgaccaca | 2220 |
| gcgatcgcgc | tcggactcat | gctcgcgttc | gagcccaagg | aggccggaat | catgacccgg | 2280 |
| ccaccgcgcg | accccgacca | accgctgctg | accggctggc | ttgtcaggcg | gactcttctg | 2340 |
| gtttccacct | tgctcgtcgc | cagcgcgtgg | tggctgtttg | catgggagct | cgacaatggc | 2400 |
| gcgggcctgc | atgaggcgcg | cacggcggcg | ctgaacctgt | tcgtcgtcgt | cgaggcgttc | 2460 |
| tatctgttca | gctgccggtc | gctgacccga | tcggcctggc | ggctcggcat | gttcgccaac | 2520 |
| cgctggatca | tcctcggcgt | cagtgcgcag | gccatcgcgc | aattcgcgat | cacatatcta | 2580 |
| cccgcgatga | atatggtgtt | cgacaccgcg | ccaatcgata | tcggggtgtg | ggtgcgcata | 2640 |
| ttcgctgtcg | cgaccgcaat | cacgattgtg | gtggccaccg | acacgctgct | gccgagaata | 2700 |
| cgggcgcaac | cgccatga | | | | | 2718 |

METHODS FOR PRODUCING AN IMMUNE RESPONSE TO TUBERCULOSIS

CROSS REFERENCE TO RELATED APPLICATIONS

This is a divisional of U.S. patent application Ser. No. 14/590,810, filed on Jan. 6, 2015, which is a continuation of U.S. patent application Ser. No. 13/510,862, filed on May 18, 2012, now issued as U.S. Pat. No. 8,961,989, which is the §371 U.S. National Stage of International Application No. PCT/US2010/057479, filed Nov. 19, 2010, which was published in English under PCT Article 21(2), which in turn claims the benefit of U.S. Provisional Application No. 61/263,206, filed Nov. 20, 2009. The prior applications are incorporated herein by reference in their entirety.

ACKNOWLEDGMENT OF GOVERNMENT SUPPORT

This invention was made with government support under Grant No. HSSN266200400081C awarded by the National Institutes of Health. The government has certain rights in the invention.

FIELD

This application relates to the field of immunology, more specifically to methods for the production of an immune response to tuberculosis antigens in a subject.

BACKGROUND

*Mycobacterium* is a genus of aerobic intracellular bacterial organisms that, upon infection of a host, survive within endosomal compartments of monocytes and macrophages. Human mycobacterial diseases include tuberculosis (caused by *M. tuberculosis*), leprosy (caused by *M. leprae*), Bairnsdale ulcers (caused by *M. ulcerans*), and various infections caused by *M. marinum, M. kansasii, M. scrofulaceum, M. szulgai, M. xenopi, M. fortuitum, M. chelonae, M. haemophilum* and *M. intracellulare* (see Wolinsky, Chapter 37 in Microbiology: Including Immunology and Molecular Genetics, 3rd Ed., Harper & Row, Philadelphia, 1980).

One third of the world's population harbors *M. tuberculosis* and is at risk for developing tuberculosis (TB). In immunocompromised patients, tuberculosis is increasing at a nearly logarithmic rate, and multidrug resistant strains are appearing. In addition, mycobacterial strains which were previously considered to be nonpathogenic strains (e.g., *M. avium*) have now become major killers of immunosuppressed AIDS patients. Moreover, current mycobacterial vaccines are either inadequate (such as the BCG vaccine for *M. tuberculosis*) or unavailable (such as for *M. leprae*) (Kaufmann, *Microbiol. Sci.* 4:324-328, 1987; U.S. Congress, Office of Technology Assessment, The Continuing Challenge of Tuberculosis, pp. 62-67, OTA-H-574, U.S. Government Printing Office, Washington, D.C., 1993).

Inhibiting the spread of tuberculosis requires effective vaccination and accurate, early diagnosis of the disease. Currently, vaccination with live bacteria is the most efficient method for inducing protective immunity. The most common *mycobacterium* employed for this purpose is *Bacillus* Calmette-Guerin (BCG), an avirulent strain of *Mycobacterium bovis*. However, the safety and efficacy of BCG is a source of controversy and some countries, such as the United States, do not vaccinate the general public.

*Mycobacterium tuberculosis* (Mtb)-specific $CD4^+$ and $CD8^+$ T cells are critical for the effective control of Mtb infection. In the mouse model, passive transfer of $CD4^+$ T cells to sublethally irradiated animals renders them less susceptible to Mtb infection (Orme, *J. Immunol.* 140:3589-3593, 1988). Mice in which the gene(s) for CD4 or for MHC Class II molecules are disrupted, as well as wild-type mice depleted of $CD4^+$ T cells, demonstrate increased susceptibility to Mtb infection (Flory et al., *J. Leukoc. Biol.* 51:225-229, 1992). In humans, human immunodeficiency virus-infected individuals are exquisitely susceptible to developing TB after exposure to Mtb, supporting an essential role for $CD4^+$ T cells (Hirsch et al., *J. Infect. Dis.* 180:2069-2073, 1999). $CD8^+$ T cells are also important for effective T cell immunity (see Lazarevic and Flynn, *Am. J. Respir. Crit. Care Med.* 166:1116-1121, 2002). In humans, Mtb-specific $CD8^+$ T cells have been identified in Mtb-infected individuals and include $CD8^+$ T cells that are both classically HLA-Ia restricted (see, for example, Lewinsohn et al., *J. Immunol.* 165:925-930, 2000) and nonclassically restricted by the HLA-Ib molecule HLA-E (Lewinsohn et al., *J. Exp. Med.* 187:1633-1640, 1998). However, there are no vaccines or therapeutic strategies that effectively induce an immune response, such as a CD8 response, to Mtb.

SUMMARY

Accordingly, there is a need in the art for agents that can produce an immune response to Mtb that can be used for treatment and/or protection from an Mtb infection.

Methods for producing an immune response to *Mycobacterium tuberculosis* (Mtb) are disclosed herein. Methods for treating an Mtb infection, inhibiting an Mtb infection, or preventing an Mtb infection in a subject, are also disclosed herein. The Mtb infection can be latent or active.

In several embodiments, the methods include administering to the subject a therapeutically effective amount of a polypeptide, or a polynucleotide encoding the polypeptide, wherein the polypeptide comprises at least one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18. In additional embodiments, the methods include administering to the subject a therapeutically effective amount of a polypeptide comprising at least nine to twenty consecutive amino acids of at least one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18, wherein the nine to twenty consecutive amino acids specifically bind major histocompatibility complex (MHC) class I. In some examples, the polypeptide includes a conservative variant of the polypeptide (for example, one or more conservative amino acid substitutions). In several examples, the immune response is a protective immune response. In additional embodiments, methods are disclosed for inhibiting or preventing an infection with Mtb, or treating an infection with Mtb.

Isolated polypeptides are described herein that include nine to twenty consecutive amino acids of at least one of the amino acid sequences set forth as SEQ ID NOs: 1-18, wherein the nine to twenty consecutive amino acids specifically bind major histocompatibility complex (MHC) class I, wherein the isolated polypeptide does not include any of the full length amino acid sequences set forth as SEQ ID NOs: 1-18. Nucleic acids encoding these polypeptides, vectors including these nucleic acids, host cells including these nucleic acids, and immunogenic compositions including these polypeptides, nucleic acids and/or host cells are also disclosed. Pharmaceutical compositions including a therapeutically effective amount of these polypeptides, nucleic acids, and/or host cells are also described.

The foregoing and other features will become more apparent from the following detailed description, which proceeds with reference to the accompanying figures.

SEQUENCE LISTING

Figure 1A:
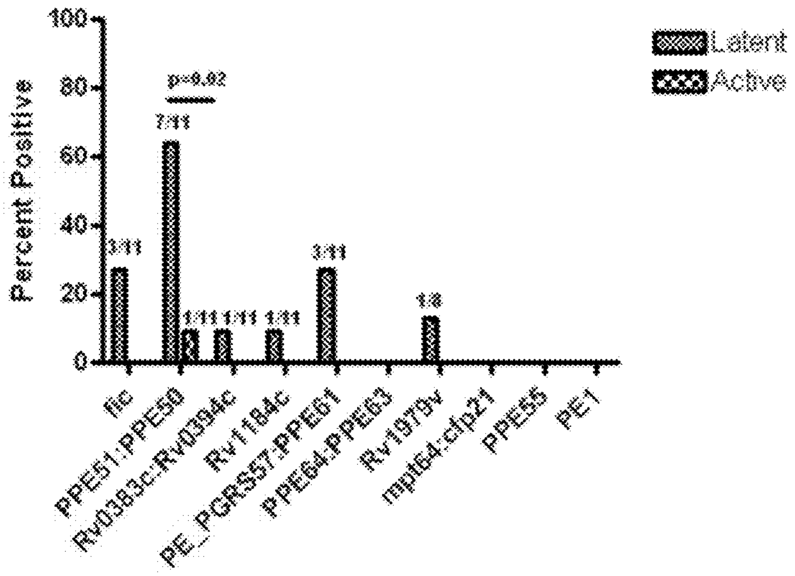
FIG. 1A is a pair of bar graphs showing percent positive samples in the ELISPOT assay for the indicated antigens in individuals with latent or active TB.
Figure 1A:
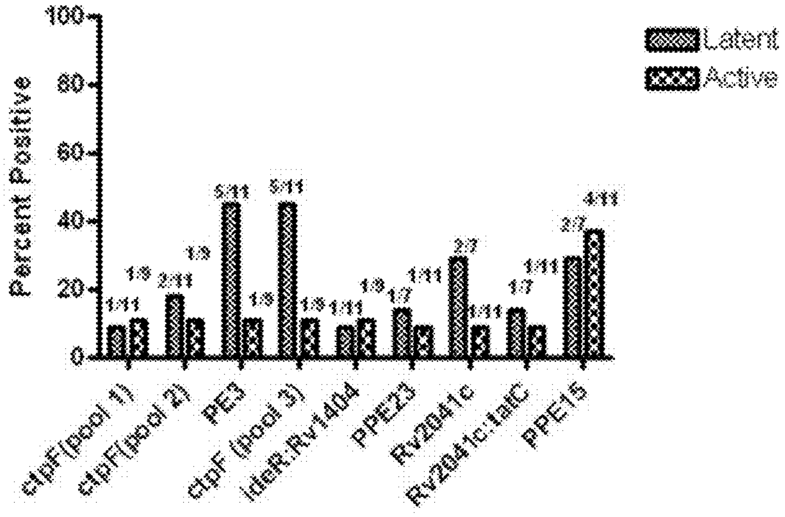
Figure 1B:
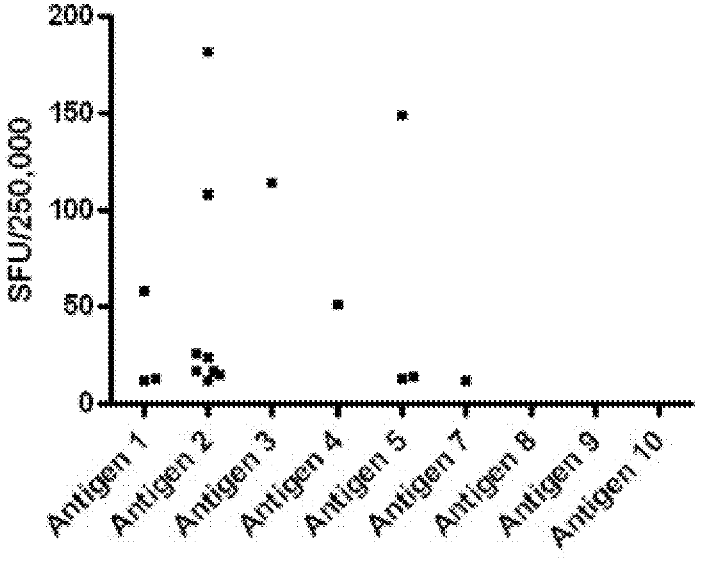
FIG. 1B is a pair of graphs showing spot forming units (SFU) for each antigen in the ELISPOT assay. The antigens are listed in Table 2.
Figure 1B:
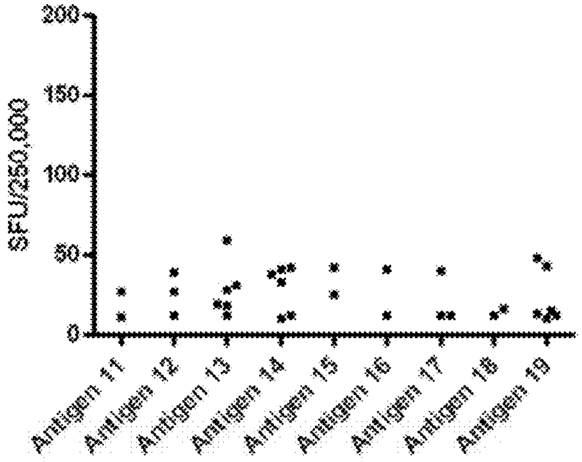

The nucleic acid and amino acid sequences listed herein or in the accompanying sequence listing are shown using standard letter abbreviations for nucleotide bases, and one letter code for amino acids. Only one strand of each nucleic acid sequence is shown, but the complementary strand is understood as included by any reference to the displayed strand.

The Sequence Listing is submitted as an ASCII text file in the form of the file named 899-81443-15_Sequence_Listing.txt, Oct. 17, 2016, and is 117 KB, which is incorporated by reference herein.

SEQ ID NOs: 1-18 are the amino acid sequences of Mtb polypeptides.

SEQ ID NOs: 19-36 are the nucleic acid sequences of polynucleotides encoding the Mtb polypeptides.

DETAILED DESCRIPTION

Methods for producing an immune response to *Mycobacterium tuberculosis* (Mtb) are disclosed herein. In several examples, the immune response is a protective immune response. In additional embodiments, methods are disclosed for inhibiting an infection with Mtb, or treating an infection with Mtb. Pharmaceutical compositions for the inhibition, prevention and/or treatment of tuberculosis are also disclosed.

I. Abbreviations

APC: antigen presenting cell
BCG: *Bacillus* Calmette-Guerin
DC: dendritic cell
HLA: human leukocyte antigen
IFN-γ: interferon-γ
MHC: major histocompatibility complex
Mtb: *Mycobacterium tuberculosis*
TB: tuberculosis

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages) Immunostimulatory oligonucleotides (such as those including a CpG motif) can also be used as adjuvants (for example see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199). Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L and 4-1 BBL Amplification: Use of a technique that increases the number of copies of a nucleic acid molecule (e.g., a DNA or RNA molecule) in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: Immunoglobulin molecules and immunologically active portions of immunoglobulin molecules, i.e., molecules that contain an antigen binding site that specifically binds (immunoreacts with) an antigen, such as an Mtb polypeptide.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and CH1 domains; (ii) an $F_d$ fragment consisting of the VH and CH1 domains; (iii) an Fv fragment consisting of the $V_L$ and $V_H$ domains of a single arm of an antibody, (iv) a dAb fragment (Ward et al., *Nature* 341:544-546, 1989) which consists of a VH domain; (v) an isolated complementarity determining region (CDR); and (vi) a $F(ab)_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055 and 4,444,487; WO 88/03565; EP 256,654; EP 120,694; EP 125,023; Falkner et al., *Nature* 298:286, 1982; Morrison, *J. Immunol.* 123:793, 1979; Morrison et al., *Ann. Rev. Immunol.* 2:239, 1984).

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease-specific antigen. A tissue-specific antigen is expressed in a limited number of tissues, such as a single tissue. A tissue-specific antigen may be expressed by more than one tissue, such as, but not limited to, an antigen that is expressed in more than one reproductive tissue, such as in both prostate and uterine tissue. A disease-specific antigen is expressed coincidentally with a disease process. Specific non-limiting examples of a disease-specific antigen are an antigen whose expression correlates with, or is predictive of, tuberculosis. A disease-specific antigen can be an antigen recognized by T cells or B cells.

Antigen presenting cell (APC): A cell that can present an antigen to T cell, such that the T cells are activated. Dendritic cells (DCs) are the principle APCs involved in primary immune responses. Their major function is to obtain antigen in tissues, migrate to lymphoid organs and present the antigen in order to activate T cells.

When an appropriate maturational cue is received, DCs are signaled to undergo rapid morphological and physiological changes that facilitate the initiation and development of immune responses. Among these are the up-regulation of molecules involved in antigen presentation; production of pro-inflammatory cytokines, including IL-12, key to the generation of Th1 responses; and secretion of chemokines that help to drive differentiation, expansion, and migration of surrounding naive Th cells. Collectively, these up-regulated molecules facilitate the ability of DCs to coordinate the activation and effector function of other surrounding lymphocytes that ultimately provide protection for the host.

cDNA (complementary DNA): A piece of DNA lacking internal, non-coding segments (introns) and regulatory sequences that determine transcription. cDNA is synthesized in the laboratory by reverse transcription from messenger RNA extracted from cells.

CD4: Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8: Cluster of differentiation factor 8, a T cell surface protein that mediates interaction with the MHC Class I molecule. Cells that express CD8 are often cytotoxic T cells. "$CD8^+$ T cell mediated immunity" is an immune response implemented by presentation of antigens to $CD8^+$ T cells.

Conservative variants: A substitution of an amino acid residue for another amino acid residue having similar biochemical properties. "Conservative" amino acid substitutions are those substitutions that do not substantially affect or decrease an activity or antigenicity of the *Mycobacterium* polypeptide. A peptide can include one or more amino acid substitutions, for example 1-10 conservative substitutions, 2-5 conservative substitutions, 4-9 conservative substitutions, such as 1, 2, 5 or 10 conservative substitutions. Specific, non-limiting examples of a conservative substitution include the following examples (Table 1).

TABLE 1

Exemplary conservative amino acid substitutions

| Original Amino Acid | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide, or that an immune response can be generated against the substituted polypeptide that is similar to the immune response against the unsubstituted polypeptide, such as a *Mycobacterium* antigen. Thus, in one embodiment, non-conservative substitutions are those that reduce an activity or antigenicity.

Consists Essentially Of/Consists Of: With regard to a polypeptide, a polypeptide consists essentially of a specified amino acid sequence if it does not include any additional amino acid residues. However, the polypeptide can include additional non-peptide components, such as labels (for example, fluorescent, radioactive, or solid particle labels), sugars or lipids. A polypeptide that consists of a specified amino acid sequence does not include any additional amino acid residues, nor does it include additional non-peptide components, such as lipids, sugars or labels.

Contacting: The process of incubating one agent in the presence of another. Thus, when a cell is contacted with an agent, the cell is incubated with the agent for a sufficient period of time for the agent and the cell to interact.

Costimulatory molecule: Although engagement of the T cell receptor with peptide-MHC delivers one signal to the T cell, this signal alone can be insufficient to activate the T cell. Costimulatory molecules are molecules that, when bound to their ligand, deliver a second signal required for the T cell to become activated. The most well-known costimulatory molecule on the T cell is CD28, which binds to either B7-1 (also called CD80) or B7-2 (also known as CD86). An additional costimulatory molecule is B7-3. Accessory molecules that also provide a second signal for the activation of T cells include intracellular adhesion molecule (ICAM-1 and ICAM-2), leukocyte function associated antigen (LFA-1, LFA-2 and LFA-3). Integrins and tumor necrosis factor (TNF) superfamily members can also serve as costimulatory molecules.

Cytokine: Proteins made by cells that affect the behavior of other cells, such as lymphocytes. In one embodiment, a cytokine is a chemokine, a molecule that affects cellular trafficking. Specific, non-limiting examples of cytokines include the interleukins (IL-2, IL-4, IL-6, IL-10, IL-21, etc.), and interferon (IFN)-γ.

Degenerate variant: A polynucleotide encoding an epitope of an Mtb polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the Mtb polypeptide encoded by the nucleotide sequence is unchanged.

Dendritic cell (DC): Dendritic cells are the principle APCs involved in primary immune responses. DCs include plasmacytoid dendritic cells and myeloid lymphoid organs and present the antigen in order to activate T cells. Immature DCs originate in the bone marrow and reside in the periphery as immature cells.

Displaying: The process of localizing a peptide:antigen complex, or a peptide, on the outer surface of a cell where the peptide:antigen complex or peptide is accessible to a second cell, molecules displayed by a second cell, or soluble factors. A peptide, or a peptide:antigen complex, is "displayed" by a cell when it is present on the outer surface of the cell and is accessible to a second cell, to molecules displayed by the second cell, or to soluble factors.

Epitope: An antigenic determinant. These are particular chemical groups or peptide sequences on a molecule that are antigenic, e.g., that elicit a specific immune response. An antibody specifically binds a particular antigenic epitope on a polypeptide, such a *Mycobacterium* polypeptide.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (e.g., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5 or 3' regions of the gene. Both constitutive and inducible promoters, are included (see e.g., Bitter et al., *Meth. Enzymol.* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. In one embodiment, the promoter is a cytomegalovirus promoter.

Functionally Equivalent: Sequence alterations, such as in an epitope of an antigen, which yield the same results as described herein. Such sequence alterations can include, but are not limited to, conservative substitutions, deletions, mutations, frameshifts, and insertions.

Heterologous: Originating from separate genetic sources or species. A polypeptide that is heterologous to an Mtb polypeptide originates from a nucleic acid that does not encode the Mtb polypeptide or another Mtb polypeptide. In one specific, non-limiting example, a polypeptide comprising nine consecutive amino acids from an Mtb polypeptide, or at most 20 consecutive amino acids from the Mtb polypeptide, and a heterologous amino acid sequence includes a β-galactosidase, a maltose binding protein, and albumin, hepatitis B surface antigen, or an immunoglobulin amino acid sequence. Generally, an antibody that specifically binds to a protein of interest will not specifically bind to a heterologous protein.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term “host cell” is used.

Human Leukocyte Antigen (HLA): A genetic designation of the human major histocompatibility complex (MHC). Individual loci are designated by uppercase letters, as in HLA-E, and alleles are designated by numbers, as in HLA-A*0201. The three main MHC class I genes are called HLA-A, HLA-B, and HLA-C. However, there are many genes that encode β2 microglobulin-associated cell surface molecules that are linked to the MHC class I genes. The expression of these genes is variable, both in the tissue distribution and the amount expressed on cells; these genes have been termed the MHC class IB genes.

Immune response: A response of a cell of the immune system, such as a B cell, natural killer cell, or a T cell, to a stimulus. In one embodiment, the response is specific for a particular antigen (an “antigen-specific response”). In one embodiment, an immune response is a T cell response, such as a Th1, Th2, or Th3 response. In another embodiment, an immune response is a response of a suppressor T cell.

Immunogenic composition: A composition comprising an effective amount of an immunogenic Mtb polypeptide or a nucleic acid encoding the immunogenic Mtb polypeptide that induces a measurable T response against Mtb, such as a $CD8^+$ T cell response, or induces a measurable B cell response (such as production of antibodies that specifically bind an Mtb polypeptide). For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and/or immunogenic polypeptide in pharmaceutically acceptable carriers and/or other agents. An immunogenic composition can optionally include an adjuvant, a costimulatory molecule, or a nucleic acid encoding a costimulatory molecule. An Mtb polypeptide, or nucleic acid encoding the polypeptide, can be readily tested for its ability to induce a $CD8^+$ T cell response.

Immunogenic peptide: A peptide which comprises an allele-specific motif or other sequence such that the peptide will bind an MHC molecule and induce a T cell response, such as a $CD8^+$ or $CD4^+$ T cell response, or a B cell response (such as antibody production) against the antigen from which the immunogenic peptide is derived.

In one embodiment, immunogenic peptides are identified using sequence motifs or other methods, such as neural net or polynomial determinations, known in the art. Typically, algorithms are used to determine the “binding threshold” of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a “conserved residue” is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein and by their ability to stimulate CD4 and/or CD8 when presented in the context of the MHC protein. In one example, an immunogenic “Mtb peptide” is a series of contiguous amino acid residues from the Mtb protein generally between 9 and 20 amino acids in length, such as about 8 to 11 residues in length.

Generally, immunogenic Mtb polypeptides can be used to induce an immune response in a subject, such as a B cell response or a T cell response. In one example, an immunogenic Mtb polypeptide, when bound to a MHC Class I molecule, activates $CD8^+$ T cells, such as cytotoxic T lymphocytes (CTLs) against Mtb. Induction of CTLs using synthetic peptides and CTL cytotoxicity assays are known in the art (see U.S. Pat. No. 5,662,907, which is incorporated herein by reference). In one example, an immunogenic peptide includes an allele-specific motif or other sequence such that the peptide will bind an MHC molecule and induce a $CD8^+$ response against the antigen from which the immunogenic peptide is derived. A $CD8^+$ T cell that specifically recognizes an Mtb polypeptide is activated, proliferates, and/or secretes cytokines in response to that specific polypeptide, and not to other, non-related polypeptides.

Inhibiting or treating a disease: Inhibiting a disease, such as tuberculosis, refers to inhibiting the full development of a disease. In several examples, inhibiting a disease refers to lessening symptoms of a tuberculosis. “Treatment” refers to a therapeutic intervention that ameliorates a sign or symptom of a disease or pathological condition related to the disease, such as tuberculosis.

Interferon gamma (IFN-γ): IFN-γ is a dimeric protein with subunits of 146 amino acids. The protein is glycosylated at two sites, and the pI is 8.3-8.5. IFN-γ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-γ with respect to molecular mass and charge are due to variable glycosylation patterns. 40-60 kDa forms observed under non-denaturing conditions are dimers and tetramers of IFN-γ. The human gene has a length of approximately 6 kb. It contains four exons and maps to chromosome 12q24.1.

IFN-γ can be detected by sensitive immunoassays, such as an ELSA test that allows detection of individual cells producing IFN-γ. Minute amounts of IFN-γ can be detected indirectly by measuring IFN-induced proteins such as Mx protein. The induction of the synthesis of IP-10 has also been used to measure IFN-γ concentrations. In addition, bioassays can be used to detect IFN-γ, such as an assay that employs induction of indoleamine 2,3-dioxygenase activity in 2D9 cells. The production of IFN-γ can be used to assess T cell activation, such as activation of a T cell by a *Mycobacterium* antigen.

Isolated: An “isolated” biological component (such as a nucleic acid molecule, protein, or organelle) has been substantially separated or purified away from other biological components in the cell of the organism in which the component naturally occurs, such as other chromosomal and extra-chromosomal DNA and RNA, proteins, and organelles. Nucleic acids and proteins that have been “isolated” include nucleic acids and proteins purified by standard purification methods. The term also embraces nucleic acids and proteins prepared by recombinant expression in a host cell, as well as chemically synthesized nucleic acids or proteins, or fragments thereof.

Linker sequence: A linker sequence is an amino acid sequence that covalently links two polypeptide domains. Linker sequences can be included in the between the Mtb epitopes disclosed herein to provide rotational freedom to the linked polypeptide domains and thereby to promote proper domain folding and presentation to the MHC. By way of example, in a recombinant polypeptide comprising two Mtb domains, linker sequences can be provided between them, such as a polypeptide comprising Mtb polypeptide-linker-Mtb polypeptide. Linker sequences, which are generally between 2 and 25 amino acids in length, are well known in the art and include, but are not limited to, the glycine(4)-serine spacer (GGGGS ×3) described by Chaudhary et al., *Nature* 339:394-397, 1989.

Lymphocytes: A type of white blood cell that is involved in the immune defenses of the body. There are two main types of lymphocytes: B cells and T cells.

Mycobacteria: A genus of aerobic intracellular bacterial organisms. Upon invasion of a host, these organisms survive within endosomal compartments of monocytes and macrophages. Human mycobacterial diseases include tuberculosis (cause by *M. tuberculosis*), Leprosy (caused by *M. leprae*), Bairnsdale ulcers (caused by *M. ulcerans*), and other infections that can be caused by *M. marinum, M kansasii, M. scrofulaceum, M. szulgai, M. xenopi, M. fortuitum, M. haemophilum, M. chelonei*, and *M. intracelluare. Mycobacterium* strains that were previously considered to be non-pathogenic (such as *M. avium*) are also now known to be major killers of immunosuppressed AIDS patients.

The major response to mycobacteria involves cell mediated hypersensitivity (DTH) reactions with T cells and macrophages playing major roles in the intracellular killing and walling off (or containing) of the organism (granuloma formation). A major T cell response involves $CD4^+$ lymphocytes that recognize mycobacterial heat shock proteins and immunodominant antigens.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, the open reading frames are aligned.

ORF (open reading frame): A series of nucleotide triplets (codons) coding for amino acids without any termination codons. These sequences are usually translatable into a polypeptide.

Peptide Modifications: *Mycobacterium* polypeptides include synthetic embodiments of peptides described herein. In addition, analogues (non-peptide organic molecules), derivatives (chemically functionalized peptide molecules obtained starting with the disclosed peptide sequences) and variants (homologs) of these proteins can be utilized in the methods described herein. Each polypeptide of the invention is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a *Mycobacterium* polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press, Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful with the polypeptides and nucleic acids described herein are conventional. *Remington's Pharmaceutical Sciences*, by E. W. Martin, Mack Publishing Co., Easton, Pa., 19th Edition (1995), describes compositions and formulations suitable for pharmaceutical delivery of the polypeptides or polynucleotides herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A linear nucleotide sequence, including sequences of greater than 100 nucleotide bases in length.

Polypeptide: Any chain of amino acids, regardless of length or post-translational modification (e.g., glycosylation or phosphorylation). A "peptide" is a chain of amino acids that is less than 100 amino acids in length. In one embodiment, a "peptide" is a portion of a polypeptide, such as about 8-11, 9-12, or about 10, 20, 30, 40, 50, or 100 contiguous amino acids of a polypeptide that is greater than 100 amino acids in length.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989, and *Current Protocols in Molecular Biology*, ed. Ausubel et al., Greene Publishing and Wiley-Interscience, New York, 1987 (with periodic updates). PCR primer pairs can be derived from a known sequence, for example, by using computer programs intended for that purpose such as Primer3 (Version 0.4.0, Whitehead Institute for Biomedical Research, Cambridge, Mass.).

Preventing or treating a disease: "Preventing" a disease refers to inhibiting the full development of a disease, for example in a person who is known to be at risk of infection with *M. tuberculosis* or *M. leprae*. An example of a person with a known predisposition is someone living with a person diagnosed with tuberculosis, health care professionals, or someone who has been exposed to *M. tuberculosis*. "Treatment" refers to a therapeutic intervention that ameliorates a sign or symptom of a disease or pathological condition, such as tuberculosis, after it has begun to develop.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. The promoter can be a constitutive or an inducible promoter. A specific, non-limiting example of a promoter is the HCMV IE promoter.

Purified: The term purified does not require absolute purity; rather, it is intended as a relative term. Thus, for example, a purified antigen preparation is one in which the antigen is more pure than the protein in its originating environment within a cell. A preparation of an antigen is typically purified such that the antigen represents at least 50% of the total protein content of the preparation. However, more highly purified preparations may be required for certain applications. For example, for such applications, preparations in which the antigen comprises at least 75% or at least 90% of the total protein content may be employed.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Variants of antigen polypeptides will possess a relatively high degree of sequence identity when aligned using standard methods.

Methods of alignment of sequences for comparison are well known in the art. Altschul et al. (1994) presents a detailed consideration of sequence alignment methods and homology calculations. The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website. A description of how to determine sequence identity using this program is available at the NCBI website, as are the default parameters.

Variants of antigenic polypeptides, such as a *Mycobacterium* polypeptide, are typically characterized by possession of at least 50% sequence identity counted over the full length alignment with the amino acid sequence of a native antigen sequence using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, variants will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website.

Therapeutically active polypeptide: An agent, such as an epitope of Mtb that causes induction of an immune response, as measured by clinical response (for example increase in a population of immune cells, increased cytolytic activity against Mtb, or measurable reduction of a symptom of an infection). Therapeutically active molecules can also be made from nucleic acids. Examples of a nucleic acid based therapeutically active molecule is a nucleic acid sequence that encodes an Mtb epitope, wherein the nucleic acid sequence is operably linked to a control element such as a promoter.

In one embodiment, a therapeutically effective amount of an Mtb polypeptide is an amount used to generate an immune response. In several examples, "treatment" refers to a therapeutic intervention that ameliorates a sign or symptom of tuberculosis.

Therapeutically effective amount: A dose sufficient to inhibit advancement, or to cause regression of the disease, or which is capable of relieving symptoms caused by the disease. In one embodiment, a therapeutically effective dose is a dose sufficient to inhibit or prevent advancement or relieve symptoms of tuberculosis.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Tuberculosis (TB): A disease that is generally caused by *Mycobacterium tuberculosis* that usually infects the lungs. However, other "atypical" mycobacteria such as *M. kansasii* may produce a similar clinical and pathologic appearance of disease.

Transmission of *M. tuberculosis* occurs by the airborne route in confined areas with poor ventilation. In more than 90% of cases, following infection with *M. tuberculosis*, the immune system prevents development of disease from *M. tuberculosis*, often called, active tuberculosis. However, not all of the *M. tuberculosis* is killed, and thus tiny, hard capsules are formed. "Primary tuberculosis" is seen as disease that develops following an initial infection, usually in children. The initial focus of infection is a small subpleural granuloma accompanied by granulomatous hilar lymph node infection. Together, these make up the Ghon complex. In nearly all cases, these granulomas resolve and there is no further spread of the infection. "Secondary tuberculosis" is seen mostly in adults as a reactivation of previous infection (or reinfection), particularly when health status declines. The granulomatous inflammation is much more florid and widespread. Typically, the upper lung lobes are most affected, and cavitation can occur. Dissemination of tuberculosis outside of the lungs can lead to the appearance of a number of uncommon findings with characteristic patterns that include skeletal tuberculosis, genital tract tuberculosis, urinary tract tuberculosis, central nervous system (CNS) tuberculosis, gastrointestinal tuberculosis, adrenal tuberculosis, scrofula, and cardiac tuberculosis. "Latent" tuberculosis is an Mtb infection in an individual that can be detected by a diagnostic assay, such as, but not limited to a tuberculin skin test (TST) wherein the infection does not produce symptoms in that individual. "Active" tuberculosis is a symptomatic Mtb infection in a subject.

Microscopically, the inflammation produced with TB infection is granulomatous, with epithelioid macrophages and Langhans giant cells along with lymphocytes, plasma cells, maybe a few polymorphonuclear cells, fibroblasts with collagen, and characteristic caseous necrosis in the center. The inflammatory response is mediated by a type IV hypersensitivity reaction, and skin testing is based on this reaction. In some examples, tuberculosis can be diagnosed by a skin test, an acid fast stain, an auramine stain, or a combination thereof. The most common specimen screened is sputum, but the histologic stains can also be performed on tissues or other body fluids.

TB is a frequent complication of HIV infection. TB infection in subjects infected with a human immunodeficiency virus (HIV) can spread readily and progress rapidly to active disease. Specific symptoms of lung disease due to Mtb infection include chronic cough and spitting blood. Other symptoms of TB disease include fatigue, loss of appetite, weight loss, fever and drenching night sweats.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli* and *Salmonella*. Vectors also include viral vectors, such as, but not limited to, retrovirus, orthopox, avipox, fowlpox, capripox, suipox, adenovirus, herpes virus, alpha virus, baculovirus, Sindbis virus, vaccinia virus, and poliovirus vectors. Vectors also include vectors for expression in yeast cells Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. *Mycobacterium* Polypeptides

It is disclosed herein that several *Mycobacterium* polypeptides can be used to induce an immune response to Mtb, such as a T cell response. In several embodiments, the polypeptide comprises or consists of the amino acid sequence set forth as:

```
VPHPWDTGDHERNWQGYFIPAMSVLRNRVGARTHAELRDAENDLVEARVI

ELREDPNLLGDRTDLAYLRAIHRQLFQDIYVWAGDLRTVGIEKEDESFCA

PGGISRPMEHVAAEIYQLDRLRAVGEGDLAGQVAYRYDYVNYAHPFREGN

GRSTREFFDLLLSERGSGLDWGKTDLEELHGACHVARANSDLTGLVAMFK

GILDAEPTYDF (SEQ ID NO: 1; see also TUBERCULIST
No. Rv3641c, as available on Jun. 8, 2009,
incorporated herein by reference, known as fic).

MDFALLPPEVNSARMYTGPGAGSLLAAAGGWDSLAAELATTAEAYGSVLS

GLAALHWRGPAAESMAVTAAPYIGWLYTTAEKTQQTAIQARAAALAFEQA

YAMTLPPPVVAANRIQLLALIATNFFGQNTAAIAATEAQYAEMWAQDAAA

MYGYATASAAAALLTPFSPPRQTTNPAGLTAQAAAVSQATDPLSLLIETV

TQALQALTIPSFIPEDFTFLDAIFAGYATVGVTQDVESFVAGTIGAESNL
```

-continued

GLLNVGDENPAEVTPGDFGIGELVSATSPGGGVSASGAGGAASVGNTVLA

SVGRANSIGQLSVPPSWAAPSTRPVSALSPAGLTTLPGTDVAEHGMPGVP

GVPVAAGRASGVLPRYGVRLTVMAHPPAAG (SEQ ID NO: 2; see also TUBERCULIST No. Ry3136, as available on Jun. 8, 2009, incorporated herein by reference, known as PPE51 or PPE).

MTEPRPVFAVVISAGLSAIPMVGGPLQTVFDAIEERTRHRAETTTREICE

SVGGADTVLSRIDKNPELEPLLSQAIEAATRTSMEAKRRLLAQAAAAALE

DDQKVEPASLIVATLSQLEPVHIHALVRLAKAAKSSPDQDEIQRREVMRA

ASKVEPVPVLAALIQTGVAIATTTVWHGNGTGTPAEESGHILIHDVSDFG

HRLLAYLRAADAGAELLILPSGGSAPTGDHPTPHPSTSR (SEQ ID NO: 3; see also TUBERCULIST No. Rv0394c, as available on Jun. 8, 2009, incorporated herein by reference).

MADFLTLSPEVNSARMYAGGGPGSLSAAAAAWDELAAELWLAAASFESV

CSGLADRWWQGPSSRMMAAQAARHTGWLAAAATQAEGAASQAQTMAL

AYEAAFAATVHPALVAANRALVAWLAGSNVFGQNTPAIAAAEAIYEQMW

AQDVVAMLNYHAVASAVGARLRPWQQLLHELPRRLGGEHSDSTNTELAN

PSSTTTRITVPGASPVHAATLLPFIGRLLAARYAELNTAIGTNWFPGTTP

EVVSYPATIGVLSGSLGAVDANQSIAIGQQMLHNEILAATASGQPVTVAG

LSMGSMVIDRELAYLAIDPNAPPSSALTFVELAGPERGLAQTYLPVGTTI

PIAGYTVGNAPESQYNTSVVYSQYDIVVADPPDRPWNLLAGANALMGAAY

FHDLTAYAAPQQGIEIAAVTSSLGGTTTTYMIPSPTLPLLLPLKQIGVPD

WIVGGLNNVLKPLVDAGYSQYAPTAGPYFSHGNLVW (SEQ ID NO: 4; see also TUBERCULIST No. Rv3539, as available on Jun. 8, 2009, incorporated herein by reference, known as PPE63 or PPE).

MTLDVPVNQGHVPPGSVACCLVGVTAVADGIAGHSLSNFGALPPEINSGR

MYSGPGSGPLMAAAAAWDGLAAELSSAATGYGAAISELTNMRWWSGPASD

SMVAAVLPFVGWLSTTATLAEQAAMQARAAAAAFEAAFAMTVPPPAIAA

NRTLLMTLVDTNWFGQNTPAIATTESQYAEMWAQDAAAMYGYASAAAPA

TVLTPFAPPPQTTNATGLVGHATAVAALRGQHSWAAAIPWSDIQKYWMMF

LGALATAEGFIYDSGGLTLNALQFVGGMLWSTALAEAGAAEAAAGAGGA

AGWSAWSQLGAGPVAASATLAAKIGPMSVPPGWSAPPATPQAQTVARSIP

GIRSAAEAAETSVLLRGAPTPGRSRAAHMGRRYGRRLTVMADRPNVG (SEQ ID NO: 5; see also TUBERCULIST No. Rv1706c, as available on Jun. 8, 2009, incorporated herein by reference, known as PPE23 or PPE).

MDFGALPPEINSARMYAGAGAGPMMAAGAAWNGLAAELGTTAASYESVI

TRLTTESWMGPASMAMVAAAQPYLAWLTYTAEAAAHAGSQAMASAAAY

EAAYAMTVPPEVVAANRALLAALVATNVLGINTPAIMATEALYAEMWAQ

DALAMYGYAAASGAAGMLQPLSPPSQTTNPGGLAAQSAAVGSAAATAAV

NQVSVADLISSLPNAVSGLASPVTSVLDSTGLSGIIADIDALLATPFVAN

-continued

IINSAVNTAAWYVNAAIPTAIFLANALNSGAPVAIAEGAIEAAEGAASAA

AAGLADSVTPAGLGASLGEATLVGRLSVPAAWSTAAPATTAGATALEGSG

WTVAAEEAGPVTGMMPGMASAAKGTGAYAGPRYGFKPTVMPKQVVV (SEQ ID NO: 6; see also TUBERCULIST No. Rv1039c, as available on Jun. 8, 2009, incorporated herein by reference, known as PPE15 or PPE).

MAHFSVLPPEINSLRMYLGAGSAPMLQAAAAWDGLAAELGTAASSFSSVT

TGLTGQAWQGPASAAMAAAAAPYAGFLTTASAQAQLAAGQAKAVASVFE

AAKAAIVPPAAVAANREAFLALIRSNWLGLNAPWIAAVESLYEEYWAADV

AAMTGYHAGASQAAAQLPLPAGLQQFLNTLPNLGIGNQGNANLGGGNTGS

GNIGNGNKGSSNLGGGNIGNNNIGSGNRGSDNFGAGNVGTGNIGFGNQGP

IDVNLLATPGQNNVGLGNIGNNNMGFGNTGDANTGGGNTGNGNIGGGNTG

NNNFGFGNTGNNNIGIGLTGNNQMGINLAGLLNSGSGNIGIGNSGTNNIG

LFNSGSGNIGVFNTGANTLVPGDLNNLGVGNSGNANIGFGNAGVLNTGFG

NASILNTGLGNAGELNTGFGNAGFVNTGFDNSGNVNTGNGNSGNINTGSW

NAGNVNTGFGIITDSGLTNSGFGNTGTDVSGFFNTPTGPLAVDVSGFFNT

ASGGTVINGQTSGIGNIGVPGTLFGSVRSGLNTGLFNMGTAISGLFNLRQ

LLG (SEQ ID NO: 7; see also TUBERCULIST No. Rv3558, as available on Jun. 8, 2009, incorporated herein by reference, known as PPE64 or PPE).

MEYLIAAQDVLVAAAADLEGIGSALAAANRAAEAPTTGLLAAGADEVSAA

IASLFSGNAQAYQALSAQAAAFHQQFVRALSSAAGSYAAAEAANASPMQA

VLDVVNGPTQLLLGRPLIGDGANGGPGQNGGDGGLLYGNGGNGGSSSTPG

QPGGRGGAAGLIGNGGAGGAGGPGANGGAGGNGGWLYGNGGLGGNGGA

ATQIGGNGGNGGHGGNAGLWGNGGAGGAGAAGAAGANGQNPVSHQVTH

ATDGADGTTGPDGNGTDAGSGSNAVNPGVGGGAGGIGGDGTNLGQTDVS

GGAGGDGGDGANFASGGAGGNGGAAQSGFGDAVGGNGGAGGNGGAGG

GGGLGGAGGSANVANAGNSIGGNGGAGGNGGIGAPGGAGGAGGNANQD

NPPGGNSTGGNGGAGGDGGVGASADVGGAGGFGGSGGRGGLLLGTGGAG

GDGGVGGDGGIGAQGGSGGNGGNGGIGADGMANQDGDGGDGGNGGDG

GAGGAGGVGGNGGTGGAGGLFGQSGSPGSGAAGGLGGAGGNGGAGGGG

GTGFNPGAPGDPGTQGATGANGQHGLN (SEQ ID NO: 8; see also TUBERCULIST No. Rv1243c, as available on Oct. 6, 2009; incorporated herein by reference, known as PE_PGRS23).

MVMSLMVAPELVAAAAADLTGIGQAISAANAAAAGPTTQVLAAAGDEVS

AAIAALFGTHAQEYQALSARVATFHEQFVRSLTAAGSAYATAEAANASPL

QALEQQVLGAINAPTQLWLGRPLIGDGVHGAPGTGQPGGAGGLLWGNGGN

GGSGAAGQVGGPGGAAGLFGNGGSGGSGGAGAAGGVGGSGGWLNGNGG

AGGAGGTGANGGAGGNAWLFGAGGSGGAGTNGGVGGSGGFVYGNGGA

GGIGGIGGIGGNGGDAGLFGNGGAGGAGAAGLPGAAGLNGGDGSDGGNG

GTGGNGGRGGLLVGNGGAGGAGGVGGDGGKGGAGDPSFAVNNGAGGNG

GHGGNPGVGGAGGAGGLLAGAHGAAGATPTSGGNGGDGGIGATANSPLQ

AGGAGGNGGHGGLVGNGGTGGAGGAGHAGSTGATGTALQPTGGNGTNG

GAGGHGGNGGNGGAQHGDGGVGGKGGAGGSGGAGGNGFDAATLGSPGA

-continued

DGGMGGNGGKGGDGGKAGDGGAGAAGDVTLAVNQGAGGDGGNGGEVG

VGGKGGAGGVSANPALNGSAGANGTAPTSGGNGGNGGAGATPTVAGENG

GAGGNGGHGGSVGNGGAGGAGGNGVAGTGLALNGGNGGNGGIGGNGGS

AAGTGGDGGKGGNGGAGANGQDFSASANGANGGQGGNGGNGGIGGKGG

DAFATFAKAGNGGAGGNGGNVGVAGQGGAGGKGAIPAMKGATGADGTA

PTSGGDGGNGGNGASPTVAGGNGGDGGKGGSGGNVGNGGNGGAGGNGA

AGQAGTPGPTSGDSGTSGTDGGAGGNGGAGGAGGTLAGHGGNGGKGGN

GGQGGIGGAGERGADGAGPNANGANGENGGSGGNGGDGGAGGNGGAGG

KAQAAGYTDGATGTGGDGGNGGDGGKAGDGGAGENGLNSGAMLPGGGT

VGNPGTGGNGGNGGNAGVGGTGGKAGTGSLTGLDGTDGITPNGGNGGNG

GNGGKGGTAGNGSGAAGGNGGNGGSGLNGGDAGNGGNGGGALNQAGFF

GTGGKGGNGGNGGAGMINGGLGGFGGAGGGGAVDVAATTGGAGGNGGA

GGFASTGLGGPGGAGGPGGAGDFASGVGGVGGAGGDGGAGGVGGFGGQ

GGIGGEGRTGGNGGSGGDGGGGISLGGNGGLGGNGGVSETGFGGAGGNG

GYGGPGGPEGNGGLGGNGGAGGNGGVSTTGGDGGAGGKGGNGGDGGNV

GLGGDAGSGGAGGNGGIGTDAGGAGGAGGAGGNGGSSKSTTTGNAGSGG

AGGNGGTGLNGAGGAGGAGGNAGVAGVSFGNAVGGDGGNGGNGGHGG

DGTTGGAGGKGGNGSSGAASGSGVVNVTAGHGGNGGNGGNGGNGSAGA

GGQGGAGGSAGNGGHGGGATGGDGGNGGNGGNSGNSTGVAGLAGGAA

GAGGNGGGTSSAAGHGGSGGSGGSGTTGGAGAAGGNGGAGAGGGSLSTG

QSGGPRRQRWCRWQRRRWLGRQRRRRWCRWQRRCRRQRWRWRCRQRR

LRRQWRQGRRRCRPWLHRRRGRQGRRWRQRRFQQRQRSRWQRR (SEQ ID NO: 9; see also TUBERCULIST No. Rv3345c, as available on Oct. 6, 2009; incorporated herein by reference, known as PE_PGRS50).

VIQTCEVELRWRASQLTLAIATCAGVALAAAVVAGRWQLIAFAAPLLGVL

CSISWQRPVPVIQVHGDPDSQRCFENEHVRVTVWVTTESVDAAVELTVSA

LAGMQFEALESVSRRTTTVSAVAQRWGRYPIRARVAVVARGGLLMGAGTV

DAAEIVVFPLTPPQSTPLPQTELLDRLGAHLTRHVGPGVEYADIRPYVPG

DQLRAVNWVVSARRGRLHVTRRLTDRAADVVVLIDMYRQPAGPATEATER

VVRGAAQVVQTALRNGDRAGIVALGGNRPRWLGADIGQRQFYRVLDTVLG

AGEGFENTTGTLAPRAAVPAGAVVIAFSTLLDTEFALALIDLRKRGHVVV

AVDVLDSCPLQDQLDPLVVRMWALQRSAMYRDMATIGVDVLSWPADHSLQ

QSMGALPNRRRRGRGRASRARLP (SEQ ID NO: 10; see also TUBERCULIST No. Rv3163c, as available on Oct.6, 2009; incorporated herein by reference).

VNRRILTLMVALVPIVVFGVLLAVVTVPFVALGPGPTFDTLGEIDGKQVV

QIVGTQTYPTSGHLNMTTVSQRDGLTLGEALALWLSGQEQLMPRDLVYPP

GKSREEIENDNAADFKRSEAAAEYAALGYLKYPKAVTVASVMDPGPSVDK

LQAGDAIDAVDGTPVGNLDQFTALLKNTKPGQEVTIDFRRKNEPPGIAQI

TLGKNKDRDQGVLGIEVVDAPWAPFAVDFHLANVGGPSAGLMFSLAVVDK

-continued

LTSGHLVGSTFVAGTGTIAVDGKVGQIGGITHKMAAARAAGATVFLVPAK

NCYEASSDSPPGLKLVKVETLSQAVDALHAMTSGSPTPSC (SEQ ID NO: 11; see also TUBERCULIST No. Rv3194c, as available on Oct. 6, 2009; incorporated herein by reference).

MSFVVTAPPVLASAASDLGGIASMISEANAMAAVRTTALAPAAADEVSAA

IAALFSSYARDYQTLSVQVTAFHVQFAQTLTNAGQLYAVVDVGNGVLLKT

EQQVLGVINAPTQTLVGRPLIGDGTHGAPGTGQNGGAGGILWGNGGNGGS

GAPGQPGGRGGDAGLFGHGGHGGVGGPGIAGAAGTAGLPGGNGANGGSGG

IGGAGGAGGNGGLLFGNGGAGGQGGSGGLGGSGGTGGAGMAAGPAGGT

GGIGGIGGIGGAGGVGGHGSALFGHGGINGDGGTGGMGGQGGAGGNGWA

AEGITVGIGEQGGQGGDGGAGGAGGIGGSAGGIGGSQGAGGHGGDGGQG

GAGGSGGVGGGGAGAGGDGGAGGIGGTGGNGSIGGAAGNGGNGGRGGA

GGMATAGSDGGNGGGGGNGGVGVGSAGGAGGTGGDGGAAGAGGAPGH

GYFQQPAPQGLPIGTGGTGGEGGAGGAGGDGGQGDIGFDGGRGGDGGPG

GGGGAGGDGSGTFNAQANNGGDGGAGGVGGAGGTGGTGGVGADGGRG

GDSGRGGDGGNAGHGGAAQFSGRGAYGGEGGSGGAGGNAGGAGTGGTA

GSGGAGGFGGNGADGGNGGNGGNGGFGGINGTFGTNGAGGTGGLGTLLG

GHNGNIGLNGATGGIGSTTLTNATVPLQLVNTTEPVVFISLNGGQMVPVL

LDTGSTGLVMDSQFLTQNFGPVIGTGTAGYAGGLTYNYNTYSTTVDFGNG

LLTLPTSVNVVTSSSPGTLGNFLSRSGAVGVLGIGPNNGFPGTSSIVTAM

PGLLNNGVLIDESAGILQFGPNTLTGGITISGAPISTVAVQIDNGPLQQA

PVMFDSGGINGTIPSALASLPSGGFVPAGTTISVYTSDGQTLLYSYTTTA

TNTPFVTSGGVMNTGHVPFAQQPIYVSYSPTAIGTTTFN (SEQ ID NO: 12; see also TUBERCULIST No. Rv0977, as available on Oct. 6, 2009; incorporated herein by reference).

MTHDHAHSRGVPAMIKEIFAPHSHDAADSVDDTLESTAAGIRTVKISLLV

LGLTALIQIVIVVMSGSVALAADTIHNFADALTAVPLWIAFALGAKPATR

RYTYGFGRVEDLAGSFVVAMITMSAIIAGYEAIARLIHPQQIEHVGWVAL

AGLVGFIGNEWVALYRIRVGHRIGSAALIADGLHARTDGFTSLAVLCSAG

GVALGFPLADPIVGLLITAAILAVLRTAARDVFRRLLDGVDPAMVDAAEQ

ALAARPGVQAVRSVRMRWIGHRLHADAELDVDPALDLAQAHRIAHDAEHE

LTHTVPKLTTALIHAYPAEHGSSIPDRGRTVE (SEQ ID NO: 13; see also TUBERCULIST No. Rv2025c, as available on Oct. 6, 2009; incorporated herein by reference).

VVNFSVLPPEINSGRMFFGAGSGPMLAAAAAWDGLAAELGLAAESFGLVT

SGLAGGSGQAWQGAAAAAMVVAAAPYAGWLAAAAARAGGAAVQAKAV

AGAFEAARAAMVDPVVVAANRSAFVQLVLSNVFGQNAPAIAAAEATYEQ

MWAADVAAMVGYHGGASAAAAALAPWQQAVPGLSGLLGGAANAPAAA

AQGAAQGLAELTLNLGVGNIGSLNLGSGNIGGTNVGSGNVGGTNLGSGNY

GSLNWGSGNTGTGNAGSGNTGDYNPGSGNFGSGNFGSGNIGSLNVGSGNF

GTLNLANGNNGDVNFGGGNTGDFNFGGGNNGTLNFGFGNTGSGNFGFGN

TGNNNIGIGLTGDGQIGIGGLNSGTGNIGFGNSGNNNIGFFNSGDGNIGF

FNSGDGNTGFGNAGNINTGFVVNAGNLNTGFGSAGNGNVGIFDGGNSNSG

-continued

SFNVGFQNTGFGNSGAGNTGFFNAGDSNTGFANAGNVNTGFFNGGDINTG

GFNGGNVNTGFGSALTQAGANSGFGNLGTGNSGWGNSDPSGTGNSGFFNT

GNGNSGFSNAGPAMLPGFNSGFANIGSFNAGIANSGNNLAGISNSGDDSS

GAVNSGSQNSGAFNAGVGLSGFFR(SEQ ID NO: 14; see also TUBERCULIST No. Rv2356c, as available on Oct. 6, 2009; incorporated herein by reference, known as PPE40).

MNYSVLPPEINSLRMFTGAGSAPMLAASVAWDRLAAELAVAASSFGSVTS

GLAGQSWQGAAAAAMAAAAAPYAGWLAAAAARAAGASAQAKAVASAF

EAARAATVHPMLVAANRNAFVQLVLSNLFGQNAPAIAAAEAMYEQMWA

ADVAAMVGYHGGASAAAAQLSSWSIGLQQALPAAPSALAAAIGLGNIGV

GNLGGGNTGDYNLGSGNSGNANVGSGNSGNANVGSGNDGATNLGSGNIGN

TNLGSGNVGNVNLGSGNRGFGNLGNGNFGSGNLGSGNTGSTNFGGGNLGS

FNLGSGNIGSSNIGFGNNGDNNLGLGNNGNNNIGFGLTGDNLVGIGALNS

GIGNLGFGNSGNNNIGFFNSGNNNVGFFNSGNNNFGFGNAGDINTGFGNA

GDTNTGFGNAGFFNMGIGNAGNEDMGVGNGGSFNVGVGNAGNQSVGFGNA

GTLNVGFANAGSINTGFANSGSINTGGFDSGDRNTGFGSSVDQSVSSSGF

GNTGMNSSGFFNTGNVSAGYGNNGDVQSGINNTNSGGFNVGFYNSGAGTV

GIANSGLQTTGIANSGTLNTGVANTGDHSSGGFNQGSDQSGFFGQP (SEQ ID NO: 15; see also TUBERCULIST No. Rv3159c, as available on Oct. 6, 2009; incorporated herein by reference, known as PPE53).

MSFVFAAPEALAAAAADMAGIGSTLNAANVVAAVPTTGVLAAAADEVST

QVAALLSAHAQGYQQLSRQMMTAFHDQFVQALRASADAYATAEASAAQT

MVNAVNAPARALLGHPLISADASTGGGSNALSRVQSMFLGTGGSSALGGS

AAANAAASGALQLQPTGGASGLSAVGALLPRAGAAAAAALPALAAESI

GNAIKNLYNAVEPWVQYGFNLTAWAVGWLPYIGILAPQINFFYYLGEPIV

QAVLFNAIDFVDGTVTFSQALTNIETATAASINQFINTEINWIRGFLPPL

PPISPPGFPSLP (SEQ ID NO: 16; see also TUBERCULIST No. Rv1172c, as available on Oct. 6, 2009; incorporated herein by reference, known as PE12).

MDYAFLPPEINSARMYSGPGPNSMLVAAASWDALAAELASAAENYGSVIA

RLTGMHWWGPASTSMLAMS APYVEWLERTAAQTKQTATQARAAAAAFE

QAHAMTVPPALVTGIRGAIVVETASASNTAGTPP (SEQ ID NO: 17; see also TUBERCULIST No. Rv3135, as available on Jun. 8, 2009, incorporated herein by reference, known as PPE50 or PPE).

LSASVSATTAHHGLPAHEVVLLLESDPYHGLSDGEAAQRLERFGPNTLAV

VTRASLLARILRQFHHPLIYVLLVAGTITAGLKEFVDAAVIFGVVVINAI

VGFIQESKAEAALQGLRSMVHTHAKVVREGHEHTMPSEELVPGDLVLLAA

GDKVPADLRLVRQTGLSVNESALTGESTPVHKDEVALPEGTPVADRRNIA

YSGTLVTAGHGAGIVVATGAETELGEIHRLVGAAEVVATPLTAKLAWFSK

FLTIAILGLAALTFGVGLLRRQDAVETFTAAIALAVGAIPEGLPTAVTIT

LAIGMARMAKRRAVIRRLPAVETLGSTTVICADKTGTLTENQMTVQSIWT

PHGEIRATGTGYAPDVLLCDTDDAPVPVNANAALRWSLLAGACSNDAALV

RDGTRWQIVGDPTEGAMLVVAAKAGFNPERLATTLPQVAAIPFSSERQYM

-continued

ATLHRDGTDHVVLAKGAVERMLDLCGTEMGADGALRPLDRATVLRATEML

TSRGLRVLATGMGAGAGTPDDFDENVIPGSLALTGLQAMSDPPRAAAASA

VAACHSAGIAVKMITGDHAGTATAIATEVGLLDNTEPAAGSVLTGAELAA

LSADQYPEAVDTASVFARVSPEQKLRLVQALQARGHVVAMTGDGVNDAPA

LRQANIGVAMGRGGTEVAKDAADMVLTDDDFATIEAAVEEGRGVFDNLTK

FITWTLPTNLGEGLVILAAIAVGVALPILPTQILWINMTTAIALGLMLAF

EPKEAGIMTRPPRDPDQPLLTGWLVRRTLLVSTLLVASAWWLFAWELDNG

AGLHEARTAALNLFVVVEAFYLFSCRSLTRSAWRLGMFANRWIILGVSAQ

AIAQFAITYLPAMNMVFDTAPIDIGVWVRIFAVATAITIVVATDTLLPRI

RAQPP (SEQ ID NO: 18; see also TUBERCULIST No. Rv1997, as available on June 8, 2009, incorporated herein by reference, known as ctpF).

In a second embodiment, an Mtb polypeptide of use in the methods disclosed herein has a sequence at least 75%, 85%, 90%, 95%, 96%, 97%, 98% or 99% homologous to the amino acid sequence set forth in one of SEQ ID NOs: 1-18. For example, the polypeptide can have an amino acid sequence at least 85%, 90%, 95%, 96%, 97%, 98% or 99% homologous to one of the amino acid sequences set forth in SEQ ID NOs: 1-18. Exemplary sequences can be obtained using computer programs that are readily available on the internet and the amino acid sequences set forth herein. In one example, the polypeptide retains a function of the Mtb protein, such as binding to an antibody that specifically binds the Mtb epitope.

Minor modifications of an Mtb polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein. Thus, a specific, non-limiting example of an Mtb polypeptide is a conservative variant of the Mtb polypeptide (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). A table of conservative substitutions is provided herein. Substitutions of the amino acids sequence shown in SEQ ID NOs: 1-18 can be made based on this table.

Mtb polypeptides are disclosed herein that can be used to induce an immune response to Mtb. These peptides include or consist of at least nine amino acids, such as nine to twenty amino acids consecutive amino acids of an Mtb polypeptide set forth above. In particular non-limiting examples, the Mtb polypeptide includes or consists of MDFALLPPEVNSARM (amino acids 1-15 of SEQ ID NO: 2) or AEMWAQDAA (amino acids 141-149 of SEQ ID NO: 2). Specific, non-limiting examples are fifteen, fourteen, thirteen, twelve, eleven, ten, or nine consecutive amino acids of one of the Mtb polypeptides set forth above. In these examples, the Mtb polypeptide does not include the full-length amino acid sequences set forth as SEQ ID NOs: 1-18.

In several embodiments, the isolated Mtb polypeptide is included in a fusion protein. Thus, the fusion protein can include the Mtb polypeptide (see above) and a second heterologous moiety, such as a myc protein, an enzyme or a carrier (such as a hepatitis carrier protein or bovine serum albumin) covalently linked to the Mtb polypeptide. In several examples, a polypeptide consisting of nine to twelve amino acids of one of the amino acid sequences set forth as SEQ ID NOs: 1-18 that bind MHC class I is covalently linked to a carrier. In an additional example, a polypeptide consisting of one of the amino acid sequences set forth as one of SEQ ID NOs: 1-18 is covalently linked to a carrier.

In additional examples, the polypeptide can be a fusion protein and can also include heterologous sequences to Mtb. Thus, in several specific non-limiting examples, the immunogenic peptide is a fusion polypeptide, for example the polypeptide includes six sequential histidine residues, a β-galactosidase amino acid sequence, or an immunoglobulin amino acid sequence. The polypeptide can also be covalently linked to a carrier. In additional embodiments, the protein consists of the Mtb polypeptide.

The polypeptide can optionally include repetitions of one or more of the Mtb polypeptides disclosed herein. In one specific, non-limiting example, the polypeptide includes two, three, four, five, or up to ten repetitions of one of the Mtb polypeptides described above. Alternatively, more than one polypeptide can be included in a fusion polypeptide. Thus, in several examples, the polypeptide can include at least two, at least three, at least four, at least five or at least six of the amino acid sequences set forth as SEQ ID NOs: 1-18 or nine to twenty amino acids of one of the amino acid sequences set forth as SEQ ID NOs: 1-18 and repetitions of these sequences. A linker sequence can optionally be included between the Mtb polypeptides.

The Mtb polypeptides disclosed herein can be chemically synthesized by standard methods, or can be produced recombinantly. An exemplary process for polypeptide production is described in Lu et al., *FEBS Lett.* 429:31-35, 1998. They can also be isolated by methods including preparative chromatography and immunological separations. Polypeptides can also be produced using molecular genetic techniques, such as by inserting a nucleic acid encoding Mtb or an epitope thereof into an expression vector, introducing the expression vector into a host cell, and isolating the polypeptide (see below).

In particular embodiments provided herein, one or more of the disclosed Mtb polypeptides (or fragments thereof) can be conjugated to a substrate or solid support, such as a plate or array. In one example, the plate or array includes, consists essentially of, or consists of one (such as 2, 3, 4, 5, 6, 7, 8, 9, 10, 11, 12, 13, 14, 15, 16, 17, or all) of SEQ ID NOs: 1-18 or fragments thereof. In some examples, the plate or array also includes one or more control polypeptides. Methods for selecting an appropriate substrate and constructing a plate or array are well known to one of skill in the art (see, e.g., U.S. Pat. Nos. 5,143,854; 5,405,783; 5,445,934; and 5,744,305; all incorporated herein by reference).

Polynucleotides encoding the Mtb polypeptides disclosed herein are also provided. Exemplary nucleic acid sequences are set forth as SEQ ID NOs: 19-36. These polynucleotides include DNA, cDNA and RNA sequences which encode the polypeptide of interest. Silent mutations in the coding sequence result from the degeneracy (i.e., redundancy) of the genetic code, whereby more than one codon can encode the same amino acid residue. Tables showing the standard genetic code can be found in various sources (e.g., L. Stryer, 1988, Biochemistry, 3$^{rd}$ Edition, W.H. Freeman and Co., NY).

A nucleic acid encoding an Mtb polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, N Y, 1989). Polynucleotides also can be isolated by screening genomic or cDNA libraries with probes selected from the sequences of the desired polynucleotide under stringent hybridization conditions.

The polynucleotides encoding an Mtb polypeptide include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (such as AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The Mtb polypeptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast strain lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors encoding the Mtb polypeptides disclosed herein can also be prepared. A number of viral vectors have been constructed, including polyoma, SV40 (Madzak et al., 1992, *J. Gen. Virol.* 73:15331536), adenovirus (Berkner, 1992, *Curr. Top. Microbiol. Immunol.* 158:39-6; Berliner et al., 1988, *BioTechniques* 6:616-629; Gorziglia et al., 1992, *J. Virol.* 66:4407-4412; Quantin et al., 1992, *Proc. Natl. Acad. Sci. USA* 89:2581-2584; Rosenfeld et al., 1992, *Cell* 68:143-155; Wilkinson et al., 1992, *Nucl. Acids Res.* 20:2233-2239; Stratford-Perricaudet et al., 1990, *Hum. Gene Ther.* 1:241-256), vaccinia virus (Mackett et al., 1992, *Biotechnology* 24:495-499), adeno-associated virus (Muzyczka, 1992, *Curr. Top. Microbiol. Immunol.* 158:91-123; On et al., 1990, *Gene* 89:279-282), herpes viruses including HSV and EBV (Margolskee, 1992, *Curr. Top. Microbiol. Immunol.* 158:67-90; Johnson et al., 1992, *J. Virol.* 66:2952-2965; Fink et al., 1992, *Hum. Gene Ther.* 3:11-19; Breakfield et al., 1987, *Mol. Neurobiol.* 1:337-371; Fresse et al., 1990, *Biochem. Pharmacol.* 40:2189-2199), Sindbis viruses (Herweijer et al., 1995, *Hum. Gene Ther.* 6:1161-1167; U.S. Pat. Nos. 5,091,309 and 5,2217,879), alphaviruses (Schlesinger, 1993, *Trends Biotechnol.* 11:18-22; Frolov et al., 1996, *Proc. Natl. Acad. Sci. USA* 93:11371-11377) and retroviruses of avian (Brandyopadhyay et al., 1984, *Mol. Cell Biol.* 4:749-754; Petropouplos et al., 1992, *J. Virol.* 66:3391-3397), murine (Miller, 1992, *Curr. Top. Microbiol. Immunol.* 158:1-24; Miller et al., 1985, *Mol. Cell Biol.* 5:431-437; Sorge et al., 1984, *Mol. Cell Biol.* 4:1730-1737; Mann et al., 1985, *J. Virol.* 54:401-407), and human origin (Page et al., 1990, *J. Virol.* 64:5370-5276; Buchschalcher et al., 1992, *J. Virol.* 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding an Mtb polypeptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses useful in practicing the present methods include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheep pox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and poliovirus.

In some cases, vaccinia viral vectors may elicit a strong antibody response. Thus, while numerous boosts with vaccinia vectors are possible, its repeated use may not be useful in certain instances. However, this sensitivity problem can be minimized by using pox from different genera for boosts. In one example, when the first or initial pox virus vector is vaccinia, the second and subsequent pox virus vectors are selected from the pox viruses from a different genus such as suipox, avipox, capripox or an orthopox immunogenically distinct from vaccinia.

The vaccinia virus genome is known in the art. It is composed of a HIND F13L region, TK region, and an HA region. Recombinant vaccinia virus has been used to incorporate an exogenous gene for expression of the exogenous gene product (see, for example, Perkus et al. *Science* 229:981-984, 1985; Kaufman et al. *Int. J. Cancer* 48:900-907, 1991; *Moss, Science* 252:1662, 1991). A gene encoding an antigen of interest, such as an immunogenic Mtb polypeptide, can be incorporated into the HIND F13L region or alternatively incorporated into the TK region of recombinant vaccinia virus vector (or other nonessential regions of the vaccinia virus genome). Baxby and Paoletti (*Vaccine* 10:8-9, 1992) disclose the construction and use as a vector, of the non-replicating poxvirus, including canarypox virus, fowlpox virus and other avian species. Sutter and Moss (*Proc. Natl. Acad. Sci. U.S.A.* 89:10847-10851, 1992) and Sutter et al. (*Vaccine* 12:1032-1040, 1994) disclose the construction and use as a vector of the non-replicating recombinant Ankara virus (MVA, modified vaccinia Ankara).

Suitable vectors are disclosed, for example, in U.S. Pat. No. 6,998,252, which is incorporated herein by reference. In one example, a recombinant poxvirus, such as a recombinant vaccinia virus is synthetically modified by insertion of a chimeric gene containing vaccinia regulatory sequences or DNA sequences functionally equivalent thereto flanking DNA sequences which in nature are not contiguous with the flanking vaccinia regulatory DNA sequences that encode a Mtb polypeptide. The recombinant virus containing such a chimeric gene is effective at expressing the Mtb polypeptide. In one example, the vaccine viral vector comprises (A) a segment comprised of (i) a first DNA sequence encoding a Mtb polypeptide and (ii) a poxvirus promoter, wherein the poxvirus promoter is adjacent to and exerts transcriptional control over the DNA sequence encoding an Mtb polypeptide; and, flanking said segment, (B) DNA from a nonessential region of a poxvirus genome. The viral vector can encode a selectable marker. In one example, the poxvirus includes, for example, a thymidine kinase gene (see U.S. Pat. No. 6,998,252, which is incorporated herein by reference).

Viral vectors, such as poxviral vectors, that encode an Mtb polypeptide include at least one expression control element operationally linked to the nucleic acid sequence encoding the Mtb polypeptide. The expression control elements are inserted in the viral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the Mtb polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding the one or more Mtb polypeptides are known in the art. Such techniques involve, for example, homologous recombination between the viral DNA sequences flanking the DNA sequence in a donor plasmid and homologous sequences present in the parental virus (Mackett et al., 1982, *Proc. Natl. Acad. Sci. USA* 79:7415-7419). In particular, recombinant viral vectors such as a poxviral vector can be used in delivering the gene. The vector can be constructed for example by steps known in the art, such as steps analogous to the methods for creating synthetic recombinants of the fowlpox virus described in U.S. Pat. No. 5,093,258, incorporated herein by reference. Other techniques include using a unique restriction endonuclease site that is naturally present or artificially inserted in the parental viral vector to insert the heterologous DNA.

Generally, a DNA donor vector contains the following elements: (i) a prokaryotic origin of replication, so that the vector may be amplified in a prokaryotic host; (ii) a gene encoding a marker which allows selection of prokaryotic host cells that contain the vector (e.g., a gene encoding antibiotic resistance); (iii) at least one DNA sequence encoding the one or more Mtb polypeptide located adjacent to a transcriptional promoter capable of directing the expression of the sequence; and (iv) DNA sequences homologous to the region of the parent virus genome where the foreign gene(s) will be inserted, flanking the construct of element (iii). Methods for constructing donor plasmids for the introduction of multiple foreign genes into pox virus are described in PCT Publication No. WO 91/19803, incorporated herein by reference.

Generally, DNA fragments for construction of the donor vector, including fragments containing transcriptional promoters and fragments containing sequences homologous to the region of the parent virus genome into which foreign DNA sequences are to be inserted, can be obtained from genomic DNA or cloned DNA fragments. The donor plasmids can be mono-, di-, or multivalent (e.g., can contain one or more inserted foreign DNA sequences). The donor vector can contain an additional gene that encodes a marker that will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., 1988, *J. Virol.* 62:1046; Falkner and Moss, 1988, *J. Virol.* 62:1849; Franke et al., 1985, *Mol. Cell. Biol.* 5:1918), as well as genes such as the *E. coli* lacZ gene, that permit identification of recombinant viral plaques by colorimetric assay (Panicali et al., 1986, *Gene* 47:193-199).

The DNA gene sequence to be inserted into the virus can be placed into a donor plasmid, such as an *E. coli* or a *Salmonella* plasmid construct, into which DNA homologous to a section of DNA such as that of the insertion site of the poxvirus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA that is the desired insertion region. With a parental pox viral vector, a pox promoter is used. The resulting plasmid construct is then amplified by growth within *E. coli* bacteria and isolated. Next, the isolated plasmid containing the DNA gene sequence to be inserted is transfected into a cell culture, for example chick embryo fibroblasts, along with the parental virus, for example poxvirus. Recombination between homologous pox DNA in the plasmid and the viral genome respectively results in a recombinant poxvirus modified by the presence of the promoter-gene construct in its genome, at a site that does not affect virus viability.

As noted above, the DNA sequence is inserted into a region (insertion region) in the virus that does not affect virus viability of the resultant recombinant virus. One of skill in the art can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. The TK gene has been found in all pox virus genomes examined, including leporipoxvirus (Upton et al., 1986, *J. Virol.* 60:920); shope fibroma virus; capripoxvirus (Gershon et al., 1989, *J. Gen. Virol.* 70:525); Kenya sheep-1; orthopoxvirus (Weir et al., 1983, *J. Virol.* 46:530); vaccinia (Esposito et al., 1984, *Virology* 135:561); monkeypox and variola virus (Hruby et al., 1983, *Proc. Natl. Acad. Sci. USA* 80:3411); vaccinia (Kilpatrick et al., 1985, *Virology* 143:399); Yaba monkey tumor virus; avipoxvirus (Binns et al., 1988, *J. Gen. Virol.* 69:1275); fowlpox; (Boyle et al., 1987, *Virology* 156:355; Schnitzlein et al., 1988, *J. Virol. Meth.* 20:341); and entomopox (Lytvyn et al., 1992, *J. Gen. Virol.* 73:3235-3240). In vaccinia, in addition to the TK region, other insertion regions include, for example, the HindIII M fragment. In fowlpox, in addition to the TK region, other insertion regions include, for example, the BamHI J fragment (Jenkins et al., 1991, *AIDS Res. Hum. Retroviruses* 7:991-998), the EcoRI-HindIII fragment, EcoRV-HindIII fragment, BamHI fragment and the HindIII fragment set forth in EPO Application No. 0 308220 A1 (see also Calvert et al., 1993, *J. Virol.* 67:3069-3076; Taylor et al., 1988, *Vaccine* 6:497-503; Spehner et al., 1990, *J. Virol.* 64:527-533; Boursnell et al., 1990, *J. Gen. Virol.* 71:621-628).

In swinepox, insertion sites include the thymidine kinase gene region. In addition to the requirement that the gene be inserted into an insertion region, successful expression of the inserted gene by the modified poxvirus requires the presence of a promoter operably linked to the desired gene. Generally, the promoter is placed so that it is located upstream from the gene to be expressed. Promoters are well known in the art and can readily be selected depending on the host and the cell type to be targeted. In one example, in poxviruses, pox viral promoters are used, such as the vaccinia 7.5K, 40K or fowlpox promoters such as FPV CIA. Enhancer elements can also be used in combination to increase the level of expression. Furthermore, inducible promoters can be utilized.

Homologous recombination between donor plasmid DNA and viral DNA in an infected cell can result in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (see U.S. Pat. No. 4,603,112 and PCT Publication No. WO 89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be $TK^-$ and can be selected on this basis (Mackett et al., 1982, *Proc. Natl. Acad. Sci. USA* 79:7415). Alternatively, co-integration of a gene encoding a marker or indicator gene with the foreign gene(s) of interest, as described above, can be used to identify recombinant progeny. One specific non-limiting example of an indicator gene is the *E. coli* lacZ gene. Recombinant viruses expressing beta-galactosidase can be selected using a chromogenic substrate for the enzyme (Panicali et al., 1986, *Gene* 47:193). Once a recombinant virus has been identified, a variety of well-known methods can be used to assay the expression of the Mtb sequence encoded by the inserted DNA fragment. These methods include black plaque assay (an in situ enzyme immunoassay performed on viral plaques), Western blot analysis, radioimmunoprecipitation (RIPA), and enzyme immunoassay (EIA).

This disclosure encompasses a recombinant virus comprising more than one antigen of interest for the purpose of having a multivalent vaccine. For example, the recombinant virus may comprise the virus genome or portions thereof, the nucleic acid sequence encoding the Mtb polypeptide and a nucleic acid sequence encoding a hepatitis B surface antigen or any other carrier protein.

In one embodiment, a composition is provided that includes a recombinant virus comprising a vaccinia virus genome or portions thereof, the nucleic acid sequence encoding an Mtb polypeptide and a recombinant virus comprising the nucleic acid sequence encoding the immunostimulatory molecule, B7-1 alone or in combination with the nucleic acid sequence encoding the immunostimulatory molecule, B7-2, or a recombinant virus containing both the genes for an Mtb polypeptide and an immunostimulatory molecule. This disclosure also encompasses a recombinant virus comprising the Mtb polypeptide that is administered with a second recombinant virus comprising the virus genome or portion thereof, and one or more nucleic acid sequences encoding one or more B7 molecules, such as a recombinant vaccinia virus expressing B7-1 and/or B7-2.

Thus, in one example, recombinant virus is disclosed that is a recombinant vaccinia virus containing B7-1 and a recombinant vaccinia virus containing B7-2 (designated rV-B7-1 and rV-B7-2, respectively); the composition can include rV-B7-1 and/or rV-B7-2 in combination with an immunogenic Mtb polypeptide.

The B7 molecule includes but is not limited to B7-1, B7-2 and analogs thereof. The B7 gene may be cloned from mammalian sources, including but not limited to mammalian tissues, genomic libraries or cDNA libraries, such as from murine or human sources. Without being bound by theory, costimulatory molecules of the B7 family (namely B7-1, B7-2, and possibly B7-3) are believed to be members of the immunoglobulin gene superfamily. These molecules are present on macrophages, dendritic cells, monocytes (antigen presenting cells (APCs)). Significant amplification of the immune response against a given antigen generally does not occur without co-stimulation (June et al., *Immunology Today* 15:321-331, 1994; Chen et al., *Immunology Today* 14:483-486; Townsend et al., *Science* 259:368-370). Freeman et al. (*J. Immunol.* 143:2714-2722, 1989) report cloning and sequencing of a B7-1 gene. Azuma et al. (*Nature* 366:76-79, 1993) report cloning and sequencing of a B7-2 gene. Thus, in one embodiment the B7-1 gene or the B7-2 genes are administered in conjunction with the Mtb polypeptide. The insertion of nucleic acids encoding B7-1 and B7-2 into vaccinia virus has been disclosed (see for example, U.S. Pat. No. 6,893,869, incorporated herein by reference; this U.S. Patent also discloses the use of a nucleic acid encoding IL-2 in a vaccinia virus). Several vectors including IL-2, B7-1 and B7-2 have been deposited with the American Type Culture Collection (ATCC) on Oct. 3, 1994 under the terms of the Budapest Treaty (for example, rV-CEA/$_n$IL-2 (ATCC Designation VR 2480), rV-$_m$B7-2 (ATCC Designation VR 2482); and rV-$_m$B7-1 (ATCC Designation VR 2483)).

DNA sequences encoding an Mtb polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding an Mtb polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Host cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), *mycobacterium* (such as *M. smegmatis*), plant, and animal cells (for example, mammalian cells, such as human) Exemplary cells of use include *E. coli, Bacillus subtilis, Saccharomyces cerevisiae, Salmonella typhimurium*, SF9 cells, $C_{129}$ cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. *Meth. Enzymol.*, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although other cell lines may be used, such as cells designed to provide higher expression, desirable glycosylation patterns, or other features. As discussed above, techniques for the transformation of yeast cells, such as polyethylene glycol transformation, protoplast transformation and gene guns are also known in the art (see Gietz and Woods, *Meth. Enzymol.* 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an Mtb polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

In particular embodiments provided herein, one or more of the disclosed Mtb polynucleotides (or fragments thereof) can be conjugated to a substrate or solid support, such as a plate or array. In one example, the plate or array includes, consists essentially of, or consists of one (such as 2, 3, 4, 5, 6, 7, 8, 9, 10, 11, 12, 13, 14, 15, 16, 17, or all) of SEQ ID NOs: 19-36 or fragments thereof. In some examples, the plate or array also includes one or more control polynucleotides. Methods for selecting an appropriate substrate and constructing a plate or array are well known to one of skill in the art (see, e.g., U.S. Pat. Nos. 5,554,501; 5,985,567; 5,981,185; and 6,013,789; and PCT Publications WO 85/01051 and WO 89/10977; all incorporated herein by reference).

IV. Therapeutic Methods and Pharmaceutical Compositions

The Mtb polypeptides disclosed herein, or nucleic acids encoding the Mtb polypeptides, can be used to generate an immune response in a subject. In several examples, the subject is infected with Mtb or is at risk of being infected with Mtb. Thus, in several embodiments, the methods include administering to a subject a therapeutically effective amount of one or more of the Mtb polypeptides disclosed herein (or polynucleotides encoding these polypeptides) in order to generate an immune response, such as, but not limited to, a protective immune response.

In exemplary applications, compositions are administered to a subject in an amount sufficient to produce an immune response to Mtb. These Mtb polypeptides, or polynucleotides encoding these polypeptides, are of use to inhibit or prevent an infection with Mtb, inhibit or prevent progression to disease in a subject having a latent Mtb infection, or to treat tuberculosis in a subject infected with Mtb. In several examples, administration of a therapeutically effective amount of a composition including one or more of the Mtb polypeptides disclosed herein (or polynucleotides encoding these polypeptides) induces a sufficient immune response to decrease a symptom of a disease due to Mtb infection, to inhibit the development of one or more symptoms of tuberculosis, or to inhibit infection with Mtb.

In some examples, the compositions are of use in inhibiting or preventing a future infection with Mtb. Thus, a therapeutically effective amount of the composition is administered to a subject at risk of becoming infected with Mtb. The composition inhibits or prevents the development of tuberculosis, such as latent or active tuberculosis, in the subject upon subsequent exposure to Mtb.

In additional examples, the compositions are administered to a subject with a latent Mtb infection, and inhibit or prevent the development of symptoms of tuberculosis. In some examples, the compositions are of use in treating a subject with latent tuberculosis, such that the subject does not develop active tuberculosis.

Amounts effective for these uses will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer. In other examples, a therapeutically effective amount is an amount sufficient to inhibit an infection with Mtb in a subject upon subsequent exposure of the subject to Mtb. In additional examples, a therapeutically effective amount is an amount sufficient to inhibit development of one or more symptoms in a subject infected with Mtb.

In some examples, one or more Mtb polypeptide described herein may be covalently linked to at least one other immunogenic protein, wherein the conjugate elicits an immune response to the Mtb polypeptide in a subject. The other immunogenic protein (sometimes referred to as a "carrier" protein) ideally has the properties of being immunogenic by itself, usable in a subject, and of a size that can be easily purified and conjugated to at least one other protein or peptide. Suitable carrier proteins are known to one of skill in the art. In particular examples, the other immunogenic protein (carrier protein) is bovine serum albumin (BSA), ovalbumin, tetanus toxoid, diphtheria toxoid, cholera toxin, *Clostridium difficile* toxin A, *C. difficile* toxin B, Shiga toxin, or *Pseudomonas aeruginosa* recombinant exoprotein A.

An Mtb polypeptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular injection, subcutaneous injection, intraperitoneal injection, intravenous injection, oral administration, nasal administration, transdermal administration, or even anal administration. In one embodiment, administration is by oral administration, subcutaneous injection, or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

In one specific, non-limiting example, the Mtb polypeptide is administered in a manner to direct the immune response to a cellular response (that is, a cytotoxic T lymphocyte (CTL) response), rather than a humoral (antibody) response.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 4-1 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1 B7-2, OX-40L, 4-1 BBL, and/or ICAM-1 are administered.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

A pharmaceutical composition including an Mtb polypeptide is thus provided. These compositions are of use to promote an immune response to Mtb. In one embodiment, the Mtb polypeptide is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977; and Hunter et al., *J. Immunol.* 127:1244-1250, 1981; for example, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. *The agent can be provided in an effective amount, for example between* 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif, or a biological adjuvant (see above).

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *InL J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342; and 5,534,496).

In another embodiment, a pharmaceutical composition includes a nucleic acid encoding an Mtb polypeptide. A therapeutically effective amount of the Mtb polynucleotide can be administered to a subject in order to generate an immune response.

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 4-1 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically to the host. It should be noted that these molecules can be co-administered via insertion of a nucleic acid encoding the molecules into a vector, for example, a recombinant pox vector (see, for example, U.S. Pat. No. 6,045,802). In various embodiments, the nucleic acid encoding the biological adjuvant can be cloned into same vector as the Mtb polypeptide coding sequence, or the nucleic acid can be cloned into one or more separate vectors for co-administration. In addition, nonspecific immunomodulating factors such as BCG and levamisole can be co-administered.

One approach to administration of nucleic acids is direct immunization with plasmid DNA, such as with a mammalian expression plasmid. As described above, the nucleotide sequence encoding an Mtb polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™ (negatively charged cage-like structures of 30-40 nm in size formed spontaneously on mixing cholesterol and saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In another approach to using nucleic acids for immunization, an Mtb polypeptide can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG provides another vector for expression of the peptides (see Stover, *Nature* 351:456-460, 1991).

When a viral vector is utilized, it is desirable to provide the recipient with a dosage of each recombinant virus in the composition in the range of from about $10^5$ to about $10^{10}$ plaque forming units, although a lower or higher dose can be administered. The composition of recombinant viral vectors can be introduced into a mammal (1) prior to any evidence of an infection with Mtb; (2) to inhibit development of tuberculosis in an individual infected with Mtb; or (3) to decrease a symptom of tuberculosis in a mammal infected with Mtb. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally in a pharmaceutically acceptable carrier. Generally, the quantity of recombinant viral vector, carrying the nucleic acid sequence of one or more Mtb polypeptides to be administered is based on the titer of virus particles. An exemplary range of the immunogen to be administered is $10^5$ to $10^{10}$ virus particles per mammal, such as a human.

In the embodiment where a combination of a first recombinant viral vector carrying a nucleic acid sequence of one or more Mtb polypeptide and a second recombinant viral vector carrying the nucleic acid sequence of one or more immunostimulatory molecules is used, the mammal can be immunized with different ratios of the first and second recombinant viral vector. In one embodiment the ratio of the first vector to the second vector is about 1:1, or about 1:3, or about 1:5. Optimal ratios of the first vector to the second vector may easily be titered using the methods known in the art (see, for example, U.S. Pat. No. 6,893,869, incorporated herein by reference).

In one embodiment the recombinant viruses have been constructed to express cytokines (such as TNF-α, IL-6, GM-CSF, and IL-2), and costimulatory and accessory molecules (B7-1, B7-2) alone and in a variety of combinations. Simultaneous production of an immunostimulatory molecule and the Mtb polypeptide enhances the generation of specific effectors. Without being bound by theory, dependent upon the specific immunostimulatory molecules, different mechanisms might be responsible for the enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. For example, IL-2, IL-6, interferon, tumor necrosis factor, or a nucleic acid encoding these molecules, can be administered in conjunction with an Mtb immunogenic polypeptide, or a nucleic acid encoding an Mtb polypeptide. The co-expression of an Mtb polypeptide together with at least one immunostimulatory molecule can be effective in an animal model to show therapeutic effects.

In one embodiment, a nucleic acid encoding an Mtb polypeptide is introduced directly into cells. For example, the nucleic acid can be loaded onto gold microspheres by standard methods and introduced into the skin by a device such as the Helios™ Gene Gun (Bio-Rad, Hercules, Calif.). The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, for example, U.S. Pat. No. 5,589,466).

In one specific, non-limiting example, a pharmaceutical composition for intravenous administration would include about 0.1 μg to 10 mg of immunogenic Mtb polypeptide per patient per day. Dosages from 0.1 to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Sciences,* $19^{th}$ Ed., Mack Publishing Company, Easton, Pa., 1995.

Single or multiple administrations of the compositions are administered, depending on the dosage and frequency as required and tolerated by the subject. In one embodiment, the dosage is administered once as a bolus, but in another embodiment can be applied periodically until a therapeutic result is achieved. In one embodiment, the dose is sufficient to treat or ameliorate symptoms or signs of tuberculosis without producing unacceptable toxicity to the subject. In another embodiment, the dose is sufficient to inhibit infection with Mtb upon subsequent exposure to Mtb. In a further embodiment, the dose is sufficient to inhibit a symptom of tuberculosis in a subject with a latent Mtb infection. Systemic or local administration can be utilized.

In another method, antigen presenting cells (APCs), such as dendritic cells (DCs), are isolated from a subject of interest and pulsed or co-incubated with peptides comprising an Mtb polypeptide in vitro. In one specific, non-limiting example, the APCs are autologous cells isolated from the subject of interest. A therapeutically effective amount of the antigen presenting cells is administered (re-introduced) to the subject of interest.

The Mtb polypeptide can be delivered to the DCs or to DC precursors via any method known in the art, including, but not limited to, pulsing DCs directly with antigen, or utilizing a broad variety of antigen delivery vehicles, such as, for example, liposomes, or other vectors known to deliver antigen to cells. In one specific, non-limiting example an antigenic formulation includes about 0.1 μg to about 1,000 μg, or about 1 to about 100 μg of a selected Mtb polypeptide. The Mtb polypeptide can also be administered with agents that promote DC maturation. Specific, non-limiting examples of agents of use are interleukin-4 (IL-4) and granulocyte/macrophage colony stimulating factor (GM-CSF), or flt-3 ligand (flt-3L). The preparation can also contain buffers, excipients, and preservatives, amongst other ingredients.

In one embodiment, mature APCs are generated to present the immunogenic Mtb polypeptide. These DCs are then administered alone to a subject infected with Mtb, or at risk for infection with Mtb. In another embodiment, the mature DCs are administered in conjunction with an antibacterial or antiviral agent.

Alternatively, the APCs are used to sensitize CD8 cells, such as peripheral blood lymphocytes (PBLs). The PBLs can be from the same subject (autologous) that is to be treated. Alternatively, the PBLs can be heterologous. However, they should at least be MHC Class-I restricted to the HLA types the subject possesses. An effective amount of the sensitized cells is then administered to the subject.

Peripheral blood mononuclear cells (PBMCs) can be used as the responder cell source of cytotoxic T lymphocyte (CTL) precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

Alternatively, a $CD8^+$ T cell clone that recognizes the Mtb polypeptide can be isolated from a subject of interest. This $CD8^+$ T cell clone can be expanded in vitro, using methods known in the art. A therapeutically effective amount of the $CD8^+$ T cells is then administered to the subject of interest.

Thus, cells can be administered to a subject to treat, inhibit, or even prevent an Mtb infection, such as to decrease a symptom of an Mtb infection. In these applications, a therapeutically effective amount of activated APCs, or activated lymphocytes, are administered to a subject in an amount sufficient to raise an immune response to Mtb.

In supplemental methods, any therapeutic regimen is augmented by administering a cytokine, such as interleukin (IL)-2, IL-3, IL-6, IL-10, IL-12, IL-15, GM-CSF, interferons. In further methods, an additional antibacterial or antiviral agent is administered to the subject.

The disclosure is illustrated by the following non-limiting Examples.

EXAMPLES

Example 1

Selection of Antigens

A peptide library encompassing 39,499 Mtb peptides was screened for antigens and/or epitopes that were both strongly and commonly recognized in individuals with Mtb infection in Portland, Oreg. This peptide library represents 389 genes, representing roughly 10% of the Mtb genome. The peptides are 15 mers overlapping by 11 amino acids for each gene product. 50 nmol of each peptide was synthesized individually and then pooled into 777 pools of 50 peptides in a 96 well format (nine plates). Five blank wells and one well of an irrelevant peptide pool, SIV gag, were included on each of the nine plates.

$CD8^+$ T cells from donors were screened against the peptide library by IFN-γ ELISPOT. The IFN-γ ELISPOT assay was performed as described previously (Beckman et al., *J. Immunol.* 157:2795-2803, 1996). For determination of ex vivo frequencies of $CD8^+$ T cells responding to Mtb infection or Mtb antigens, $CD8^+$ T-cells were positively selected from peripheral blood mononuclear cells using magnetic beads (Miltenyi Biotec, Auburn Calif.) as a source of responder T cells and tested for their response to autologous DC. Each plate of the genomic peptide library was screened in duplicate, for a total of 18 ELISPOT plates per screen. CD8+ T cells were prepared from cryopreserved PBMC by CD8 selection using magnetic bead separations. Resulting cell populations contained >99% CD8+ T cells. CD8+ T cells (250,000 cells/well), autologous DCs (20,000 cells/well), and IL-2 (0.5 ng/ml) were added to peptide (final 5 ug/ml, individual peptides) in the ELISPOT plates. Five media control wells were included on each plate. Spots are enumerated using with the AID EliSpot Reader System. For each plate, the mean of these five wells was subtracted from each well of that plate to normalize between plates. Each technical replicate on each plate was then scored. A well was scored positive if the spot forming units (SFU), less the mean of the media wells, was greater than or equal to ten and the SFU was greater than or equal to twice the mean of the media. Twenty donors were tested, including fifteen LTBI (6 Caucasian, 4 African American, 5 SE Asian) and five donors with active TB.

Two criteria were used to select the peptide pools. First, peptide pools had to be in the top 5% of a donor's response. Second, the peptide pool had to be recognized by three or more donors. The peptide pools selected by this method were identical independent of the order these criteria were applied. A well was considered positive in the donor screen if only one technical replicate was statistically positive. However, since there is more confidence in a well where both technical replicates are positive, the selected wells were compared if the average spot forming units (SFU) for wells with two positive technical replicates was weighted by 200% to the selected wells if the average SFU was not weighted. 32 wells were selected if there was no weighting given to the technical replicates and 35 wells were selected if the weighting was applied. However, 19 wells were selected by both weighting and not weighting the average SFU and these were chosen for further analysis (Table 2).

TABLE 2

| Selected antigens and epitopes for clinical validation studies | | |
|---|---|---|
| Antigen Number | Rv Numbers | Gene Names |
| 1 | Rv3641c (33)[1] | fic |
| 2 | Rv3136 (46): Rv3135 (4) | PPE51: PPE50 |
| 3 | Rv0383c (30): Rv0394c (20) | Rv0383c: Rv0394c |
| 4 | Rv1184c (20) | Rv1184c |
| 5 | Rv3514 (47): Rv3532 (3) | PE_PGRS57: PPE61 |
| 6 | Rv3558 (44): Rv3539 (6) | PPE64: PPE63 |
| 7 | Rv1979c (50) | Rv1979c |
| 8 | Rv1980c (28): Rv1984c (22) | mpt64: cfp21 |
| 9 | Rv3347c (50) | PPE55 |
| 10 | Rv0151c (50) | PE1 |
| 11 | Rv1997 (50) | ctpF |
| 12 | Rv1997 (50) | ctpF |
| 13 | Rv0159c (50) | PE3 |
| 14 | Rv1997 (50) | ctpF |
| 15 | Rv2711 (37): Rv1404 (13) | ideR: Rv1404 |
| 16 | Rv1706c (50) | PPE23 |
| 17 | Rv2041c (50) | Rv2041c |
| 18 | Rv2041c (43): Rv2093c (7) | Rv2041c: tatC |
| 19 | Rv1039c (50) | PPE15 |

[1]Number of peptides from each gene shown in parentheses

Example 2

Screening of Selected Antigens

The antigens identified in Example 1 were screened in a CD8 ELISPOT assay against latent and active TB donors from Uganda. ELISPOT plates were read using the AID ELISPOT reader and output was exported into excel files. Data were imported into SAS® version 9.1 (SAS Institute, Inc., Cary, N.C.) and analyzed. A categorical variable for a positive ELISPOT was created in SAS®. For a positive response to the antigen, the mean of the antigen containing wells must be greater than the background wells by two standard deviations. If this was true, the background was subtracted and this difference must then be greater than 10 spots. Similarly, a continuous ELISPOT variable was created for each antigen detailing the spot forming units remaining if the antigen met the categorical criteria above. The results were graphed by proportion of positive responses stratified by active or latent TB along with the corresponding spot forming unit (FIGS. 1A and B).

Five antigens were selected for the validation stage. Several factors were considered in the selection, including those antigens that had a suggestion of disease specificity, as well as antigens with a broad and strong response. These antigens included PPE50:51, PE3, CtpF, PPE15, and EsxJ. Fifty-six latent and 52 active TB individuals were studied in the validation phase. Twenty-one individuals (19.2%) responded to all five antigens at the predefined cut-off, whereas 10 individuals (9%) responded to four of the antigens. Forty individuals (36%) responded to up to three antigens and 35% did not respond to any of the five antigens selected. Although some disease specificity was noted in the screening stage, especially as it applied to PPE50:51, this was not apparent in the validation stage.

Figure 2A:
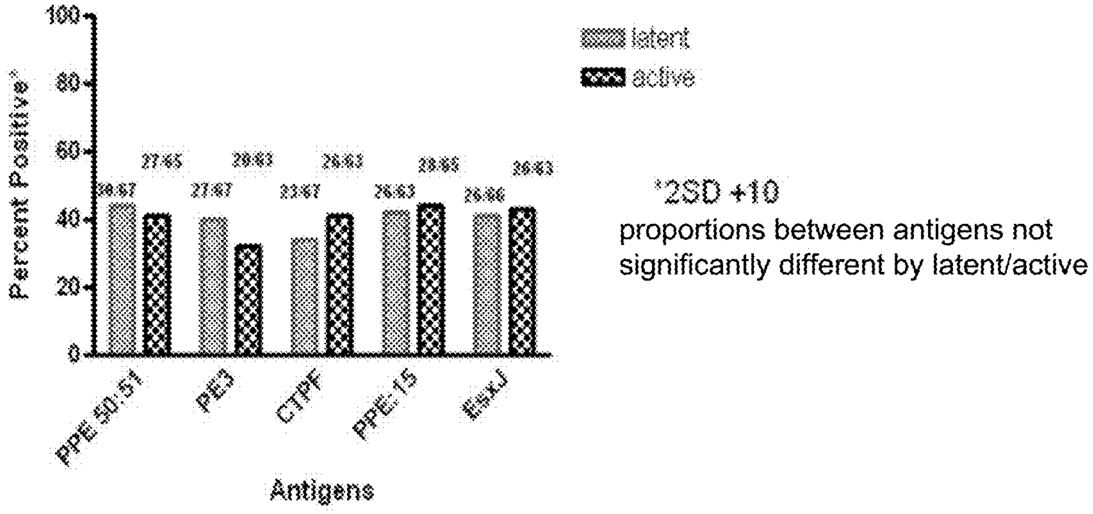
FIG. 2A is a bar graph showing percent positive samples for five selected antigens by CD8 ELISPOT assay in individuals with latent or active TB.
Figure 2B:
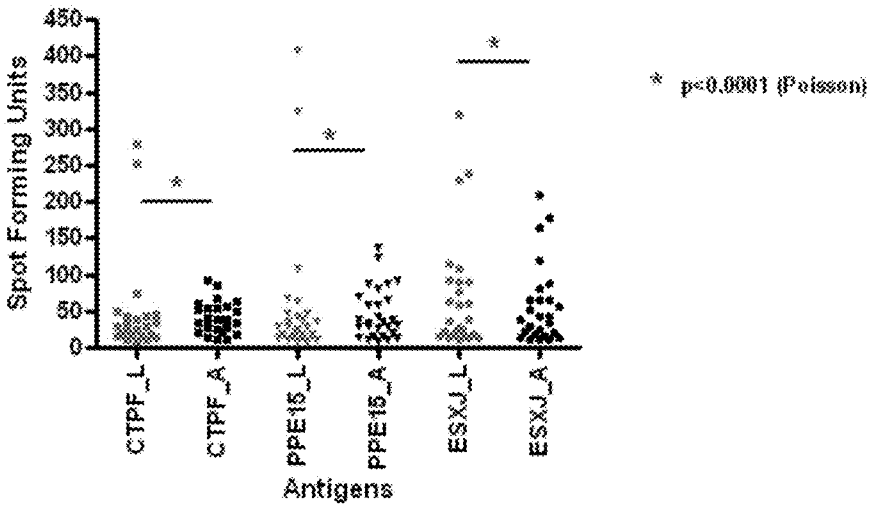
FIG. 2B is a graph showing SFU/250,000 CD4/CD56 depleted PBMC by ELISPOT assay. For each antigen, "L" indicates individuals with latent TB infection and "A" indicates individuals with active TB infection.

The magnitude of the response was studied as well. Using Poisson modeling, individuals with latent disease had a significantly greater spot count than those with active disease for 4 antigens (PPE50:51, cTPF, PPE15, EsXJ) however the difference was not clinically meaningful (FIG. 2).

Example 3

Additional Antigens

Additional antigens were selected using the methods described in Example 1. The additional antigens are provided in Table 3.

Figure 3:
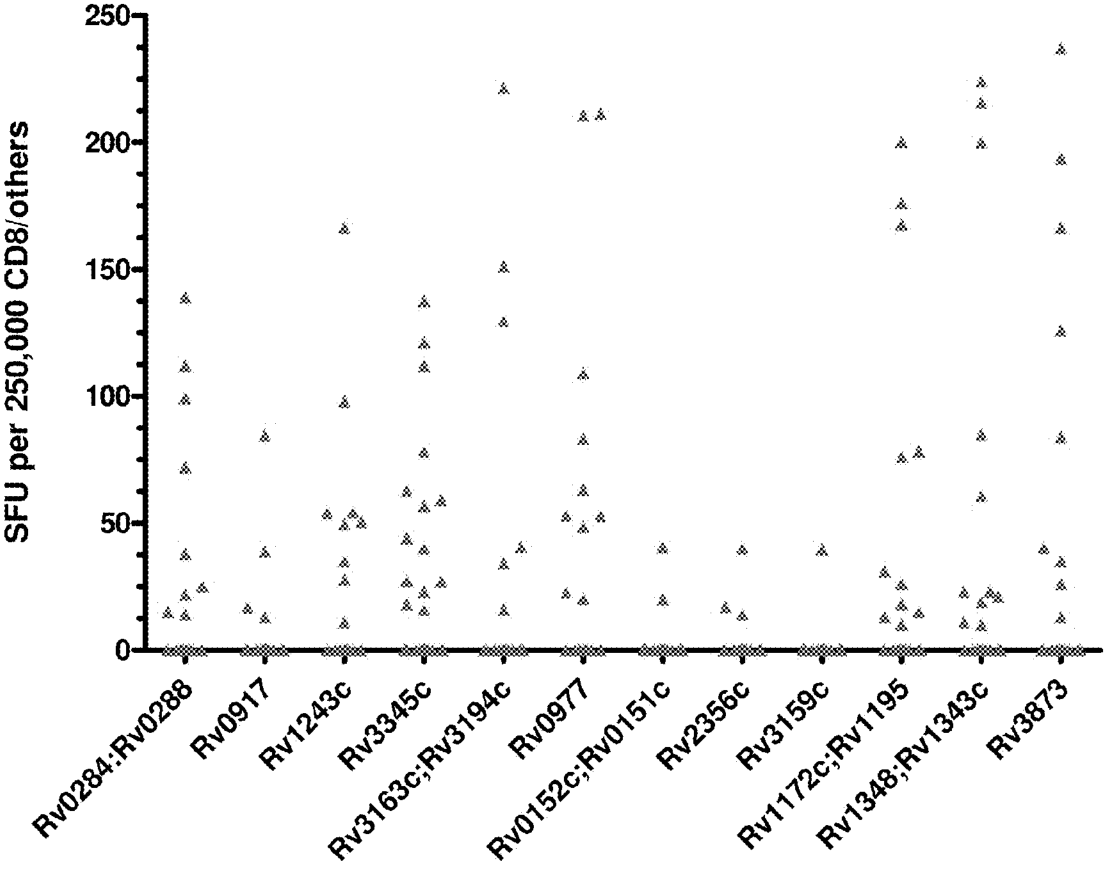
FIG. 3 is a graph showing SFU for each antigen in the ELISPOT assay.

The additional identified antigens were screened in a CD8 ELISPOT assay (as described in Examples 1 and 2) against latent and active TB donors from Uganda. The results were graphed by the corresponding spot forming unit (FIG. 3).

TABLE 3

| Additional antigens and epitopes for clinical validation studies | |
|---|---|
| Rv_Numbers (# peptides in pool) | Gene_Names |
| Rv0284(17): Rv0288(11) | Rv0284: esxH |
| Rv0917(31) | betP |
| Rv1243c(50) | PE_PGRS23 |
| Rv3345c(100) | PE_PGRS50 |
| Rv3163c(41): Rv3194c(9) | Rv3163c: Rv3194c |
| Rv0977(50) | PE_PGRS16 |
| Rv0152c(40): Rv0151c(10) | PE2: PE1 |
| Rv1917c(50) | PPE34 |
| Rv2040c(37): Rv2025c(13) | Rv2040c: Rv2025c |
| Rv2356c(50) | PPE40 |
| Rv3159c(50) | PPE53 |
| Rv1172c(32): Rv1195(18) | PE12: PE13 |
| Rv1348(35): Rv1343c(15) | Rv1348: 1prD |
| Rv3873(50) | PPE68 |

Example 4

Identification of Peptide-Specific T Cell Clones

Peptide-specific T cell clones were isolated from individuals with LTBI or active TB, using peptide pulsed DCs as APCs and limiting dilution cloning methodology. Briefly, CD8+ T cells were isolated from PBMCs using positive selection using CD8 antibody-coated magnetic beads per the manufacturer's instructions (Miltenyi Biotec, Bergisch Gladbach, Germany). T cells were seeded at various concentrations in the presence of a $2\times10^4$—irradiated autologous peptide pulsed DC, $1\times10^5$ irradiated autologous PBMC, and rIL-2 (5 ng/ml) in cell culture media consisting of 200 μl of RPMI 1640 supplemented with 10% human sera. Wells exhibiting growth between 10-14 days were assessed for peptide specificity using ELISPOT and peptide pulsed DCs as a source of APCs. T cells retaining peptide specificity were further phenotyped for αβ T cell receptor expression and CD8 expression by FACS.

Figure 4:
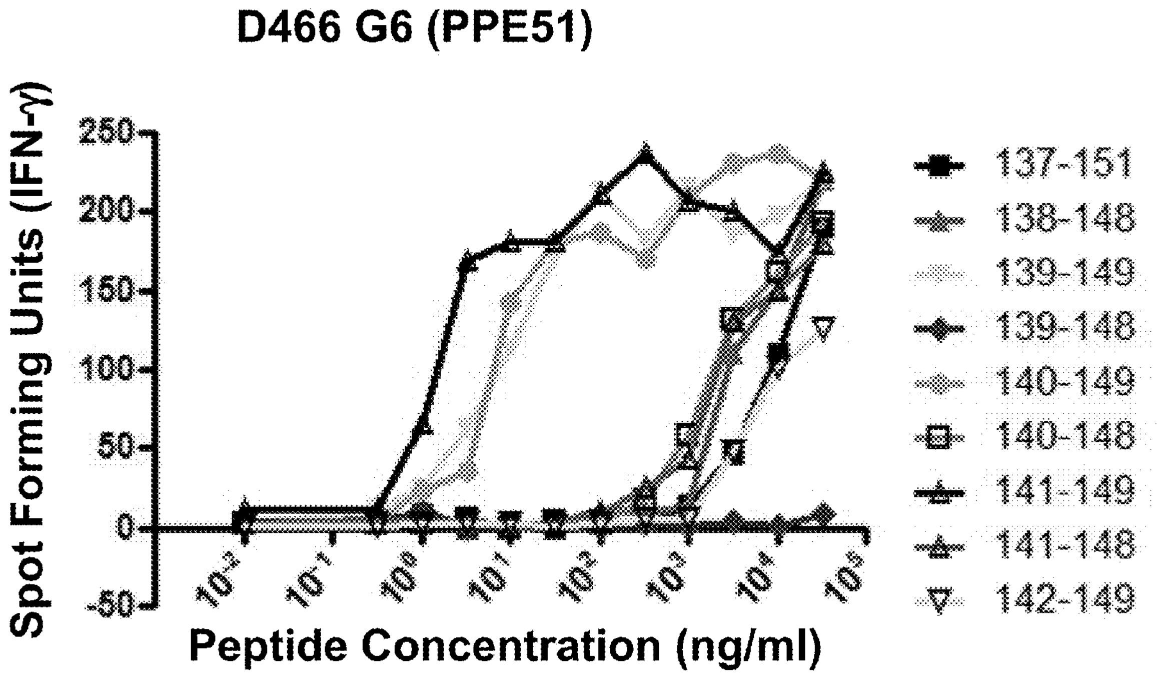
FIG. 4 is a graph showing SFU for peptides covering amino acids 137-151 of Rv3136.

Using the 15 mer $Rv3136_{137-151}$, T cell clones were generated to the peptide using the methods described. Having derived an antigen-specific $CD8^+$ T cell clone, the minimal epitope was determined. The minimal epitope was defined as the epitope which allowed for T cell recognition at the lowest concentration of peptide. Each 9-mer, 10-mer, and 11-mer peptide within the 15-mer was tested over a broad range of peptide concentrations, and by definition, the peptide eliciting a response at the lowest peptide concentration is the minimal epitope. Peptides including amino acids 139-149 of Rv3136 (SEQ ID NO: 2) allowed for T cell recognition at the lowest concentrations (FIG. 4), with amino acids 141-49 eliciting a response at the lowest concentration of all tested peptides.

Example 5

Animal Models

In tuberculosis research, mouse and guinea pig models have been used extensively to model various aspects of the disease.

A. Mouse Model:

Mice can be infected by a variety of routes, including intravenous, intraperitoneal and tracheal. One route is aerosolization of the infectious organism for respiratory infection. The mice are exposed to the aerosol in a chamber (wither whole body or nose only infection). The dose of invention can be varied by manipulating the concentration of Mtb in the nebulizer or time of exposure. A low dose infection, such as about 50 colony forming units (CFU) via aerosol, results in a slow and steady increase in bacterial numbers in the lungs, generally reaching a peak in four weeks, which coincides with the peak number of T cells in the lungs. The initial period is considered the acute stage of infection. Following infection, there is a dissemination of bacteria to the mediastinal lymph nodes. T cell priming is generally detectable between two and three weeks. After about four weeks the bacterial numbers stabilize, and there is a slow progressive pathologic response. This system is of use for modeling active infection. Thus, the above-described polypeptides, or polynucleotides encoding these polypeptides, can be administered prior to infection. The ability of the Mtb polypeptides (or polynucleotides encoding these polypeptides) to inhibit or prevent infection is then assessed. Alternatively, the mice are administered Mtb, and the ability of the Mtb polypeptide (or polynucleotide encoding these polypeptides) to treat the Mtb infection is monitored. The effectiveness of the Mtb polypeptides (or polynucleotides) can be monitored by measuring the T cell response, such as the number of $CD8^+$ or $CD4^+$ T cells, and/or measuring the bacterial numbers, and/or evaluating the pathology.

Exemplary protocols are provided below (see also Repique et al., *Infec. Immun.* 70: 3318-3323, 2002, incorporated herein by reference for an additional protocol).

1. Short Term Mouse Model:

$C_{57}$BL/6 mice are vaccinated with a composition including one or more Mtb polypeptide, or a polynucleotide encoding these one or more polypeptides according to the appropriate protocol and then rested for 4 to 6 weeks Immunized mice are infected with a low dose aerosol (50-100 CFU) of virulent *M. tuberculosis* and protection is evaluated by assessing the number of viable bacilli 30 days post challenge.

Viable counts are performed on the lung and spleen of mice by homogenizing the organs and plating serial 10-fold dilutions on 7H11 agar plates. Plates are incubated for up to 21 days and the number of colony forming units per organ determined.

BCG vaccinated mice have approximately 1 $Log_{10}$ protection in their lung and spleen when compared to PBS-treated mice.

B. Guinea Pig Models:

1. Short Term Guinea Pig Model

Out-bred Hartley guinea pigs are vaccinated with a composition including one or more Mtb polypeptide, or a polynucleotide encoding these one or more polypeptides, and then rested for 8 to 10 weeks Immunized guinea pigs are infected with a low dose aerosol (10-30 CFU) of virulent *M. tuberculosis* and protection is evaluated by assessing the number of viable bacilli 30 days post challenge.

Viable counts are performed on the lung and spleen of guinea pigs by homogenizing the organs and plating serial 10-fold dilutions on 7H11 agar plates. Plates are incubated for up to 21 days and the number of colony forming units per organ determined. Lung and spleen segments are also taken for histological analyses.

BCG vaccinated guinea pigs have approximately 2-3 $Log_{10}$ protection in their lung and spleen when compared to PBS-treated guinea pigs. In addition, BCG vaccinated guinea pigs have well defined granulomas when compared to unvaccinated animals.

2. Long Term Guinea Pig Model

The guinea pig model is similar to the mouse model, but the experiments are open-ended survival type and can last for as long as 2 years. Guinea pigs develop "classical" granulomas similar to humans with active TB, and as lung tissue necrosis progresses, they begin to lose weight and die of TB similar to humans. The number of colony forming units in the lungs and spleen can be assessed. Histological examination can also be performed to determine the degree of lung involvement and tissue destruction. After low-dose aerosol exposure in the guinea pig the number of organisms increases progressively during the first three weeks and then plateaus into a chronic state. During the later stages of infection there is increased bacterial load in the lung and this is associated with a worsening pathological condition. Without treatment, there is a concomitant rise in both CD4 and CD8 T cells in the lungs of infected guinea pigs.

Out-bred Hartley guinea pigs are vaccinated with the experimental vaccine (such as a composition including one or more Mtb polypeptide, or a polynucleotide encoding these one or more polypeptides) according to the appropriate protocol and then rested for 8 to 10 weeks Immunized guinea pigs are then infected with a low dose aerosol (10-30 CFU) of virulent *M. tuberculosis*. Guinea pigs are weighed weekly and monitored daily for signs of disease (such as increased respiration and failure to thrive). Unvaccinated guinea pigs succumb to infection from 20 to 25 weeks post challenge, while BCG vaccinated guinea pigs survive for 50 to 55 weeks post challenge.

At necropsy, the lung and spleen are assessed for the number of CFU and the extent of pathology. The relative protection of the experimental composition is compared to BCG vaccinated animals.

Example 6

Methods of Treating or Inhibiting Tuberculosis in a Subject

This example describes methods that can be used to induce an immune response in a subject that has or is at risk of having tuberculosis. In particular examples, the method includes selecting a subject having, thought to have, or at risk of having tuberculosis. Subjects having or thought to have tuberculosis include those with symptoms such as persistent cough, blood-tinged sputum, fever, weight loss, Ghon complex, or a positive diagnostic test (such as a tuberculin skin test). Subjects at risk of tuberculosis include those with exposure to an infected individual, those in an area where tuberculosis is endemic, and immunocompromised individuals.

Subjects selected for treatment can be administered a therapeutic amount of a disclosed immunogenic Mtb polypeptide or immunogenic fragment thereof or a polynucleotide encoding the polypeptide or fragment thereof. In some examples, a Mtb polypeptide or immunogenic fragment thereof or a polynucleotide encoding the polypeptide or fragment thereof is administered to the subject at doses of about 0.1 μg to 10 mg of immunogenic Mtb polypeptide or polynucleotide encoding the polypeptide. Dosages from 0.1 mg to about 100 mg per subject can be used, particularly if the agent is administered to a secluded site and not into the circulatory or lymph system, such as into a body cavity or into a lumen of an organ. However, the particular dose can be determined by a skilled clinician. The disclosed Mtb polypeptide (or immunogenic fragment thereof) or polynucleotide encoding the polypeptide or fragment thereof can be administered in one or several doses, for example continuously, daily, weekly, or monthly. When administered sequentially, the time separating the administration of the disclosed Mtb polypeptide (or immunogenic fragment thereof) or a polynucleotide encoding the polypeptide or fragment thereof can be seconds, minutes, hours, days, or even weeks.

The mode of administration can be any used in the art. The amount of agent administered to the subject can be determined by a clinician, and may depend on the particular subject treated. Specific exemplary amounts are provided herein (but the disclosure is not limited to such doses).

It will be apparent that the precise details of the methods or compositions described may be varied or modified without departing from the spirit of the described invention. We claim all such modifications and variations that fall within the scope and spirit of the claims below.

We claim:

1. A method for producing an immune response in a subject, comprising administering to the subject a therapeutically effective amount of a viral expression vector comprising a promoter operably linked to a polynucleotide encoding a polypeptide, wherein the polypeptide comprises the amino acid sequence set forth as SEQ ID NO: 16, thereby inducing the immune response to the polypeptide.

2. The method of claim 1, wherein the polypeptide consists of the amino acid sequence set forth as SEQ ID NO: 16.

3. The method of claim 1, further comprising administering a therapeutically effective amount of an adjuvant to the subject.

4. The method of claim 1, wherein the subject is at risk for infection with *Mycobacterium tuberculosis* (Mtb).

5. The method of claim 1, wherein the viral expression vector is a poxvirus vector.

6. The method of claim 5, wherein the poxvirus vector is a vaccinia virus vector.

7. The method of claim 6, wherein the vaccinia virus vector is a non-replicating vaccinia virus.

8. The method of claim 5, wherein the poxvirus vector is a modified vaccinia Ankara virus.

9. The method of claim 1, wherein the subject is infected with *Mycobacterium tuberculosis*.

10. The method of claim 1, wherein the subject has a latent infection with *Mycobacterium tuberculosis*.

11. The method of claim 1, wherein the promoter is the thymidine kinase promoter.

12. The method of claim 1, wherein the viral expression vector encodes a carrier protein.

13. The method of claim 1, wherein the viral expression vector encodes a cytokine or a co-stimulatory molecule.

14. The method of claim 1, wherein the subject is immunocompromised.

15. The method of claim 1, wherein the subject has primary tuberculosis.

* * * * *